US012673089B2

(12) United States Patent
Redondo et al.

(10) Patent No.: US 12,673,089 B2
(45) Date of Patent: Jul. 7, 2026

(54) METHODS FOR TREATING OSTEOARTHRITIS

(71) Applicants: President and Fellows of Harvard College, Cambridge, MA (US); Salk Institute for Biological Studies, La Jolla, CA (US)

(72) Inventors: Paloma Martinez Redondo, San Diego, CA (US); Isabel Guillen-Guillen, San Diego, CA (US); Juan Carlos Izpisua Belmonte, La Jolla, CA (US); Noah Davidsohn, Brookline, MA (US); George M. Church, Brookline, MA (US); Pedro Guillen Garcia, Madrid (ES)

(73) Assignees: President and Fellows of Harvard College, Cambridge, MA (US); Salk Institute for Biological Studies, La Jolla, CA (US)

( * ) Notice: Subject to any disclaimer, the term of this patent is extended or adjusted under 35 U.S.C. 154(b) by 934 days.

(21) Appl. No.: 17/781,542

(22) PCT Filed: Dec. 4, 2020

(86) PCT No.: PCT/US2020/063319
§ 371 (c)(1),
(2) Date: Jun. 1, 2022

(87) PCT Pub. No.: WO2021/113642
PCT Pub. Date: Jun. 10, 2021

(65) Prior Publication Data
US 2023/0024183 A1     Jan. 26, 2023

Related U.S. Application Data

(60) Provisional application No. 62/944,027, filed on Dec. 5, 2019.

(51) Int. Cl.
| | |
|---|---|
| *A61K 38/00* | (2006.01) |
| *A61K 38/17* | (2006.01) |
| *A61K 48/00* | (2006.01) |
| *A61P 19/02* | (2006.01) |

(52) U.S. Cl.
CPC .......... *A61K 38/179* (2013.01); *A61K 48/005* (2013.01); *A61P 19/02* (2018.01)

(58) Field of Classification Search
CPC ..... A61K 38/179; A61K 48/005; A61P 19/02; C12N 15/86; C12N 2750/14143; C07K 14/495; C07K 14/71
See application file for complete search history.

(56) References Cited

U.S. PATENT DOCUMENTS

| | | | |
|---|---|---|---|
| 2002/0004037 A1 | 1/2002 | Koteliansky et al. |
| 2006/0258588 A1 | 11/2006 | Pike et al. |
| 2011/0177070 A1 | 7/2011 | Lofquist et al. |

FOREIGN PATENT DOCUMENTS

| | | |
|---|---|---|
| CN | 102015760 A | 4/2011 |
| CN | 109844124 A | 6/2019 |
| CN | 109996555 A | 7/2019 |
| JP | 2019-519221 A | 7/2019 |
| JP | 2019-526272 A | 9/2019 |
| WO | 2017/201527 A2 | 11/2017 |
| WO | 2018/098375 A1 | 5/2018 |

OTHER PUBLICATIONS

Apr. 15, 2021—(WO) International Search Report & Written Opinion—App. No. PCT/US2020/063319.
Chuchana et al., "Secreted a-Klotho maintains cartilage tissue homeostasis by repressing Nos. 2 and ZIP8-MMP13 catabolic axis," Aging, vol. 10, No. 6, pp. 1442-1453 (Jun. 19, 2018).
Martinez-Redondo et al., "aKLOTHO and sTGFbR2 treatment counteract the osteoarthritic phenotype developed in a rat model," Protein Cell, vol. 11, No. 3, pp. 219-226 (Mar. 2020).
Kuro-O Makoto, "The Klotho proteins in health and disease," Nature Reviews, Nephrology, Nature Publishing Group, vol. 15, No. 1, Nov. 19, 2018, pp. 27-44.
Feger Martina et al., "The production of fibroblast growth factor 23 is controlled by TGF-ß2," Scientific Reports, vol. 7, No. 1, Jul. 10, 2017, pp. 1-7.
Secreted α-Klotho maintains cartilage tissue homeostasis by repressing NOS2 and ZIP8-MMP13 catabolic axis, AGING, vol. 10, No. 6, 2018, pp. 1442-1453.

*Primary Examiner* — Jeanette M Lieb
(74) *Attorney, Agent, or Firm* — Banner & Witcoff, Ltd.

(57) ABSTRACT

Methods are provided for treating osteoarthritis by administering αKlotho protein and sTGFβ-R2 protein to a site within a mammal exhibiting symptoms of osteoarthritis, such as a knee joint. The αKlotho protein and the sTGFβ-R2 protein are both present at the osteoarthritic site.

24 Claims, 20 Drawing Sheets
(17 of 20 Drawing Sheet(s) Filed in Color)

Specification includes a Sequence Listing.

Safranin-O

Col10a                    RUNX2

HC

OAC

Sox9 Col2a ACAN

HC

OAC

Safranin-O

Col10a                RUNX2

MMP13

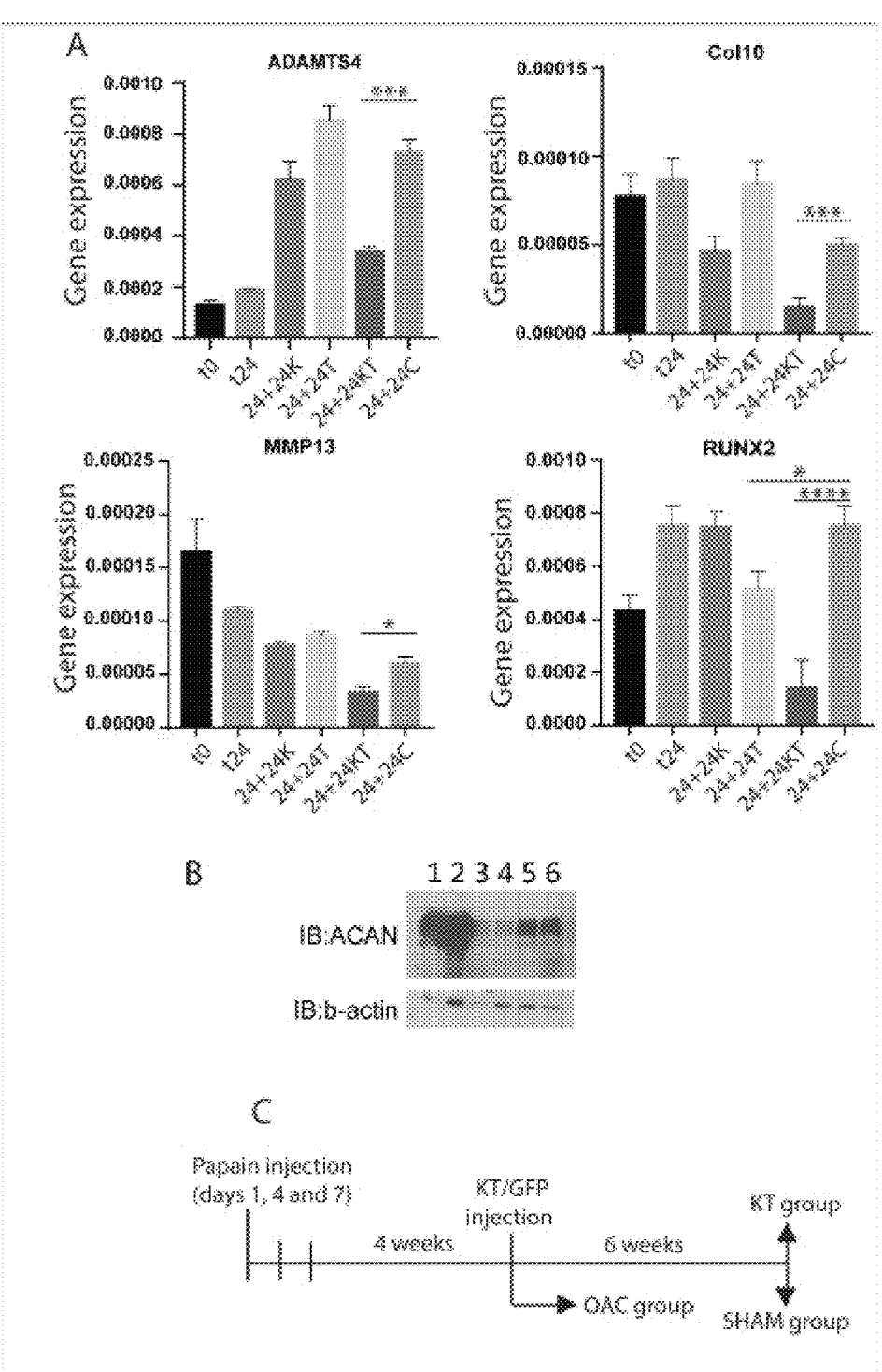
Fig. 12A-C

SEQUENCE LISTING

<160> NUMBER OF SEQ ID NOS: 16

<210> SEQ ID NO 1
<211> LENGTH: 892
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Thr Cys Ile Leu Gln Met Arg Phe Leu Arg Leu Gly Lys Ile
1               5                   10                  15

Leu Phe His Ser Ser Pro Gln Ser Thr Gly Gly Ser Gly Gly Thr Arg
                20                  25                  30

Gly Pro Arg Ala Pro Ala Gln Leu Arg Thr Gln Arg Gly Thr Asp Lys
            35                  40                  45

Leu Val Ala Lys Ser Glu Leu Lys Ala Lys Thr Ala His Arg Ala Leu
        50                  55                  60

Ala Asp His Phe Arg Asp Tyr Ala Glu Leu Cys Phe Arg His Phe Cys
65                  70                  75                  80

Gly Gln Val Lys Tyr Trp Ile Thr Ile Asp Asn Pro Tyr Val Val Ala
                85                  90                  95

Trp His Gly Tyr Ala Thr Gly Arg Leu Ala Pro Gly Val Arg Gly Ser
            100                 105                 110

Pro Arg Leu Gly Tyr Leu Val Ala His Asn Leu Leu Leu Ala His Ala
            115                 120                 125

Lys Ile Trp His Leu Tyr Asn Thr Ser Phe Arg Pro Thr Gln Gly Gly
        130                 135                 140

Gln Val Ser Ile Ala Leu Ser Ser His Trp Ile Asn Pro Arg Arg Met
145                 150                 155                 160

Thr Asp His Ser Ile Lys Glu Cys Gln Lys Ser Leu Asp Phe Val Leu
                165                 170                 175

Gly Trp Phe Ala Lys Pro Ile Phe Ile Asp Gly Asp Tyr Pro Glu Ser
            180                 185                 190

Met Lys Asn Asn Leu Ser Ser Leu Leu Pro Val Phe Thr Glu Ser Glu
            195                 200                 205

Lys Lys Phe Ile Lys Gly Thr Ala Asp Phe Phe Ala Leu Ser Phe Gly
        210                 215                 220

Pro Thr Leu Ser Phe Gln Leu Leu Asp Pro His Met Lys Phe His Gln
225                 230                 235                 240

Leu Glu Ser Pro Ser Leu Arg Gln Leu Leu Ser Trp Ile Asp Leu Glu
                245                 250                 255

Tyr Asn His Pro Gln Ile Phe Ile Val Glu Asn Gly Trp Phe Val Ser
            260                 265                 270

Gly Thr Thr Lys Arg Asp Asp Ala Lys Tyr Met Tyr Tyr Leu Lys Lys
            275                 280                 285

Phe Ile Met Glu Thr Leu Lys Ala Ile Arg Leu Asp Gly Val Asp Val
        290                 295                 300

Ile Gly Tyr Thr Ala Trp Ser Leu Met Asp Gly Phe Glu Trp His Arg
305                 310                 315                 320

Gly Tyr Ser Ile Arg Arg Gly Leu Phe Tyr Val Asp Phe Leu Ser Gln
                325                 330                 335

Asp Lys Lys Leu Leu Pro Lys Ser Ser Ala Leu Phe Tyr Gln Lys Leu
            340                 345                 350

```
Ile Glu Lys Asn Gly Phe Pro Pro Leu Pro Glu Asn Gln Pro Leu Glu
        355                 360                 365

Gly Thr Phe Pro Cys Asp Phe Ala Trp Gly Ile Val Asp Asn Tyr Ile
        370                 375                 380

Gln Val Asp Thr Thr Leu Ser Gln Phe Thr Asp Pro Asn Val Tyr Leu
385                 390                 395                 400

Trp Asp Val His His Ser Lys Arg Leu Ile Lys Val Asp Gly Leu Arg
                405                 410                 415

Ala Lys Lys Arg Lys Pro Tyr Cys Val Asp Phe Ala Ala Ile Gly Pro
            420                 425                 430

Gln Val Ala Leu Leu Gln Glu Met His Val Ser His Phe His Phe Ser
        435                 440                 445

Leu Asp Trp Ala Leu Leu Leu Pro Leu Gly Asn Gln Ser Arg Val Asn
    450                 455                 460

His Ala Ala Leu His Tyr Tyr Gly Cys Val Ala Ser Glu Leu Leu Arg
465                 470                 475                 480

Ala Asn Ile Thr Pro Val Val Ala Leu Trp Arg Pro Ala Ala Ala His
                485                 490                 495

Gln Gly Leu Pro Gly Pro Leu Ala Gln Arg Gly Ala Trp Glu Asn Pro
            500                 505                 510

Arg Thr Ala Leu Ala Phe Ala Glu Tyr Ala Arg Leu Cys Phe Arg Ala
        515                 520                 525

Leu Gly Arg His Val Lys Val Trp Ile Thr Leu Arg Glu Pro Pro Thr
    530                 535                 540

Arg Asn Leu Thr Leu Arg Ala Gly His Asn Leu Leu Arg Ala His Ala
545                 550                 555                 560

Leu Ala Trp Arg Val Tyr Asp Glu Gln Phe Arg Gly Ser Gln Gln Gly
                565                 570                 575

Lys Val Ser Ile Ala Leu Gln Ala Asp Trp Val Glu Pro Ala Cys Pro
            580                 585                 590

Ser Ser Gln Lys Asp Arg Glu Val Ala Glu Arg Val Leu Glu Phe Asp
        595                 600                 605

Val Gly Trp Leu Ala Glu Pro Ile Phe Gly Ser Gly Asp Tyr Pro Arg
    610                 615                 620

Leu Met Arg Asp Trp Leu Thr Arg Arg Asp His Ser Leu Leu Pro Tyr
625                 630                 635                 640

Phe Thr Asp Glu Glu Lys Arg Leu Ile Arg Gly Ser Phe Asp Phe Leu
                645                 650                 655

Ala Leu Ser His Tyr Thr Thr Ile Leu Val Asp Trp Glu Lys Glu Asp
            660                 665                 670

Pro Val Lys Tyr Asn Asp Tyr Leu Glu Val Gln Glu Met Thr Asp Ile
        675                 680                 685

Thr Trp Leu Asn Ser Pro Ser Gln Val Ala Val Val Pro Trp Gly Leu
    690                 695                 700

Arg Lys Val Leu Asn Trp Leu Lys Phe Lys Tyr Gly Asp Leu Pro Met
705                 710                 715                 720

Tyr Ile Val Ser Asn Gly Ile Asp Asp Asp Pro Arg Ala Ala Gln Asp
                725                 730                 735

Ser Leu Arg Val Tyr Tyr Met Gln Asn Tyr Val Asn Glu Ala Leu Lys
            740                 745                 750

Ala Tyr Val Leu Asp Gly Ile Asn Leu Cys Gly Tyr Phe Ala Tyr Ser
        755                 760                 765

Phe Asn Asp Arg Thr Ala Pro Lys Phe Gly Leu Tyr His Tyr Ala Ala
```

-continued

```
            770             775             780
Asn Gln Phe Glu Pro Lys Pro Ser Val Lys His Tyr Arg Lys Ile Ile
785             790             795             800

Asp Asn Asn Gly Phe Pro Gly Pro Glu Thr Leu Gly Arg Phe Cys Pro
                805             810             815

Glu Glu Phe Thr Leu Cys Thr Glu Cys Ser Phe Phe His Thr Arg Lys
            820             825             830

Ser Leu Leu Ala Phe Ile Ala Phe Leu Leu Phe Ala Phe Ile Ile Ser
        835             840             845

Leu Ser Leu Ile Phe Tyr Tyr Ser Arg Lys Gly Arg Arg Ser Tyr Lys
        850             855             860

Gly Gly Ser Gly Gly Ser Asp Tyr Lys Asp His Asp Gly Asp Tyr Lys
865             870             875             880

Asp His Asp Ile Asp Tyr Lys Asp Asp Asp Lys
            885             890
```

```
<210> SEQ ID NO 2
<211> LENGTH: 2682
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggccacct gcattttaca gatgagattc ctaaggctgg ggaagatact gttccactcc    60
agcccacaaa gcacaggtgg cagtggtggg acccggggac ctcgagctcc ggcacagctg   120
cgaacgcagc gtggcacaga taagttagtt gctaagtcag agctcaaggc taaaacggcc   180
caccgcgcgc tggccgacca cttcagggac tacgccgagc tctgcttccg ccacttctgc   240
ggccaggtca agtactggat caccatcgac aaccccctacg tggtggcctg cacggctac   300 gccaccggtc gcctggcacc cggagtcaga ggcagcccgc ggctcgggta cctggtggcg   360
cacaacctcc tcctggctca cgccaaaatc tggcatctct acaatacttc tttccgccca   420
actcagggag gccaggtatc cattgcccta agctcccact ggatcaatcc tcgaagaatg   480
accgaccata gcatcaaaga atgtcaaaaa tctcttgact ttgtactagg ctggtttgcc   540
aagcccatat ttattgatgg tgactatcct gagagcatga agaataacct gtcatctctt   600
ctgcctgttt ttactgaatc tgagaaaaag ttcatcaagg aacagctga cttttttgct   660 ctttcttttg gaccaacttt gagttttcaa ctcttggacc ctcatatgaa gttccaccaa   720
ttagaatctc ccagcctgag gcaactcctt tcttggattg accttgaata taaccaccct   780
caaatattta ttgtggaaaa tggctggttt gtctcaggga ccaccaagag agatgatgcc   840
aaatatatgt attacctcaa aaaattcata atggaaacct aaaagccat caggctggat   900 gggtggatg tcataggata cacagcgtgg tccccttatgg atggcttcga gtggcacaga   960
ggctacagca tcagacgtgg actcttctac gtggactttc taagccagga taagaaactg  1020
ttgccaaagt cttcagcctt gttctaccaa aagctgatag agaaaaatgg cttccctcct  1080
ttacctgaaa atcagcccct agaagggaca tttcccctgtg actttgcttg gggaattgtt  1140
gacaactaca ttcaagtgga caccactctg tctcagttta ccgacccgaa cgtttacctg  1200
tgggacgtcc atcacagcaa gaggctgatt aaggtggacg gctgcgggc caagaagagg  1260 aagcccctact gcgtggactt tgccgccatc gggccccagg tggccctgct gcaggagatg  1320
cacgtctcgc attttcactt ctcgctggac tgggccctgc tcctgccgct gggcaaccag  1380
```

-continued

```
tcccgggtga accacgcggc cctgcactac tacggctgcg tggccagcga gctcctgcgc    1440
gccaacatca ccccggtggt ggcgctctgg agaccagccg ctgcgcacca gggtctgcct    1500
ggaccgctgg cacagcgcgg tgcctgggag aacccacgca ccgccctggc gttcgccgag    1560
tacgcgcgcc tgtgcttccg cgccctgggc cgccacgtca aggtgtggat cacgctgcgc    1620
gagccgccca cgcggaacct gacgctccgc gccgggcaca acctgctgcg ggcgcacgcg    1680
ctggcctggc gcgtgtacga cgagcagttc cggggctcgc agcaggggaa ggtgtccatc    1740
gccctgcagg ccgactgggt ggagcccgcc tgcccctcct cccagaagga ccgcgaagtg    1800
gccgagaggg ttctggagtt cgacgtcggc tggctggccg agcccatctt cggctccggg    1860
gactacccgc ggctgatgcg cgactggctc acccggagag accattccct cctgccctat    1920
ttcactgacg aagagaagag gctaatccgg ggttcctttg acttcctggc cttgagccat    1980
tacaccacca tcctcgtgga ctgggaaaag gaagacccag tcaaatacaa tgattacctg    2040
gaagtgcagg agatgaccga catcacctgg ctcaactccc ccagtcaggt ggccgtagtg    2100
ccctggggcc tgcgcaaagt gctcaactgg ctcaagttca agtacggaga cctccccatg    2160
tatatcgtat ccaacggcat agatgacgat ccgcgggcag cccaggactc gttgagggtg    2220
tattacatgc agaactatgt aaatgaagct ctgaaagcct acgtattgga tggtatcaat    2280
ctttgtggat actttgccta ctcatttaat gatcgcacag ctccgaagtt tggcctctat    2340
cattatgctg caaaccagtt tgagcccaaa ccgtcggtga agcattacag gaaaattatt    2400
gacaacaatg gcttcccagg ccctgaaact ttggggcggt tttgtccaga ggaattcacc    2460
ctgtgcaccg aatgcagctt ttttcacacc cgaaagtctt tactggcttt catagctttc    2520
ctactttttg cttttattat ttctctttct ctgattttct actactctag gaaaggcaga    2580
agaagttata aaggagggag tggtgggtcc gattacaaag atcacgatgg ggactataaa    2640
gatcacgaca tcgactataa ggatgacgat gataaatgat ag                        2682
```

```
<210> SEQ ID NO 3
<211> LENGTH: 371
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asn Asn Asp Met Met Val Thr Asp Ser Asn Gly Val Ile Lys Phe Pro
1               5                   10                  15

Gln Leu Cys Lys Phe Cys Asp Val Arg Ser Ser Thr Cys Asp Asn Gln
            20                  25                  30

Lys Ser Cys Met Ser Asn Cys Ser Ile Thr Ser Ile Cys Glu Lys Pro
        35                  40                  45

His Glu Val Cys Leu Ala Val Trp Arg Lys Asn Asp Glu Asn Ile Thr
    50                  55                  60

Leu Glu Thr Leu Cys His Asp Pro Lys Asp Thr Tyr His Gly Ile Val
65                  70                  75                  80

Leu Glu Asp Ala Ala Ser Ser Lys Cys Ile Met Lys Glu Lys Lys Val
                85                  90                  95

Leu Gly Glu Thr Phe Phe Met Cys Ser Cys Ser Ser Asp Glu Cys Asn
            100                 105                 110

Asp Tyr Ile Ile Phe Ser Glu Glu Tyr Ala Thr Asn Asn Pro Asp Leu
            115                 120                 125
```

```
Leu Leu Val Ile Phe Gln Pro Lys Arg Glu Asn Gly Arg Val Pro Arg
    130                 135                 140

Pro Pro Asp Cys Pro Lys Cys Pro Ala Pro Glu Met Leu Gly Gly Pro
145                 150                 155                 160

Ser Val Phe Ile Phe Pro Pro Lys Pro Lys Asp Thr Leu Leu Ile Ala
                165                 170                 175

Arg Thr Pro Glu Val Thr Cys Val Val Val Asp Leu Asp Pro Glu Asp
            180                 185                 190

Pro Glu Val Gln Ile Ser Trp Phe Val Asp Gly Lys Gln Met Gln Thr
            195                 200                 205

Ala Lys Thr Gln Pro Arg Glu Glu Gln Phe Asn Gly Thr Tyr Arg Val
    210                 215                 220

Val Ser Val Leu Pro Ile Gly His Gln Asp Trp Leu Lys Gly Lys Gln
225                 230                 235                 240

Phe Thr Cys Lys Val Asn Asn Lys Ala Leu Pro Ser Pro Ile Glu Arg
                245                 250                 255

Thr Ile Ser Lys Ala Arg Gly Gln Ala His Gln Pro Ser Val Tyr Val
                260                 265                 270

Leu Pro Pro Ser Arg Glu Glu Leu Ser Lys Asn Thr Val Ser Leu Thr
            275                 280                 285

Cys Leu Ile Lys Asp Phe Phe Pro Pro Asp Ile Asp Val Glu Trp Gln
    290                 295                 300

Ser Asn Gly Gln Gln Glu Pro Glu Ser Lys Tyr Arg Thr Thr Pro Pro
305                 310                 315                 320

Gln Leu Asp Glu Asp Gly Ser Tyr Phe Leu Tyr Ser Lys Leu Ser Val
                325                 330                 335

Asp Lys Ser Arg Trp Gln Arg Gly Asp Thr Phe Ile Cys Ala Val Met
            340                 345                 350

His Glu Ala Leu His Asn His Tyr Thr Gln Glu Ser Leu Ser His Ser
    355                 360                 365

Pro Gly Lys
    370
```

```
<210> SEQ ID NO 4
<211> LENGTH: 1269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgggtcggg ggctgctccg gggcctgtgg ccgctgcata tcgtcctgtg gacgcgcatc      60
gccagcacga ataatgacat gatggtcact gacagcaatg gtgtcatcaa atttccacaa     120
ttgtgtaaat tttgtgatgt gagatcttcc acctgtgaca accagaaatc ttgcatgagc     180
aactgcagca ttacatccat ctgtgagaag ccacatgaag tctgtctggc tgtctggaga     240
aagaatgatg agaacataac actagagact ctctgccatg accccaagga tacctaccat     300
ggaattgttc tcgaagatgc tgcctcttcg aagtgcatta tgaaagaaaa gaaggtgctg     360
ggggagactt tctttatgtg ttcctgtagc tccgacgagt gcaacgacta catcatcttc     420
tctgaagaat atgccaccaa caaccctgac ttgttgttag tcatattcca acccaaaaga     480
gaaaatggaa gagttcctcg cccacctgat tgtcccaaat gcccagcccc tgaaatgctg     540
ggagggcctt cggtcttcat ctttcccccg aaacccaagg acaccctctt gattgcccga     600
```

```
acacctgagg tcacatgtgt ggtggtggat ctggacccag aagaccctga ggtgcagatc    660
agctggttcg tggacggtaa gcagatgcaa acagccaaga ctcagcctcg tgaggagcag    720
ttcaatggca cctaccgtgt ggtcagtgtc ctccccattg ggcaccagga ctggctcaag    780
gggaagcagt tcacgtgcaa agtcaacaac aaagccctcc catccccgat cgagaggacc    840
atctccaagg ccagagggca agcccatcag cccagtgtgt atgtcctgcc gccatcccgg    900
gaggagttga gcaagaacac agtcagcttg acatgcctga tcaaagactt cttcccacct    960
gacattgatg tggagtggca gagcaatgga cagcaggagc ctgagagcaa gtaccgcacg    1020
accccgcccc agctggacga ggacgggtcc tacttcctgt acagcaagct ctctgtggac    1080
aagagccgct ggcagcgggg agacaccttc atatgtgcgg tgatgcatga agctctacac    1140
aaccactaca cacaggaatc cctctcccat tctccgggta aaggagggag tggtgggtcc    1200
gattacaaag atcacgatgg ggactataaa gatcacgaca tcgactataa ggatgacgat    1260
gataaatga                                                           1269
```

```
<210> SEQ ID NO 5
<211> LENGTH: 330
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

-continued

```
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 232
<212> TYPE: PRT
<213> ORGANISM: Mus musculus

<400> SEQUENCE: 6

Pro Arg Gly Pro Thr Ile Lys Pro Cys Pro Pro Cys Lys Cys Pro Ala
1               5                   10                  15

Pro Asn Leu Glu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
            35                  40                  45

Val Asp Val Ser Glu Asp Asp Pro Asp Val Gln Ile Ser Trp Phe Val
    50                  55                  60

Asn Asn Val Glu Val His Thr Ala Gln Thr Gln Thr His Arg Glu Asp
65                  70                  75                  80

Tyr Asn Ser Thr Leu Arg Val Val Ser Ala Leu Pro Ile Gln His Gln
                85                  90                  95

Asp Trp Met Ser Gly Lys Ala Phe Ala Cys Ala Val Asn Asn Lys Asp
            100                 105                 110

Leu Pro Ala Pro Ile Glu Arg Thr Ile Ser Lys Pro Lys Gly Ser Val
            115                 120                 125

Arg Ala Pro Gln Val Tyr Val Leu Pro Pro Pro Glu Glu Glu Met Thr
            130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
            195                 200                 205

Ser Cys Ser Val Val His Glu Gly Leu His Asn His His Thr Thr Lys
            210                 215                 220

Ser Phe Ser Arg Thr Pro Gly Lys
225                 230

<210> SEQ ID NO 7
<211> LENGTH: 237
<212> TYPE: PRT
<213> ORGANISM: Canis lupus familiaris

<400> SEQUENCE: 7

Pro Lys Arg Glu Asn Gly Arg Val Pro Arg Pro Pro Asp Cys Pro Lys
```

-continued

```
1               5                   10                  15

Cys Pro Ala Pro Glu Met Leu Gly Gly Pro Ser Val Phe Ile Phe Pro
            20                  25                  30

Pro Lys Pro Lys Asp Thr Leu Leu Ile Ala Arg Thr Pro Glu Val Thr
        35                  40                  45

Cys Val Val Val Asp Leu Asp Pro Glu Asp Pro Glu Val Gln Ile Ser
    50                  55                  60

Trp Phe Val Asp Gly Lys Gln Met Gln Thr Ala Lys Thr Gln Pro Arg
65                  70                  75                  80

Glu Glu Gln Phe Asn Gly Thr Tyr Arg Val Val Ser Val Leu Pro Ile
                85                  90                  95

Gly His Gln Asp Trp Leu Lys Gly Lys Gln Phe Thr Cys Lys Val Asn
            100                 105                 110

Asn Lys Ala Leu Pro Ser Pro Ile Glu Arg Thr Ile Ser Lys Ala Arg
            115                 120                 125

Gly Gln Ala His Gln Pro Ser Val Tyr Val Leu Pro Pro Ser Arg Glu
        130                 135                 140

Glu Leu Ser Lys Asn Thr Val Ser Leu Thr Cys Leu Ile Lys Asp Phe
145                 150                 155                 160

Phe Pro Pro Asp Ile Asp Val Glu Trp Gln Ser Asn Gly Gln Gln Glu
                165                 170                 175

Pro Glu Ser Lys Tyr Arg Thr Thr Pro Pro Gln Leu Asp Glu Asp Gly
            180                 185                 190

Ser Tyr Phe Leu Tyr Ser Lys Leu Ser Val Asp Lys Ser Arg Trp Gln
        195                 200                 205

Arg Gly Asp Thr Phe Ile Cys Ala Val Met His Glu Ala Leu His Asn
    210                 215                 220

His Tyr Thr Gln Glu Ser Leu Ser His Ser Pro Gly Lys
225                 230                 235
```

```
<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 8

Met Gly Arg Gly Leu Leu Arg Gly Leu Trp Pro Leu His Ile Val Leu
1               5                   10                  15

Trp Thr Arg Ile Ala Ser Thr
            20

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 9
cctgaacacc tgcaacgggc ctgccaccat gctagcccgc gcccctcc                  48

<210> SEQ ID NO 10
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 10
cctgaacgtc tcgctagctt attacttata acttctctgg cc                          42

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctgaacacc tgcaacgggc ctgccaccat gggtcggggg tgctccgg                    48

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcttgattg tgggccctct ggggtcggga ctgctggtgg tgtattc                     47

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaatacacca ccagcagtcc cgaccccaga gggcccacaa tcaagcc                     47

<210> SEQ ID NO 14
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctgaacacc tgccttacta gctcatttac ccggagtccg ggagaag                     47

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15 ggaacccct a gtgatggagt t                                                21

<210> SEQ ID NO 16
<211> LENGTH: 16
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 16
cggcctcagt gagcga                                                              16

METHODS FOR TREATING OSTEOARTHRITIS

RELATED APPLICATIONS

This application is a National Stage Application under 35 U.S.C. 371 of co-pending PCT application PCT/US2020/063319 designating the United States and filed Dec. 4, 2020; which claims the benefit of U.S. provisional application No. 62/944,027 filed on Dec. 5, 2019 each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 28, 2021, is named 010498_01389WO_SL.txt and is 26,081 bytes in size.

BACKGROUND

During aging, articular cartilage is a tissue that undergoes substantial changes in the matrix structure, molecular composition, metabolic activity, and mechanical properties (see Rahmati M, Nalesso G, Mobasheri A, Mozafari M. Aging and osteoarthritis: Central role of the extracellular matrix. Ageing Research Reviews. 2017 Nov. 1; 40:20-30; Loeser R F, Collins J A, Diekman B O. Ageing and the pathogenesis of osteoarthritis. Nat Rev Rheumatol. 2016 July; 12(7):412-20). As a result, articular cartilage experiences impaired homeostasis and limited capacity to undergo repair, contributing to osteoarthritis (OA) development (Loeser R F, Collins J A, Diekman B O. Aging and the pathogenesis of osteoarthritis. Nat Rev Rheumatol. 2016 July; 12(7):412-20). Osteoarthritis is the most prevalent musculoskeletal disorder among the elderly and is the leading cause of disability in the US due to pain associated with the disease (Zhang Y, Jordan J M. Epidemiology of Osteoarthritis. Clin Geriatr Med. 2010 August; 26(3):355-69). Although symptomatic pain relief is possible for this disease (Zhang W, Ouyang H, Dass C R, Xu J. Current research on pharmacologic and regenerative therapies for osteoarthritis. Bone Research. 2016 Mar. 1; 4:15040), treatments to cure this pathology are still unavailable.

The lack of effective clinical treatments for osteoarthritis favors the increasing incidence of this pathology worldwide (see Wittenauer R, Smith L, Aden K. Background Paper 6.12 Osteoarthritis. Background Paper. 2004; 31). Currently, the most effective treatment for osteoarthritis, besides arthroplasty, is autologous chondrocyte transplantation. However, this treatment has several limitations including the need to extract healthy donor cartilage by an independent surgical procedure, the limited expansion capacity of primary chondrocytes and the difficulty of treating large-scale defects.

Therefore, there is still the need to find effective therapies that could avoid surgical procedures and treat this pathology associated not only with aging but also with joint trauma. There is further need for the development of therapeutic targets towards the enhancement of the low regenerative capacity shown during adulthood and worsening upon aging as well as helping in recovering articular cartilage structure and function after osteoarthritis.

SUMMARY

The present disclosure provides a method of treating osteoarthritis in a mammal in need thereof by administering a therapeutically effective amount of αKlotho protein or an active fragment thereof and a therapeutically effective amount of sTGFβ-R2 protein or an active fragment thereof or a combination thereof to the mammal at a site within the mammal exhibiting osteoarthritis, wherein progression of the osteoarthritis is reduced compared to the untreated condition, or wherein cartilage at the site of the osteoarthritis is increased or regenerated or regrown compared to the untreated condition, or wherein inflammation is reduced compared to the untreated condition. An osteoarthritic site is one which exhibits symptoms of osteoarthritis. Osteoarthritis is the most common form of arthritis, affecting millions of people worldwide. It occurs when the protective cartilage that cushions the ends of your bones wears down over time. Although osteoarthritis can damage any joint, the disorder most commonly affects joints in your hands, knees, hips and spine. Symptoms of osteoarthritis include pain, stiffness, tenderness, loss of flexibility, grating sensation, bone spurs and swelling.

Functional proteins as described herein can be the full length proteins or proteins which vary from the full length proteins but retain the activity in whole or in part of the full length protein.

Further features and advantages of certain embodiments of the present invention will become more fully apparent in the following description of embodiments and drawings thereof, and from the claims.

BRIEF DESCRIPTION OF THE DRAWINGS

The patent or application file contains drawings executed in color. Copies of this patent or patent application publication with the color drawings will be provided by the Office upon request and payment of the necessary fee. The foregoing and other features and advantages of the present embodiments will be more fully understood from the following detailed description of illustrative embodiments taken in conjunction with the accompanying drawings in which:

FIG. 1A depicts a graph of joint osteoarthritis grade in rats based on the OARSI scoring system (HC, n=5; OAC, n=5). Data is expressed as means, and each data point represents an individual rat. Two-tailed t-test (unpaired) was used for the statistical analysis. *P<0.05, P<0.01, *P<0.001, ****P<0.0001. FIG. 1B depicts representative Safranin-O/Fast green images of knee joints (HC, n=5; OAC, n=5). Scale bars, 500 μm. The images show cartilage and matrix degradation 4 weeks after papain injection in the OAC group. FIG. 1D depicts representative images from immunostaining detection of hypertrophic markers Col10a and RUNX2 in knee sections (HC, n=3; OAC, n=3). Scale bars, 200 μm. Only Col10 images include DAPI co-staining (blue). Arrows in the Col10a image indicate the cartilage area characterized for Col10a absence in non-pathological joints. FIG. 1E depicts representative images from immunostaining detection MMP13 in knee sections (HC, n=3; OAC, n=3). Scale bars, 200 μm. The image shows green staining in nucleus for both groups, but only the OAC group shows staining outside the nuclear area. FIG. 1F depicts representative images from immunostaining detection of Sox9, Col2a, and ACAN in knee sections (HC, n=3; OAC, n=3). Scale bars, 200 µm. Only ACAN images include DAPI co-staining (blue).

FIG. 2A depicts results of immunostaining quantification of Sox9, Col2a and ACAN in tissue sections showing the prevention of cartilage degradation and recovery of cartilage markers after sTGFβR2 and αKlotho treatment as described herein. Quantification was performed within an area of 400×500 µm along the cartilage area. Quantification was performed using Fiji software: HC=healthy (blue), OAC=disease (red), SHAM=untreated (green), and KT=treated (purple) (HC, n=3; OAC, n=3; KT, n=3, and SHAM, n=3). Two-tailed t-test (unpaired) was used for statistical analysis. *P<0.05, P<0.01, *P<0.001, ****P<0.0001. FIG. 2B depicts a schematic of the time course for the osteoarthritis experiments. Female rats undergoing papain mediated osteoarthritis were either sacrificed after 4 weeks (OAC) or injected intra-articularly with AAVDJ-GFP (SHAM) or AAV-DJ-sTGFβR2 and AAV-DJ-αKlotho (KT). FIG. 2C depicts the results of quantification of the condyle cartilage thickness comparing the four groups demonstrating how sTGFβR2 and αKlotho treatment avoids hyaline cartilage destruction and promotes its formation (HC, n=5; OAC; n=5; KT, n=5, and SHAM, n=5). The thickness was determined by measuring the condyle cartilage at three different positions throughout the cartilage area. Quantification performed using Fiji software. Two-tailed t-test (unpaired) was used for statistical analysis. *P<0.05, P<0.01, *P<0.001, ****P<0.0001.

FIGS. 3A-3C are directed to experiments where sTGFβR2 and αKlotho have been delivered by AAV-DJ serotype. FIG. 3A depicts representative whole-body luminescence images on day 14 after AAV-DJ-Luciferase (LUC) or AAV-DJ-Empty (sham) intra-articular injection (LUC, n=3; Sham, n=3) (left) and quantification of luminescence (in arbitrary units, A.U.). FIG. 3B depicts flow cytometry analysis of AAV-DJ-GFP in vitro transduced rat synovial cells which showed more than 15% transduction efficiency (upper, non-transduced cells; lower, AAV-DJ-GFP transduced cells) (n=3). FIG. 3C depicts flow cytometry analysis of AAV-DJ-GFP in vitro transduced rat chondrocytes which showed less than 4% efficiency of transduction (left, non-transduced cells; right, AAV-DJ-GFP transduced cells) (n=3).

FIG. 4A depicts representative Safranin-O/Fast green images of knee joints (SHAM, n=5; KT, n=5) (scale bars, 500 µm) which show high cartilage and matrix degradation in the SHAM group, greater than for the OAC group. KT treated knees show a complete cartilage structure with high safranin-O staining. FIG. 4B depicts representative images from immunostaining detection of chondrocyte specific markers Sox9, Col2a, and ACAN in knee sections (SHAM, n=3; KT, n=3). Scale bars, 200 µm. FIG. 4C depicts in situ cell death representative images (SHAM, n=4; KT, n=5). Blue colored cells represent apoptotic cells. Scale bars, 20 µm. The images show higher number of blue colored cells in the SHAM group. FIG. 4D depicts representative images from immunostaining detection of hypertrophic markers Col10a and RUNX2 in knee sections (SHAM, n=3; KT, n=3). Scale bars, 200 µm. Only Col10 images include DAPI co-staining (blue). FIG. 4E depicts representative images from immunostaining detection MMP13 in knee sections (SHAM, n=3; KT, n=3). Scale bars, 200 µm. The image shows green staining in nucleus for both groups, but only the SHAM group shows staining outside the nuclear area. FIG. 4F depicts results of joint osteoarthritis grade in rats based on the OARSI scoring system (SHAM, n=5; KT, n=5). Data is expressed as means, and each data point represents an individual rat. Two-tailed t-test (unpaired) was used for the statistical analysis. *P<0.05, P<0.01, *P<0.001, ****P<0.0001.

FIG. 5A depicts a barplot of the statistical enrichment scores from common DE genes between [KT vs SHAM] and [HC vs OAC] (genes that shared common change in KT and HC, but behave differently in the other groups) according to Gene Ontology enrichment analysis. Only Biological Process terms with FDR (false discovery rate)<0.01 were shown in the plot. FIG. 5B depicts a barplot of the statistical enrichment scores from KT vs SHAM DE genes (genes that were not identified as DE from HC vs OAC) according to Gene Ontology enrichment analysis. Only Biological Process terms with FDR (false discovery rate)<0.01 were shown in the plot. FDR values were shown in −log 10 scale. FIG. 5C depicts a heatmap of gene expression for downregulated DE genes that shared common change in KT and HC, but behave differently in the other two groups. Colors indicated the gene-wise relative expression values across conditions (low=blue, high=red). Row dendrogram showed the hierarchical clustering result based on the similarity of gene expression profile. FIG. 5D depicts gene expression plots of selected genes (from FIG. 5C and FIG. 7). Gene expression was normalized into FPKM values (Fragments Per Kilobase Per Million mapped reads) with the mean shown as the bar and each individual replicate shown as the dot. Colors referred to different conditions: HC (blue), OAC (red), SHAM (green), and KT (purple) (HC, n=2; KT, n=2; OAC, n=3; and SHAM, n=3). FIG. 5E depicts gene expression plots of Nos2 (from FIG. 7). Gene expression was normalized into FPKM values (Fragments Per Kilobase Per Million mapped reads) with the mean shown as the bar and each individual replicate shown as the dot. Colors referred to different conditions: HC (blue), OAC (red), SHAM (green), and KT (purple) (HC, n=2; KT, n=2; OAC, n=3; and SHAM, n=3).

FIG. 6A depicts a schematic representation of the co-culture assay using human fibroblasts and human chondrocytes (n=3). Scale bars, 200 µm. FIG. 6B depicts representative immunostaining images of Sox9 and Col2a from chondrocytes used in co-culture experiments (SHAM, n=3; KT, n=3). Scale bars, 200 µm. FIG. 6C depicts that immunostaining quantification of Sox9, Col2a and Ki67 demonstrated chondrocytes improvement when the mesenchymal cells were transduced with AAV-DJ-sTGFβR2 and AAV-DJ-αKlotho. Quantification performed by using Fiji software (SHAM, n=3; KT, n=3). FIG. 6D depicts that immunostaining quantification of Sox9, Col2a and EdU showed chondrocyte homeostasis improvement in those treated with sTGFβR2 and αKlotho recombinant proteins. Quantification performed by using Fiji software (BSA, n=3; KT, n=3). Two-tailed t-test (unpaired) was used for statistical analysis in b and c. *P<0.05, P<0.01, *P<0.001, ****P<0.0001.

FIG. 12A depicts data showing gene expression of various genes in response to treatment with a combination of sTGFβR2 and αKlotho versus sTGFβR2 individually and αKlotho individually. The combination synergistically achieved greater treatment effect compared to individual treatment. FIG. 12B depicts gel data demonstrating that chondrocytes treated with both factors showed higher protein expression of ACAN that each factor separately. FIG. 12C depicts the time line of injection.

DETAILED DESCRIPTION

Figure 1A:
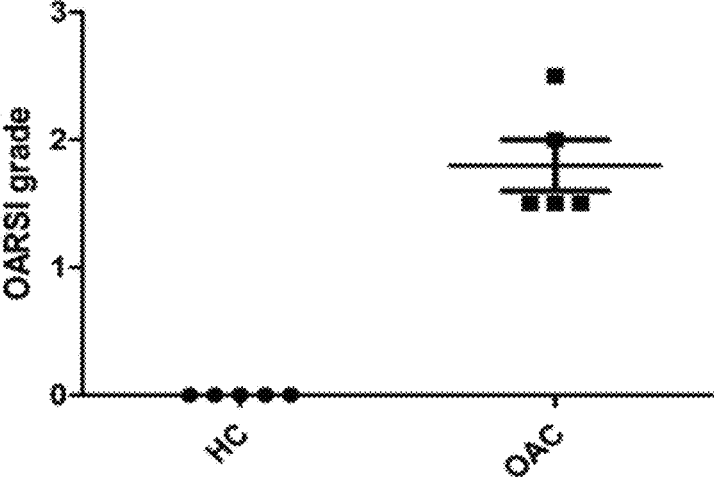
FIGS. 1A-1F depict results of recapitulation of early-stage osteoarthritis phenotype in a rat model.

The present disclosure provides methods and compositions for treating or preventing osteoarthritis, such as occurs with articular cartilage, using a therapeutically effective amount of a combination of αKlotho protein or an active fragment thereof and Soluble Tumor Growth Factor β receptor 2 (sTGFβR2) protein or an active fragment thereof which is administered to a mammal in need thereof as soluble proteins or a vector which is used to express the soluble proteins at a site within the mammal exhibiting osteoarthritis. According to one aspect, Soluble Tumor Growth Factor β receptor 2 (sTGFβR2) is administered with αKlotho protein to treat or prevent osteoarthritis in joints such as the knee where articular cartilage is present. According to one aspect, Soluble Tumor Growth Factor β receptor 2 (sTGFβR2) and αKlotho are administered separately or simultaneously such that the Soluble Tumor Growth Factor β receptor 2 (sTGFβR2) and αKlotho are both present at the site of administration. According to one aspect, the αKlotho protein or an active fragment thereof and the sTGFβ-R2 protein or an active fragment thereof are encoded by nucleic acids that are included in one or more vectors or combined into a single viral vector, such as an AAV, which are administered to treat or prevent osteoarthritis and/or diseases or conditions associated with osteoarthritis.

According to one aspect, sTGFβR2 acts to inhibit TGFβ1 thereby inhibiting osteophyte formation despite increasing proteoglycans degradation (see Scharstuhl A, Glansbeek H L, van Beuningen H M, Vitters E L, van der Kraan P M, van den Berg W B. Inhibition of endogenous TGF-beta during experimental osteoarthritis prevents osteophyte formation and impairs cartilage repair. J Immunol. 2002 Jul. 1; 169 (1):507-14). The TGFβ1 pathway regulates cartilage homeostasis in such a way that its balance and downstream effectors are essential for cartilage maintenance. On one hand, TGFβ1 has been considered as essential for the cartilage formation due to its role in chondrocyte proliferation and maturation, avoiding chondrocyte hypertrophy (Yang X, Chen L, Xu X, Li C, Huang C, Deng C X. TGF-beta/Smad3 signals repress chondrocyte hypertrophic differentiation and are required for maintaining articular cartilage. J Cell Biol. 2001 Apr. 2; 153(1):35-46). However, on the other hand, either the increase of ALK1/ALK5 receptors ratio (see Blaney Davidson E N, Remst D F G, Vitters E L, van Beuningen H M, Blom A B, Goumans M-J, et al. Increase in ALK1/ALK5 ratio as a cause for elevated MMP-13 expression in osteoarthritis in humans and mice. J Immunol. 2009 Jun. 15; 182(12):7937-45); or prolonged exposure to TGF-β1 drastically increases chondrocyte hypertrophy (see Pohlers D, Beyer A, Koczan D, Wilhelm T, Thiesen H-J, Kinne R W. Constitutive upregulation of the transforming growth factor-β pathway in rheumatoid arthritis synovial fibroblasts. Arthritis Research & Therapy. 2007 Jun. 26; 9(3):R59; Bakker A C, van de Loo F A, van Beuningen H M, Sime P, van Lent P L, van der Kraan P M, et al. Overexpression of active TGF-beta-1 in the murine knee joint: evidence for synovial-layer-dependent chondro-osteophyte formation. Osteoarthr Cartil. 2001 February; 9(2):128-36).

According to this one aspect, soluble TGFβR2 (sTGFβR2), which lacks the membrane binding domain and has high affinity for TGF-β1 and β3 (De Crescenzo G, Pham P L, Durocher Y, O'Connor-McCourt M D. Transforming Growth Factor-beta (TGF-β) Binding to the Extracellular Domain of the Type II TGF-β Receptor: Receptor Capture on a Biosensor Surface Using a New Coiled-coil Capture System Demonstrates that Avidity Contributes Significantly to High Affinity Binding. Journal of Molecular Biology. 2003 May; 328(5):1173-83), could then modulate the effect of TGF-β1 in the joint.

According to this one aspect, αKlotho inhibits or prevents extracellular matrix (ECM) degradation (see Chuchana P, Mausset-Bonnefont A-L, Mathieu M, Espinoza F, Teigell M, Toupet K, et al. Secreted α-Klotho maintains cartilage tissue homeostasis by repressing NOS2 and ZIP8-MMP13 catabolic axis. Aging (Albany NY). 2018 Jun. 19; 10(6):1442-53). Originally identified as an aging-suppressor gene in mice (see Kurosu H, Yamamoto M, Clark J D, Pastor J V, Nandi A, Gurnani P, et al. Suppression of aging in mice by the hormone Klotho. Science. 2005 Sep. 16; 309(5742): 1829-33) and shown to be downregulated in cartilage and synovial membrane upon aging and osteoarthritis (see Pásztói M, Nagy G, Géher P, Lakatos T, Tóth K, Wellinger K, et al. Gene expression and activity of cartilage degrading glycosidases in human rheumatoid arthritis and osteoarthritis synovial fibroblasts. Arthritis Research & Therapy. 2009; 11(3):R68), Klotho codifies for a type I membrane-bound protein whose extracellular domain is released to the circulation by a proteolytic cleavage (see Xu Y, Sun Z. Molecular basis of Klotho: from gene to function in aging. Endocr Rev. 2015 April; 36(2):174-93). The secreted protein, αKlotho, regulates surface glycoproteins such as ion channels, the insulin-like growth factor 1 (IGF-1)/insulin and Wnt from N-linked glycans by removing terminal sialic acids (see Dalton G D, Xie J, An S-W, Huang C-L. New Insights into the Mechanism of Action of Soluble Klotho. Front Endocrinol (Lausanne). 2017 Nov. 17; 8). αKlotho prevents apoptosis, oxidative stress, and immune reaction in certain organs (Fan J, Sun Z. The Antiaging Gene Klotho Regulates Proliferation and Differentiation of Adipose-Derived Stem Cells. Stem Cells. 2016 June; 34(6):1615-25; Tilly E L, Vinatier C, Ong T, Guicheux J, Beck L. Role of the anti-aging protein Klotho in the autophagy and senescence-associated development of osteoarthritis. Osteoarthritis and Cartilage. 2016 Apr. 1; 24:S64-5; Salech F, Varela-Nallar L, Arredondo S B, Bustamante D B, Andaur G A, Cisneros R, et al. Local Klotho enhances neuronal progenitor proliferation in the adult hippocampus. J Gerontol A Biol Sci Med Sci. 2017 Dec. 30).

According to one aspect, a method of treating osteoarthritis in a mammal in need thereof is provided including administering a therapeutically effective amount of a combination of αKlotho protein or an active fragment thereof and sTGFβ-R2 protein or an active fragment thereof to the mammal at a site within the mammal exhibiting osteoarthritis, wherein progression of the osteoarthritis is reduced compared to the untreated condition, or wherein cartilage at the site of the osteoarthritis is increased or regenerated or regrown compared to the untreated condition, or wherein inflammation is reduced compared to the untreated condition. According to one aspect, the mammal is a dog or a human. According to one aspect, the αKlotho protein or an active fragment thereof is administered as a soluble protein and the sTGFβ-R2 protein or an active fragment thereof is administered as a soluble protein. According to one aspect, the αKlotho protein or an active fragment thereof is administered as a soluble protein by intra-articular cartilage injection and the sTGFβ-R2 protein or an active fragment thereof is administered as a soluble protein by intra-articular cartilage injection. According to one aspect, a vector including a first nucleic acid sequence encoding the αKlotho protein or an active fragment thereof and a second nucleic acid sequence encoding the sTGFβ-R2 protein or an active fragment thereof is administered and the first nucleic acid sequence is expressed to produce the αKlotho protein or an active fragment thereof and the second nucleic acid sequence is expressed to produce the sTGFβ-R2 protein or an active fragment thereof. According to one aspect, a vector including a first nucleic acid sequence encoding the αKlotho protein or an active fragment thereof and a second nucleic acid sequence encoding the sTGFβ-R2 protein or an active fragment thereof is administered by intra-articular cartilage injection and the first nucleic acid sequence is expressed to produce the αKlotho protein or an active fragment thereof and the second nucleic acid sequence is expressed to produce the sTGFβ-R2 protein or an active fragment thereof.

According to one aspect, a first vector including a first nucleic acid sequence encoding the αKlotho protein or an active fragment thereof and a second vector including a second nucleic acid sequence encoding the sTGFβ-R2 protein or an active fragment thereof is administered and the first nucleic acid sequence is expressed to produce the αKlotho protein or an active fragment thereof and the second nucleic acid sequence is expressed to produce the sTGFβ-R2 protein or an active fragment thereof. According to one aspect, a first vector including a first nucleic acid sequence encoding the αKlotho protein or an active fragment thereof and a second vector including a second nucleic acid sequence encoding the sTGFβ-R2 protein or an active fragment thereof is administered by intra-articular cartilage injection and the first nucleic acid sequence is expressed to produce the αKlotho protein or an active fragment thereof and the second nucleic acid sequence is expressed to produce the sTGFβ-R2 protein or an active fragment thereof. According to one aspect, the vector is a recombinant virus. According to one aspect, the vector is a parvovirus. According to one aspect, the vector is an AAV vector. According to one aspect, the AAV vector is AAV-DJ. According to one aspect, the vector is an AAV vector serotyped for AAV1, AAV2, AAV3, AAV4, AAV5, AAV6, AAV7, AAV8, AAV9, AAV10, AAV11, AAV12, AAV2.5, or AAVrh10.XX (where xx represents different variants known to those of skill in the art, such as AAVrh10.01 to AAV rh 10.99 and example of which is AAVrh10.32) or combinations thereof. According to one aspect, the vector infects mesenchymal cells at the site of the osteoarthritis. According to one aspect, the first vector and the second vector are a recombinant virus. According to one aspect, the first vector and the second vector are a parvovirus. According to one aspect, the first vector and the second vector are an AAV vector. According to one aspect, the first vector and the second vector are an AAV-DJ vector. According to one aspect, the first vector and the second vector are an AAV vector serotyped for AAV1, AAV2, AAV3, AAV4, AAV5, AAV6, AAV7, AAV8, AAV9, AAV10, AAV11, AAV12, AAV2.5, or AAVrh10.XX (where xx represents the different known variants) or combinations thereof. According to one aspect, the first vector and the second vector infect mesenchymal cells at the site of the osteoarthritis. According to one aspect, the αKlotho protein or active fragment thereof and the sTGFβ-R2 protein or active fragment thereof are human proteins. According to one aspect, the αKlotho protein or active fragment thereof and the sTGFβ-R2 protein or active fragment thereof are canine proteins. According to one aspect, the αKlotho protein and the sTGFβ-R2 protein are selected from the group consisting of human, canine, feline, bovine, ovine, caprine, equine, murine and porcine proteins. According to one aspect, the αKlotho protein has at least 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity or 99.5% or 100% sequence identity to sequence to the amino acid sequence of an αKlotho protein corresponding to SEQ ID NO: 1 as follows:

```
MATCILQMRFLRLGKILFHSSPQSTGGSGGTRGPRAPAQLRTQRGTDKLV

AKSELKAKTAHRALADHFRDYAELCFRHFCGQVKYWITIDNPYVVAWHGY
```

-continued

ATGRLAPGVRGSPRLGYLVAHNLLLAHAKIWHLYNTSFRPTQGGQVSIAL

SSHWINPRRMTDHSIKECQKSLDFVLGWFAKPIFIDGDYPESMKNNLSSL

LPVFTESEKKFIKGTADFFALSFGPTLSFQLLDPHMKFHQLESPSLRQLL

SWIDLEYNHPQIFIVENGWFVSGTTKRDDAKYMYYLKKFIMETLKAIRLD

GVDVIGYTAWSLMDGFEWHRGYSIRRGLFYVDFLSQDKKLLPKSSALFYQ

KLIEKNGFPPLPENQPLEGTFPCDFAWGIVDNYIQVDTTLSQFTDPNVYL

WDVHHSKRLIKVDGLRAKKRKPYCVDFAAIGPQVALLQEMHVSHFHFSLD

WALLLPLGNQSRVNHAALHYYGCVASELLRANITPVVALWRPAAAHQGLP

GPLAQRGAWENPRTALAFAEYARLCFRALGRHVKVWITLREPPTRNLTLR

AGHNLLRAHALAWRVYDEQFRGSQQGKVSIALQADWVEPACPSSQKDREV

AERVLEFDVGWLAEPIFGSGDYPRLMRDWLTRRDHSLLPYFTDEEKRLIR

GSFDFLALSHYTTILVDWEKEDPVKYNDYLEVQEMTDITWLNSPSQVAVV

PWGLRKVLNWLKFKYGDLPMYIVSNGIDDDPRAAQDSLRVYYMQNYVNEA

LKAYVLDGINLCGYFAYSFNDRTAPKFGLYHYAANQFEPKPSVKHYRKII

DNNGFPGPETLGRFCPEEFTLCTECSFFHTRKSLLAFIAFLLFAFIISLS

LIFYYSRKGRRSYKGGSGGSDYKDHDGDYKDHDIDYKDDDDK**.

According to one aspect, the nucleic acid sequence encoding an αKlotho protein has at least 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity or 99.5% sequence or 100% sequence identity to the nucleic acid sequence encoding αKlotho protein corresponding to SEQ ID NO: 2 as follows:

ATGGCCACCTGCATTTTACAGATGAGATTCCTAAGGCTGGGGAAGATACT

GTTCCACTCCAGCCCACAAAGCACAGGTGGCAGTGGTGGGACCCGGGGAC

CTCGAGCTCCGGCACAGCTGCGAACGCAGCGTGGCACAGATAAGTTAGTT

GCTAAGTCAGAGCTCAAGGCTAAAACGGCCCACCGCGCGCTGGCCGACCA

CTTCAGGGACTACGCCGAGCTCTGCTTCCGCCACTTCTGCGGCCAGGTCA

AGTACTGGATCACCATCGACAACCCCTACGTGGTGGCCTGGCACGGCTAC

GCCACCGGTCGCCTGGCACCCGGAGTCAGAGGCAGCCGCGGCTCGGGTA

CCTGGTGGCGCACAACCTCCTCCTGGCTCACGCCAAAATCTGGCATCTCT

ACAATACTTCTTTCCGCCCAACTCAGGGAGGCCAGGTATCCATTGCCCTA

AGCTCCCACTGGATCAATCCTCGAAGAATGACCGACCATAGCATCAAAGA

ATGTCAAAAATCTCTTGACTTTGTACTAGGCTGGTTTGCCAAGCCCATAT

TTATTGATGGTGACTATCCTGAGAGCATGAAGAATAACCTGTCATCTCTT

CTGCCTGTTTTTACTGAATCTGAGAAAAAGTTCATCAAGGGAACAGCTGA

CTTTTTTGCTCTTTCTTTTGGACCAACTTTGAGTTTTCAACTCTTGGACC

CTCATATGAAGTTCCACCAATTAGAATCTCCCAGCCTGAGGCAACTCCTT

TCTTGGATTGACCTTGAATATAACCACCCTCAAATATTTATTGTGGAAAA

-continued

TGGCTGGTTTGTCTCAGGGACCACCAAGAGAGATGATGCCAAATATATGT

ATTACCTCAAAAAATTCATAATGGAAACCTTAAAAGCCATCAGGCTGGAT

GGGGTGGATGTCATAGGATACACAGCGTGGTCCCTTATGGATGGCTTCGA

GTGGCACAGAGGCTACAGCATCAGACGTGGACTCTTCTACGTGGACTTTC

TAAGCCAGGATAAGAAACTGTTGCCAAAGTCTTCAGCCTTGTTCTACCAA

AAGCTGATAGAGAAAAATGGCTTCCCTCCTTTACCTGAAAATCAGCCCCT

AGAAGGGACATTTCCCTGTGACTTTGCTTGGGGAATTGTTGACAACTACA

TTCAAGTGGACACCACTCTGTCTCAGTTTACCGACCCGAACGTTTACCTG

TGGGACGTCCATCACAGCAAGAGGCTGATTAAGGTGGACGGGCTGCGGGC

CAAGAAGAGGAAGCCCTACTGCGTGGACTTTGCCGCCATCGGGCCCCAGG

TGGCCCTGCTGCAGGAGATGCACGTCTCGCATTTTCACTTCTCGCTGGAC

TGGGCCCTGCTCCTGCCGCTGGGCAACCAGTCCCGGGTGAACCACGCGGC

CCTGCACTACTACGGCTGCGTGGCCAGCGAGCTCCTGCGCGCCAACATCA

CCCCGGTGGTGGCGCTCTGGAGACCAGCCGCTGCGCACCAGGGTCTGCCT

GGACCGCTGGCACAGCGCGGTGCCTGGGAGAACCCACGCACCGCCCTGGC

GTTCGCCGAGTACGCGCGCCTGTGCTTCCGCGCCCTGGGCCGCCACGTCA

AGGTGTGGATCACGCTGCGCGAGCCGCCCACGCGGAACCTGACGCTCCGC

GCCGGGCACAACCTGCTGCGGGCGCACGCGCTGGCCTGGCGCGTGTACGA

CGAGCAGTTCCGGGGCTCGCAGCAGGGGAAGGTGTCCATCGCCCTGCAGG

CCGACTGGGTGGAGCCCGCCTGCCCCTCCTCCCAGAAGGACCGCGAAGTG

GCCGAGAGGGTTCTGGAGTTCGACGTCGGCTGGCTGGCCGAGCCCATCTT

CGGCTCCGGGGACTACCCGCGGCTGATGCGCGACTGGCTCACCCGGAGAG

ACCATTCCCTCCTGCCCTATTTCACTGACGAAGAGAAGAGGCTAATCCGG

GGTTCCTTTGACTTCCTGGCCTTGAGCCATTACACCACCATCCTCGTGGA

CTGGGAAAAGGAAGACCCAGTCAAATACAATGATTACCTGGAAGTGCAGG

AGATGACCGACATCACCTGGCTCAACTCCCCCAGTCAGGTGGCCGTAGTG

CCCTGGGGCCTGCGCAAAGTGCTCAACTGGCTCAAGTTCAAGTACGGAGA

CCTCCCCATGTATATCGTATCCAACGGCATAGATGACGATCCGCGGGCAG

CCCAGGACTCGTTGAGGGTGTATTACATGCAGAACTATGTAAATGAAGCT

CTGAAAGCCTACGTATTGGATGGTATCAATCTTTGTGGATACTTTGCCTA

CTCATTTAATGATCGCACAGCTCCGAAGTTTGGCCTCTATCATTATGCTG

CAAACCAGTTTGAGCCCAAACCGTCGGTGAAGCATTACAGGAAAATTATT

GACAACAATGGCTTCCCAGGCCCTGAAACTTTGGGGCGGTTTTGTCCAGA

GGAATTCACCCTGTGCACCGAATGCAGCTTTTTTCACACCCGAAAGTCTT

TACTGGCTTTCATAGCTTTCCTACTTTTTGCTTTTATTATTTCTCTTTCT

CTGATTTTCTACTACTCTAGGAAAGGCAGAAGAAGTTATAAAGGAGGGAG

TGGTGGGTCCGATTACAAAGATCACGATGGGGACTATAAAGATCACGACA

TCGACTATAAGGATGACGATGATAAATGATAG.

According to one aspect, sTGFβ-R2 protein has at least 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity or 99.5% sequence identity or 100% sequence identity to the amino acid sequence of sTGFβR2 receptor protein corresponding to SEQ ID NO: 3 as follows where the sTGFbR2 AA sequence is bolded sequence in the IGG FC domain and MGRGLLRGLWPLHIVLWTRIAST (SEQ ID NO: 8) is the secretion signal:

NNDMMVTDSNGVIKFPQLCKFCDVRSSTCDNQKSCMSNCSITSICEKPHE

VCLAVWRKNDENITLETLCHDPKDTYHGIVLEDAASSKCIMKEKKVLGET

FFMCSCSSDECNDYIIFSEEYATNNPDLLLVIFQPKRENGRVPRPPDCPK

CPAPEMLGGPSVFIFPPKPKDTLLIARTPEVTCVVVDLDPEDPEVQISWF

VDGKQMQTAKTQPREEQFNGTYRVVSVLPIGHQDWLKGKQFTCKVNNKAL

PSPIERTISKARGQAHQPSVYVLPPSREELSKNTVSLTCLIKDFFPPDID

VEWQSNGQQEPESKYRTTPPQLDEDGSYFLYSKLSVDKSRWQRGDTFICA

VMHEALHNHYTQESLSHSPGK.

According to one aspect, the nucleic acid sequence encoding an sTGFβ-R2 protein has at least 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity or 99.5% sequence or 100% sequence identity to the nucleic acid sequence encoding sTGFβ-R2 protein corresponding to SEQ ID NO: 4 as follows:

ATGGGTCGGGGGCTGCTCCGGGGCCTGTGGCCGCTGCATATCGTCCTGTG

GACGCGCATCGCCAGCACGAATAATGACATGATGGTCACTGACAGCAATG

GTGTCATCAAATTTCCACAATTGTGTAAATTTTGTGATGTGAGATCTTCC

ACCTGTGACAACCAGAAATCTTGCATGAGCAACTGCAGCATTACATCCAT

CTGTGAGAAGCCACATGAAGTCTGTCTGGCTGTCTGGAGAAAGAATGATG

AGAACATAACACTAGAGACTCTCTGCCATGACCCCAAGGATACCTACCAT

GGAATTGTTCTCGAAGATGCTGCCTCTTCGAAGTGCATTATGAAAGAAAA

GAAGGTGCTGGGGGAGACTTTCTTTATGTGTTCCTGTAGCTCCGACGAGT

GCAACGACTACATCATCTTCTCTGAAGAATATGCCACCAACAACCCTGAC

TTGTTGTTAGTCATATTCCAACCCAAAAGAGAAAATGGAAGAGTTCCTCG

CCCACCTGATTGTCCCAAATGCCCAGCCCCTGAAATGCTGGGAGGGCCTT

CGGTCTTCATCTTTCCCCCGAAACCCAAGGACACCCTCTTGATTGCCCGA

ACACCTGAGGTCACATGTGTGGTGGTGGATCTGGACCCAGAAGACCCTGA

GGTGCAGATCAGCTGGTTCGTGGACGGTAAGCAGATGCAAACAGCCAAGA

CTCAGCCTCGTGAGGAGCAGTTCAATGGCACCTACCGTGTGGTCAGTGTC

CTCCCCATTGGGCACCAGGACTGGCTCAAGGGGAAGCAGTTCACGTGCAA

AGTCAACAACAAAGCCCTCCCATCCCCGATCGAGAGGACCATCTCCAAGG

CCAGAGGGCAAGCCCATCAGCCCAGTGTGTATGTCCTGCCGCCATCCCGG

GAGGAGTTGAGCAAGAACACAGTCAGCTTGACATGCCTGATCAAAGACTT

-continued

CTTCCCACCTGACATTGATGTGGAGTGGCAGAGCAATGGACAGCAGGAGC

CTGAGAGCAAGTACCGCACGACCCCGCCCCAGCTGGACGAGGACGGGTCC

TACTTCCTGTACAGCAAGCTCTCTGTGGACAAGAGCCGCTGGCAGCGGGG

AGACACCTTCATATGTGCGGTGATGCATGAAGCTCTACACAACCACTACA

CACAGGAATCCCTCTCCCATTCTCCGGGTAAAGGAGGGAGTGGTGGGTCC

GATTACAAAGATCACGATGGGGACTATAAAGATCACGACATCGACTATAA

GGATGACGATGATAAATGA.

According to one aspect, according to one aspect, the sTGFβ-R2 protein and/or the αKlotho protein is an Fc fusion protein including an Ig Fc domain. According to one aspect, the Ig Fc domain is selected from the group consisting of a human, a canine, a feline, a bovine, an ovine, a caprine, an equine, a murine, and a porcine Fc or a subtype thereof, including IgG1, IgG2a, IgG2b, IgG3, and IgG4.

According to one aspect, the Ig Fc domain is a human Ig Fc domain that has at least 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity or 99.5% sequence identity or 100% sequence identity to the amino acid sequence corresponding to SEQ ID NO:5 as follows:

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

According to one aspect, the Ig Fc domain is a mouse Ig Fc domain that has at least 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity or 99.5% sequence identity or 100% sequence identity to the amino acid sequence corresponding to SEQ ID NO:6 as follows:

PRGPTIKPCPPCKCPAPNLEGGPSVFIFPPKIKDVLMISLSPIVTCVVVD

VSEDDPDVQISWFVNNVEVHTAQTQTHREDYNSTLRVVSALPIQHQDWMS

GKAFACAVNNKDLPAPIERTISKPKGSVRAPQVYVLPPPEEEMTKKQVTL

TCMVTDFMPEDIYVEWTNNGKTELNYKNTEPVLDSDGSYFMYSKLRVEKK

NWVERNSYSCSVVHEGLHNHHTTKSFSRTPGK.

According to one aspect, the Ig Fc domain is a dog Ig Fc domain that has at least 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity or 99.5% sequence identity or 100% sequence identity to the amino acid sequence corresponding to SEQ ID NO:7 as follows:

```
PKRENGRVPRPPDCPKCPAPEMLGGPSVFIFPPKPKDTLLIARTPEVTCV

VVDLDPEDPEVQISWFVDGKQMQTAKTQPREEQFNGTYRVVSVLPIGHQD

WLKGKQFTCKVNNKALPSPIERTISKARGQAHQPSVYVLPPSREELSKNT

VSLTCLIKDFFPPDIDVEWQSNGQQEPESKYRTTPPQLDEDGSYFLYSKL

SVDKSRWQRGDTFICAVMHEALHNHYTQESLSHSPGK.
```

According to one aspect, amino acid sequences having the described percent homology to the αKlotho protein amino acid sequence or the sTGFβ-R2 protein amino acid sequence can be determined by obtaining the crystal structure for the αKlotho protein or the sTGFβ-R2 protein and determining the active site or sites responsible for binding or activity and determining percent homology structures which maintain useful binding or activity. Portions of proteins identified as inactive are suitable for amino acid substitution or modification or mutation to produce proteins having the claimed percent homology. Active portions may also be modified or substituted or mutated to the extent that useful binding or activity results. Ig Fc sequences having the desired percent homology can be determined in a similar manner. Methods are known to those of skill in the art to determine protein-bonding sites using X-ray crystallographic identification and include the general methods described in Newcomer et al., PNAS, Vol. 90, pp. 9223-9227 (October 1993) which can be used or modified by one of skill to determine the binding sites for αKlotho protein or the sTGFβ-R2 protein. Software programs such as the following can be used to determine 3D structures, binding pockets, tunnels and channels, surface characteristics and voids, ligand binding sites and the like: MED-SuMO (distributed by MEDIT), TRAPP (Molecular and Cellular Modelling group at Heidelberg Institute for Theoretical Studies, Germany), CAVER (Masaryk University), GHECOM (open source), LIGSITEcsc, SURFNET, SiteHound, ICM-PocketFinder (Molsoft), SiteMap (Schrodinger), MSPocket (open source), POCASA (Hokkaido University), VOIDOO, FunFOLDQA (University of Reading), eFindSite (Louisiana Stata University), SiteEngine (Tel-Aviv University) and SVILP_Ligand (Imperial College London). Useful databases include sc-PDB (University of Strasbourg), CASTp, Pocketome (Encyclopedia of conformational ensembles of all druggable binding sites that can be identified experimentally from co-crystal structures in the Protein Data Bank), PDBe motifs and Sites, LigASite, PROtein SURFace ExploreR, fPOP, PDBSITE (GeneNetworks) and LigBase (UCSF). Useful Web services include 3DLigandSite (Imperial College of London), metaPocket, PockDrug (University Paris-Diderot, France), PocketQuery (University of Pittsburgh), PASS, DEPTH, wwwPDBinder (University of Roma 2, Italy), IsoMIF (University of Sherbrooke, Canada), LISE (Institute of Biomedical Sciences, Academia Sinica), SiteHound-web (Sanchez Lab, Mount Sinai School of Medicine, NY) and MultiBind (Bioinformatics Group, Tel-Aviv University).

Aspects of the present disclosure provide a vector including a first nucleic acid sequence encoding an αKlotho protein or an active fragment thereof and a second nucleic acid sequence encoding a soluble Transforming Growth Factor Beta Receptor II (sTGFβ-R2) protein or an active fragment thereof. According to one aspect, a first promoter is operably linked to the first nucleic acid sequence for expression of the αKlotho protein or an active fragment thereof in a mammalian cell, and a second promoter is operably linked to the second nucleic acid sequence for expression of the sTGFβ-R2 protein or an active fragment thereof in a mammalian cell. According to one aspect, the first promoter and the second promoter are cell or tissue specific. According to one aspect, the first promoter and the second promoter are constitutive or inducible.

The present disclosure provides a pharmaceutical formulation including a vector including a first nucleic acid sequence encoding an αKlotho protein or an active fragment thereof and a second nucleic acid sequence encoding a soluble Transforming Growth Factor Beta Receptor II (sTGFβ-R2) protein or an active fragment thereof in a pharmaceutically acceptable excipient.

The foregoing general description, including the drawings, and the following detailed description are exemplary and explanatory only and are not restrictive of this disclosure.

The section headings used herein are for organizational purposes only and not to be construed as limiting the subject matter described.

In reference to the present disclosure, the technical and scientific terms used in the descriptions herein will have the meanings commonly understood by one of ordinary skill in the art, unless specifically defined otherwise.

As used in this specification and the appended claims, the singular forms "a", "an" and "the" include plural referents unless the context clearly indicates otherwise. Thus, for example, reference to "a protein" includes more than one protein, and reference to "an excipient" includes more than one excipient.

It is further to be understood that use of "or" means "and/or" unless stated otherwise. Similarly, "comprise," "comprises," "comprising" "include," "includes," and "including" are interchangeable and not intended to be limiting. Also, where descriptions of various embodiments use the term "comprising," those skilled in the art would understand that in some specific instances, an embodiment can be alternatively described using language "consisting essentially of" or "consisting of."

"Gene" as used herein refers to a nucleic acid region, also referred to as a transcribed region, which expresses a polynucleotide, such as an RNA. The transcribed polynucleotide can have a sequence encoding a polypeptide, such as a functional protein, which can be translated into the encoded polypeptide when placed under the control of an appropriate regulatory region. A gene may comprise several operably linked fragments, such as a promoter, a 5' leader sequence, a coding sequence and a 3' nontranslated sequence, such as a polyadenylation site. A chimeric or recombinant gene is a gene not normally found in nature, such as a gene in which, for example, the promoter is not associated in nature with part or all of the transcribed DNA region. "Expression of a gene" refers to the process wherein a gene is transcribed into an RNA and/or translated into a functional protein.

"Gene delivery" or "gene transfer" refers to methods for introduction of recombinant or foreign DNA into host cells. The transferred DNA can remain non-integrated or preferably integrates into the genome of the host cell. Gene delivery can take place for example by transduction, using viral vectors, or by transformation of cells, using known methods, such as electroporation, cell bombardment.

"Transgene" refers to a gene that has been introduced into a host cell. The transgene may comprise sequences that are native to the cell, sequences that do not occur naturally in the cell, or combinations thereof. A transgene may contain sequences coding for one or more proteins that may be operably linked to appropriate regulatory sequences for expression of the coding sequences in the cell.

"Transduction" refers to the delivery of a nucleic acid molecule into a recipient host cell, such as by a gene delivery vector, such as rAAV. For example, transduction of a target cell by a rAAV virion leads to transfer of the rAAV vector contained in that virion into the transduced cell. "Host cell" or "target cell" refers to the cell into which the nucleic acid delivery takes place.

"Functional protein" includes variants, mutations, homologues, and functional fragments of the full length proteins. One of skill will readily be able to construct proteins homologous to the full length proteins which retain the activity, in whole or in part, of the full length protein, based on the present disclosure.

"Vector" refers generally to nucleic acid constructs suitable for cloning and expression of nucleotide sequences. One example of a vector is a viral vector. The term vector may also sometimes refer to transport vehicles comprising the vector, such as viruses or virions, which are able to transfer the vector into and between host cells.

"AAV vector" or "rAAV vector" refers to a recombinant vector derived from an adeno-associated virus serotype, such as AAV1, AAV2, AAV3, AAV4, AAV5, AAV6, AAV7, AAV8, AAV9, AAV10, AAV11, AAV12, AAV2.5, AAvDJ, AAVrh10.XX and others. rAAV vectors can have one or preferably all wild type AAV genes deleted, but still comprise functional ITR nucleic acid sequences. Functional ITR sequences are necessary for the replication, rescue and packaging of AAV virions. The ITR sequences may be wild type sequences or substantially identical sequences (as defined below) or may be altered by for example in insertion, mutation, deletion or substitution of nucleotides, as long as they remain functional.

"Therapeutically effective amount" refers to an amount effective, at dosages and for periods of time necessary, to achieve the desired therapeutic result, such as results directed at osteoarthritis and related diseases or conditions. A therapeutically effective amount of a parvoviral virion or pharmaceutical composition may vary according to factors such as the disease state, age, sex, and weight of the individual, and the ability of the parvoviral virion or pharmaceutical composition to elicit a desired response in the individual. Dosage regimens may be adjusted to provide the optimum therapeutic response. A therapeutically effective amount is also typically one in which any toxic or detrimental effects of the parvoviral virion or pharmaceutical composition are outweighed by the therapeutically beneficial effects.

"Prophylactically effective amount" refers to an amount effective, at dosages and for periods of time necessary, to achieve the desired prophylactic result, such as preventing or inhibiting osteoarthritis. A prophylactic dose may be used in subjects prior to or at an earlier stage of disease, and a prophylactically effective amount may be more or less than a therapeutically effective amount in some cases.

"Nucleic acid" includes any molecule composed of or comprising monomeric nucleotides. The term "nucleotide sequence" may be used interchangeably with "nucleic acid" herein. A nucleic acid may be an oligonucleotide or a polynucleotide. A nucleic acid may be a DNA or an RNA. A nucleic acid may be a gene. A nucleic acid may be chemically modified or artificial. Artificial nucleic acids include peptide nucleic acid (PNA), Morpholino and locked nucleic acid (LNA), as well as glycol nucleic acid (GNA) and threose nucleic acid (TNA). Each of these is distinguished from naturally-occurring DNA or RNA by changes to the backbone of the molecule. Also, phosphorothioate nucleotides may be used.

"Nucleic acid construct" is herein understood to mean a man-made nucleic acid molecule resulting from the use of recombinant DNA technology. A nucleic acid construct is a nucleic acid molecule, either single- or double-stranded, which has been modified to contain segments of nucleic acids, which are combined and juxtaposed in a manner, which would not otherwise exist in nature. A nucleic acid construct usually is a "vector", i.e. a nucleic acid molecule which is used to deliver exogenously created DNA into a host cell. One type of nucleic acid construct is an "expression cassette" or "expression vector". These terms refer to nucleotide sequences that are capable of effecting expression of a gene in host cells or host organisms compatible with such sequences. Expression cassettes or expression vectors typically include at least suitable transcription regulatory sequences and optionally, 3' transcription termination signals. Additional factors necessary or helpful in effecting expression may also be present, such as expression enhancer elements. A nucleic acid construct can also be a vector in which it directs expression or repression of a protein by operating as RNA instead of DNA. In the case of increasing expression of a target protein, the nucleic acid construct can be mRNA or similar in which the cell or more specifically the ribosome would recognize and create many copies of the protein. In the case of repressing expression of a target sequence, the RNA can be in the form that acts through preventing the ribosome from creating protein. This can be done through mechanisms of RNAi or shRNA or miRNA or Pri-miRNA. According to certain aspects, repressing a known repressor of a target sequence can result in an increase in the target sequence through repression through the delivery of either mRNA (or similar) or shRNA (or similar) to regulate the target sequence. This can also be done through the vector that provides DNA that is expressed, such as when using AAV.

"Operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signals for introns, 2A peptide sequences (that allow multicistronic expression) and stop codons. According to one aspect, first and second nucleic acid sequences encoding sTGFβ-R2 protein and αKlotho are separated by a polycistronic element. A polycistronic element is generally understood to describe a type of messenger RNA that can encode more than one polypeptide separately within the same RNA molecule. The term "expression control sequence" is intended to include, at a minimum, a sequence whose presence is designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, which may be referred to as polyA sequences. It also can be designed to enhance mRNA stability. Expression control sequences which affect the transcription and translation stability, e.g., promoters, as well as sequences which effect the translation, e.g., Kozak sequences, suitable for use in insect cells are well known to those skilled in the art. Expression control sequences can be of such nature as to modulate the nucleotide sequence to which it is operably linked such that lower expression levels or higher expression levels are achieved.

One can also fuse functional domains to already known proteins. Such is the case where a mitochondrial signal is fused to CAT (catalase) such that the catalase is targeted to be shuttled to the mitochondria and perform its function inside or near the mitochondria instead of its natural location. One can also add targeting signals to other proteins to have them targeted to other parts of the cell or even secreted from the cell. In the case of some proteins a better known version can replace the natural sequence for enhanced effect, such as taking the human or mouse secretion signal for TGFbR2 and fusing it to the dog version of the protein.

"Promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter, including e.g. attenuators or enhancers, but also silencers. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells. The disclosure provides for the operable linking of nucleic acid constructs to a mammalian cell-compatible expression control sequence, e.g., a promoter. Many such promoters are known in the art (see Sambrook and Russell, 2001, supra). Constitutive promoters that are broadly expressed in many cell types, such as the CMV and hEf1α promoter are disclosed. Variations of the full-length hEf1α are also disclosed which are shorter but still provide effective constitutive expression. Disclosed are promoters that are inducible, tissue-specific, cell-type-specific, or cell cycle-specific. In a disclosed embodiment, the nucleotide sequence encoding the porphobilinogen deaminase is operably linked to a liver-specific promoter. Liver-specific promoters are particularly preferred for use in conjunction the non-erythroid deaminase. Preferably, in a construct of the disclosure an expression control sequence for liver-specific expression are e.g. selected from the group consisting of an α1-anti-trypsin (AAT) promoter, a thyroid hormone-binding globulin promoter, an albumin promoter, a thyroxin-binding globulin (TBG) promoter, an Hepatic Control Region (HCR)-ApoCII hybrid promoter, an HCR-hAAT hybrid promoter, an AAT promoter combined with the mouse albumin gene enhancer (Ealb) element and an apolipoprotein E promoter. Other examples include the E2F promoter for tumour-selective, and, in particular, neurological cell tumour-selective expression (Parr et al., (1997) Nat. Med. 3:1145-9) or the IL-2 promoter for use in mononuclear blood cells (Hagenbaugh et al., (1997) J Exp Med; 185: 2101-10).

"3' UTR" or "3' non-translated sequence" (also often referred to as 3' untranslated region, or 3' end) refers to the nucleic acid sequence found downstream of the coding sequence of a gene, which comprises, for example, a transcription termination site and (in most, but not all eukaryotic mRNAs) a polyadenylation signal (such as e.g. AAUAAA or variants thereof). After termination of transcription, the mRNA transcript may be cleaved downstream of the polyadenylation signal and a poly(A) tail may be added, which is involved in the transport of the mRNA to the cytoplasm (where translation takes place).

"Naturally occurring sequence" or "native sequence" as used herein refers to a polynucleotide or amino acid isolated from a naturally occurring source. Included within "native sequence" are recombinant forms of a native polypeptide or polynucleotide which have a sequence identical to the native form.

"Mutant" or "variant" as used herein refers to an amino acid or polynucleotide sequence which has been altered by substitution, insertion, and/or deletion. In some embodiments, a mutant or variant sequence can have increased, decreased, or substantially similar activities or properties in comparison to the parental sequence.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, (1981) Adv. Appl. Math. 2:482, by the homology alignment algorithm of Needleman and Wunsch, (1970) J. Mol. Biol. 48:443, by the search for similarity method of Pearson and Lipman, (1988) Proc. Natl. Acad. Sci. USA 85:2444, by computerized implementations of these algorithms (GAP, BESTFIT, FASTA, and TFASTA), or by visual inspection (see generally, Current Protocols in Molecular Biology, F. M. Ausubel et al., eds., Current Protocols, Greene Publishing Associates, Inc. and John Wiley & Sons, Inc., (1995 Supplement)).

Examples of algorithms that are suitable for determining percent sequence identity and sequence similarity are the BLAST and BLAST 2.0 algorithms, which are described in Altschul et al., (1990), J. Mol. Biol. 215: 403-410 and Altschul et al., (1977) Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, (1989) *Proc. Natl. Acad. Sci. USA* 89:10915).

The degree of percent amino acid sequence identity can also be obtained by ClustalW analysis (version W 1.8) by counting the number of identical matches in the alignment and dividing such number of identical matches by the length of the reference sequence, and using the following default ClustalW parameters to achieve slow/accurate pairwise optimal alignments— Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

"Subject" or "patient" refers to a mammal, such as a non-primate (e.g., cow, pig, horse, cat, dog, rat, etc.) or a primate (e.g., monkey or human). The mammal may be a domesticated animal, such as a dog, a cat, a mouse, a cow, a sheep, a goat, a horse, or a pig. The mammal may be a human subject. In some embodiments, the human is an adult patient. In some embodiments, the human is a pediatric patient.

Delivery of Nucleic Acids Encoding Functional Proteins

Foreign nucleic acids, alternatively referred to as heterologous nucleic acids (i.e., those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources based on the present disclosure. Foreign nucleic acids may be delivered to a subject by administering to the subject, such as systemically administering to the subject, such as by intravenous administration or injection, intra-articular cartilage administration or injection, intraperitoneal administration or injection, intramuscular administration or injection, intracranial administration or injection, intraocular administration or injection, subcutaneous administration or injection, a nucleic acid or vector including a nucleic acid as described herein.

Gene therapy methods and methods of delivering genes to subjects, for example using adeno-associated viruses, are described in U.S. Pat. No. 6,967,018, WO2014/093622, US2008/0175845, US 2014/0100265, EP2432490, EP2352823, EP2384200, WO2014/127198, WO2005/122723, WO2008/137490, WO2013/142114, WO2006/128190, WO2009/134681, EP2341068, WO2008/027084, WO2009/054994, WO2014059031, U.S. Pat. No. 7,977,049 and WO 2014/059029, each of which are incorporated herein by reference in its entirety and in particular for methods describing delivering genes to subjects where described in each patent or patent application.

Vectors

Vectors are contemplated for use with the methods and constructs described herein. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors include, among others, plasmids, lentiviruses, and adeno-associated viruses as is known to those of skill in the art. Vectors include, but are not limited to, nucleic acid molecules that are single-stranded, double stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus, e.g. retroviruses, lentiviruses, replication defective retroviruses, adenoviruses, replication defective adenoviruses, and adeno-associated viruses. Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Methods of non-viral delivery of nucleic acids or native DNA binding protein, native guide RNA or other native species include lipofection, microinjection, biolistics, virosomes, liposomes, immunoliposomes, polycation or lipid: nucleic acid conjugates, naked DNA, artificial virions, and agent-enhanced uptake of DNA. Lipofection is described in, e.g., U.S. Pat. Nos. 5,049,386, 4,946,787; and 4,897,355, incorporated herein by reference. Lipofection reagents are also available from commercial sources (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g., in vitro or ex vivo administration) or target tissues (e.g. in vivo administration). The term native includes the protein, enzyme or guide RNA species itself and not the nucleic acid encoding the species.

In some embodiments, the gene therapy vectors for use in the methods herein are parvoviral vectors, such as animal parvoviruses, in particular dependoviruses such as infectious human or simian adeno-associated virus (AAV), and the components thereof (e.g., an animal parvovirus genome) for use as vectors for introduction and/or expression of the nucleotide sequences encoding a porphobilinogen deaminase in mammalian cells. Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth 1. Berns, "Parvoviridae: The Viruses and Their Replication," Chapter 69 in Fields Virology (3d Ed. 1996). For convenience the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, –2 and –3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild-type (wt) AAV infection in mammalian cells the Rep genes (i.e., Rep78 and Rep52) are expressed from the P5 promoter and the P19 promoter, respectively and both Rep proteins have a function in the replication of the viral genome. A splicing event in the Rep ORF results in the expression of actually four Rep proteins (i.e., Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

A "recombinant parvoviral" or "AAV vector" or "rAAV vector" herein refers to a vector comprising one or more polynucleotide sequences of interest, genes of interest or "transgenes" that are flanked by at least one parvoviral or AAV inverted terminal repeat sequences (ITRs). Such rAAV vectors can be replicated and packaged into infectious viral particles when present in an insect host cell that is expressing AAV rep and cap gene products (i.e., AAV Rep and Cap proteins). When an rAAV vector is incorporated into a larger nucleic acid construct (e.g. in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions. Thus, in a further aspect the invention relates to a nucleic acid construct comprising a nucleotide sequence encoding a porphobilinogen deaminase as herein defined above, wherein the nucleic acid construct is a recombinant parvoviral or AAV vector and thus comprises at least one parvoviral or AAV ITR. Preferably, in the nucleic acid construct the nucleotide sequence encoding the porphobilinogen deaminase is flanked by parvoviral or AAV ITRs on either side.

AAV is able to infect a number of mammalian cells. See, e.g., Tratschin et al., (1985) *Mol. Cell Biol.* 5:3251-3260) and Grimm et al., (1999) *Hum. Gene Ther.* 10:2445-2450). However, AAV transduction of human synovial fibroblasts is significantly more efficient than in similar murine cells, (Jennings et al., (2001) Arthritis Res, 3:1), and the cellular tropicity of AAV differs among serotypes. See, e.g., Davidson et al. (2000) *Proc. Natl. Acad. Sci. USA,* 97:3428-3432), which discuss differences among AAV2, AAV4, and AAV5 with respect to mammalian CNS cell tropism and transduction efficiency; Goncalves, (2005) *Virol J.* 2(1):43, which discusses approaches to modification of AAV tropism. In some embodiments, for transduction of liver cells rAAV virions with AAV1, AAV8 and AAV5 capsid proteins are preferred (Nathwani et al., (2007) *Blood* 109(4):1414-1421; Kitajima et al., (2006) *Atherosclerosis* 186(1):65-73), of which is rAAV virions with AAV5 capsid proteins may be most preferred.

AAVs are highly prevalent within the human population. See Gao, G., et al., (2004) *J Virol.* 78(12):6381-8; and Boutin, S., et al., (2010) *Hum Gene Ther.* 21(6):704-12) and are useful as viral vectors. Many serotypes exist, each with different tropism for tissue types, See Zincarelli, C., et al., (2008) *Mol Ther.* 16(6):1073-80), which allows specific tissues to be preferentially targeted with appropriate pseudotyping. Some serotypes, such as serotypes 8, 9, and rh10, transduce the mammalian body. See Zincarelli, C., et al., (2008) *Mol Ther.* 16(6):1073-80, Inagaki, K., et al., (2006) *Mol Ther.* 14(1):45-53; Keeler, A. M., et al., (2012) Mol Ther. 20(6):1131-8; Gray, S. J. et al., (2011) Mol Ther. 19(6):1058-69; Okada, H., et al., (2013) *Mol Ther Nucleic Acids.* 2:e95; and Foust, K. D., et al., (2009) *Nat Biotechnol.*

27(1):59-65. AAV9 has been demonstrated to cross the blood-brain barrier. See Foust, K. D., et al., (2009) *Nat Biotechnol.* 27(1):59-65; and Rahim, A. A. et al., (2011) *FASEB J.* 25(10):3505-18) that is inaccessible to many viral vectors and biologics. Certain AAVs have a payload of 4.7-5.0 kb, including viral inverted terminal repeats (ITRs), which are required in cis for viral packaging). See Wu, Z. et al., (2010) Mol Ther. 18(1):80-6; and Dong, J. Y. et al., (1996) *Hum Gene Ther.* 7(17):2101-12; all publications incorporated herein by reference.

The AAV VP proteins are known to determine the cellular tropicity of the AAV virion. The VP protein-encoding sequences are significantly less conserved than Rep proteins and genes among different AAV scrotypes. The ability of Rep and ITR sequences to cross-complement corresponding sequences of other serotypes allows for the production of pseudotyped rAAV particles comprising the capsid proteins of one serotype (e.g., AAV5) and the Rep and/or ITR sequences of another AAV serotype (e.g., AAV2). Such pseudotyped rAAV particles are a part of the present invention. Herein, a pseudotyped rAAV particle may be referred to as being of the type "x/y", where "x" indicates the source of ITRs and "y" indicates the serotype of capsid, for example a ⅔ rAAV particle has ITRs from AAV2 and a capsid from AAV5. Modified "AAV" sequences also can be used in the context of the present disclosure, e.g. for the production of rAAV vectors in insect cells. Such modified sequences e.g. include sequences having at least about 70%, at least about 75%, at least about 80%, at least about 85%, at least about 90%, at least about 95%, or more nucleotide and/or amino acid sequence identity (e.g., a sequence having from about 75% to about 99% nucleotide sequence identity) to an AAV1, AAV2, AAV3, AAV4, AAV5, AAV6, AAV7, AAV8, AAV9, AAV 10, AAV11, AAV12, AAV2.5, AAvDJ, AAVrh10.XX ITR, Rep, or VP can be used in place of wild-type AAV ITR, Rep, or VP sequences. Preferred adenoviral vectors are modified to reduce the host response. See, e.g., Russell (2000) *J. Gen. Virol.* 81:2573-2604; US patent publication no. 20080008690; and Zaldumbide et al. (2008) *Gene Therapy* 15(4):239-46; all publications incorporated herein by reference.

Regulatory Elements and Terminators

Regulatory elements are contemplated for use with the gene therapy vector constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, *Gene Expression Technology: Methods in Enzymology* 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer; see, e.g., Boshart et al, (1985) *Cell* 41:521-530) the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Takebe, Y. (1988) *Mol. Cell. Biol.* 8(1):466-472); SV40 enhancer; and the intron sequence between exons 2 and 3 of rabbit β-globin (O'Hare K. et al., (1981) *Proc. Natl. Acad. Sci. USA.* 78(3):1527-31). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

Administration, Dosage and Treatment

In various embodiments, the one or more gene delivery vectors, including viral vectors, and packaged viral particles containing the viral vectors, can be in the form of a medicament or a pharmaceutical composition and may be used in the manufacture of a medicament or a pharmaceutical composition. The pharmaceutical composition may include a pharmaceutically acceptable carrier. Preferably, the carrier is suitable for parenteral administration. In particular embodiments, the carrier is suitable for intravenous, intra-articular, intraperitoneal or intramuscular administration. Pharmaceutically acceptable carrier or excipients are described in, for example, *Remington: The Science and Practice of Pharmacy*, Alfonso R. Gennaro (Editor) Publishing Company (1997). Exemplary pharmaceutical forms can be in combination with sterile saline, dextrose solution, or buffered solution, or other pharmaceutically acceptable sterile fluids. Alternatively, a solid carrier, may be used such as, for example, microcarrier beads.

Pharmaceutical compositions are typically sterile and stable under the conditions of manufacture and storage. Pharmaceutical compositions may be formulated as a solution, microemulsion, liposome, or other ordered structure suitable to delivery of the gene therapy vectors. The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. The vectors of the present disclosure may be administered in a time or controlled release formulation, for example in a composition which includes a slow release polymer or other carriers that will protect the compound against rapid release, including implants and microencapsulated delivery systems. Biodegradable, biocompatible polymers may for example be used, such as ethylene vinyl acetate, polyanhydridcs, polyglycolic acid, collagen, polyorthoesters, polylactic acid and polylactic, polyglycolic copolymers (PLG).

In some embodiments, the gene therapy vectors, formulated with any acceptable carriers, can be administered parenterally, such as by intravenous, intra-articular, intraperitoneal, subcutaneous, intramuscular administration, limb perfusion or combinations thereof. The administration can be systemic, such that the gene delivery vectors are delivered through the body of the subject. In some embodiments, the gene delivery vectors can be administered directly into the targeted tissue. In some embodiments, the gene delivery vectors can be administered locally, such as by a catheter. The route of administration can be determined by the person of skill in the art, taking into consideration, for example, the nature of target tissue, gene delivery vectors, intended therapeutic effect, and maximum load that can be administered and absorbed by the targeted tissue(s).

Generally, an effective amount, particularly a therapeutically effective amount, of the gene delivery vectors are administered to a subject in need thereof. A "therapeutically effective amount" refers to an amount effective, at dosages and for periods of time necessary, to achieve the desired therapeutic result, such as treatment or amelioration of osteoarthritis. An effective or therapeutically effective amount of vector may vary according to factors such as the disease state, age, sex, and weight of the individual, and the ability of the viral vector to elicit a desired response in the individual. Dosage regimens may be adjusted to provide the optimum therapeutic response.

In particular embodiments, a range for therapeutically or prophylactically effective amounts of a nucleic acid, nucleic acid construct, parvoviral virion or pharmaceutical composition may be from $1 \times 10^{11}$ and $1 \times 10^{14}$ genome copy (gc)/kg or $1 \times 10^{12}$ and $1 \times 10^{13}$ genome copy (gc)/kg. It is to be noted that dosage values may vary with the severity of the condition to be alleviated. The dosage may also vary based on the efficacy of the virion employed. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners.

The tissue target may be specific, for example the articular cartilage associated with osteoarthritis. In some embodiments, the effective dose range for small animals (mice), may be between $1 \times 10^{12}$ and $1 \times 10^{13}$ genome copy (gc)/kg, and for larger animals (cats or dogs) and for human subjects, between $1 \times 10^{11}$ and $1 \times 10^{12}$ gc/kg, or between $1 \times 10^{11}$ and $1 \times 10^{14}$ genome copy (gc)/kg.

In various embodiments, the gene delivery vectors can be administered as a bolus or by continuous infusion over time. In some embodiments, several divided doses can be administered over time or the dose may be proportionally reduced or increased as indicated by the exigencies of the therapeutic situation. In some embodiments, the gene delivery vectors can be administered daily, weekly, biweekly or monthly. The duration of treatment can be for at least one week, one month, 2 months, 3 months, 6 months, or 8 month or more. In some embodiments, the duration of treatment can be for up to 1 year or more, 2 years or more, 3 years or more or indefinitely.

In some embodiments, a therapeutically effective amount of αKlotho protein or an active fragment thereof and sTGFβ-R2 protein or an active fragment thereof is administered to the subject to treat osteoarthritis, such as exhibited by articular cartilage. Methods described herein treats or prevents disorders associated with osteoarthritis or symptoms of osteoarthritis or otherwise improves recovering of articular cartilage structure and function. The amelioration of osteoarthritis provided by the administration of αKlotho protein or an active fragment thereof and sTGFβ-R2 protein or an active fragment thereof directly or through a gene therapy method as described herein is characterized by a reduction of symptoms in a subject compared to an untreated subject. In a further aspect, a gene therapy method or the use of a nucleic acid vector as described above is provided for use in the treatment or prevention in a subject of osteoarthritis. According to one aspect, the administration of αKlotho and sTGFβR2 cooperatively inhibits or prevents osteoarthritis progression such as by downregulating the immune response and promoting joint tissue homeostasis and repair.

Example I

Progression of Osteoarthritis Related-Histoloical Changes in a Rat Model

The present disclosure provides for an animal model of osteoarthritis for use in experiments described herein. Osteoarthritis was mimicked by the intra-articular injection of papain, a chemically induced model that promotes proteoglycans degradation disrupting cartilage micro-architecture and affecting the integrity of the knee joints (see Pritzker K P. Animal models for osteoarthritis: processes, problems and prospects. Ann Rheum Dis. 1994 June; 53(6): 406-20). This enzyme does not have a direct impact on collagen and chondrocytes; thereby, it does not impair the regeneration mechanisms of the cartilage that may be promoted by tested treatments. The model recapitulated several osteoarthritis phenotypes associated with the pathology in animals and humans. For instance, the loss of ECM homeostasis caused by proteoglycan-degrading enzymes such as the MMP13 is one of the main pathological features described in OA patients (see Troeberg L, Nagase H. Proteases involved in cartilage matrix degradation in osteoarthritis. Biochim Biophys Acta. 2011 Jul. 8; 1824(1):133-45).

Rat knee joint was analyzed four weeks after the papain injection. The safranin-O staining showed clear signs of early-stages of osteoarthritis according to the normalized Osteoarthritis Research Society International (OARSI) scores (see Pritzker K P H, Gay S, Jimenez S A, Ostergaard K, Pelletier J-P, Revell P A, et al. Osteoarthritis cartilage histopathology: grading and staging. Osteoarthr Cartil. 2006 January; 14(1):13-29). As a result of the papain treatment, analysis not only showed the presence of MMP13 within the ECM, but also a partial destruction of the cartilage structure.

Figure 1B:
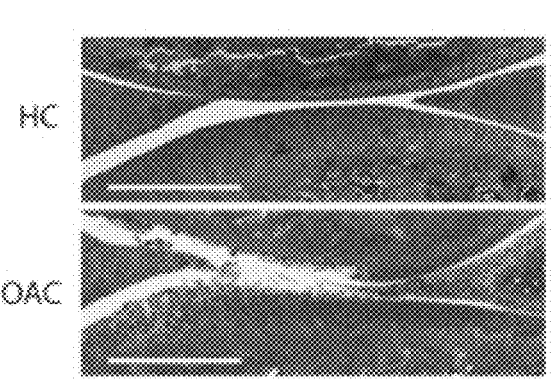
Figure 1C:
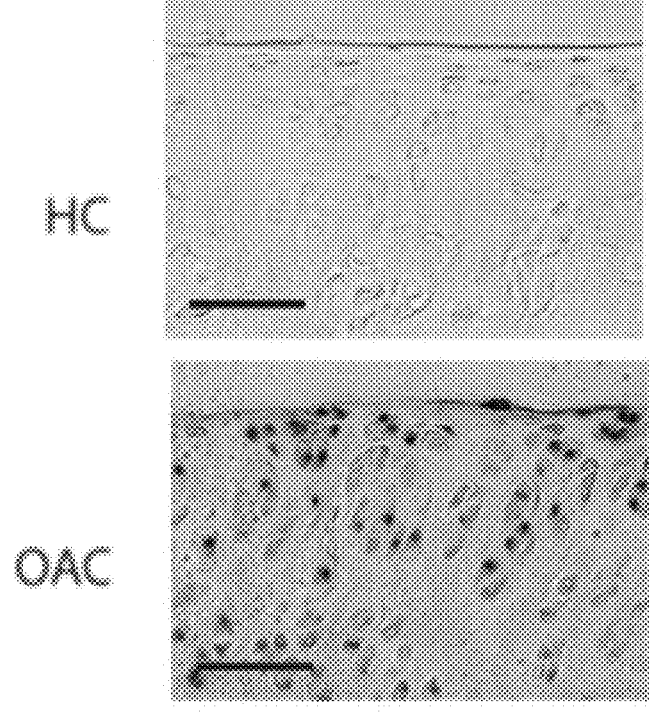
Figure 1D:
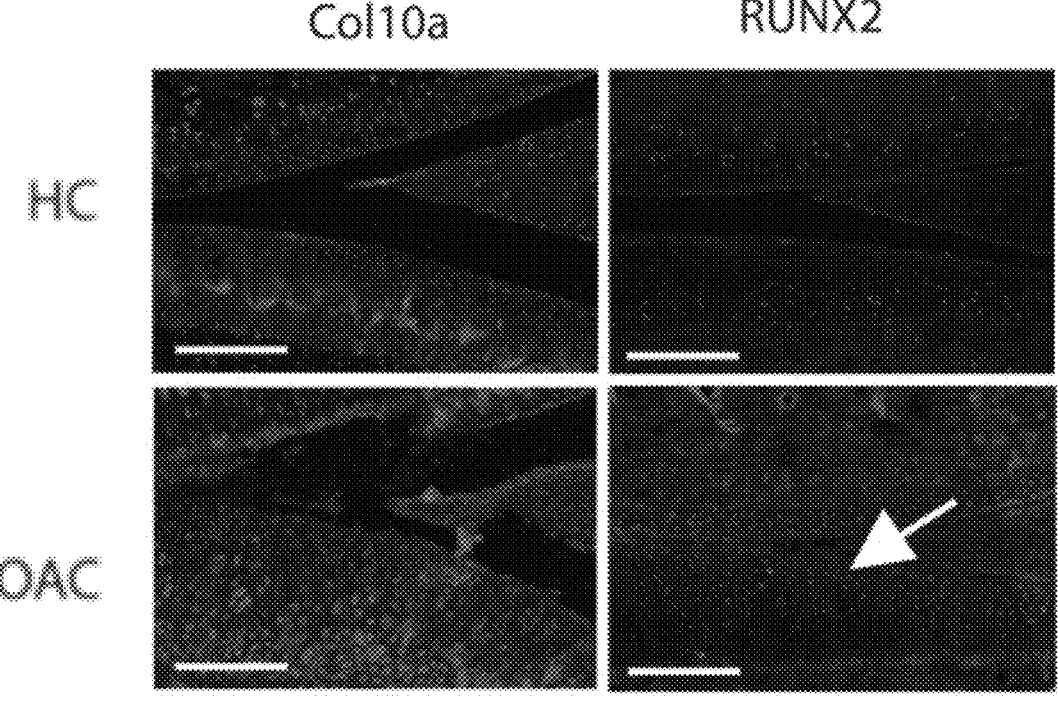
Figure 1E:
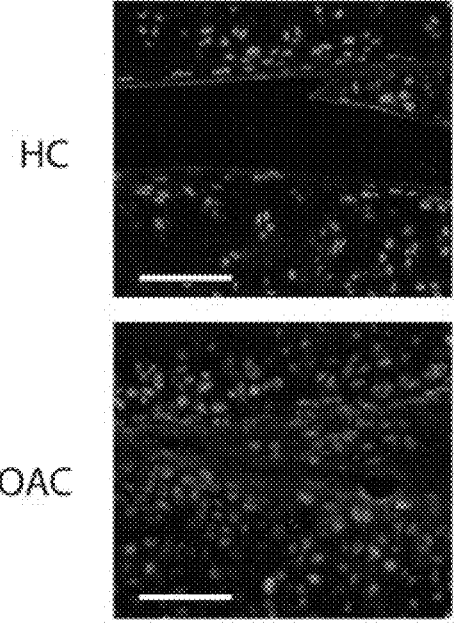
Figure 1F:
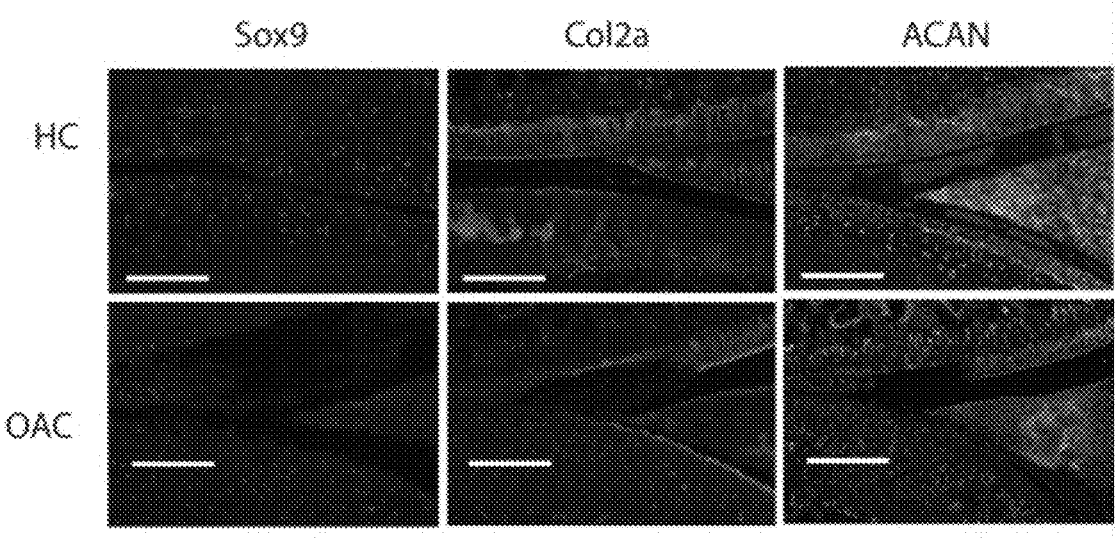
Figure 2A:
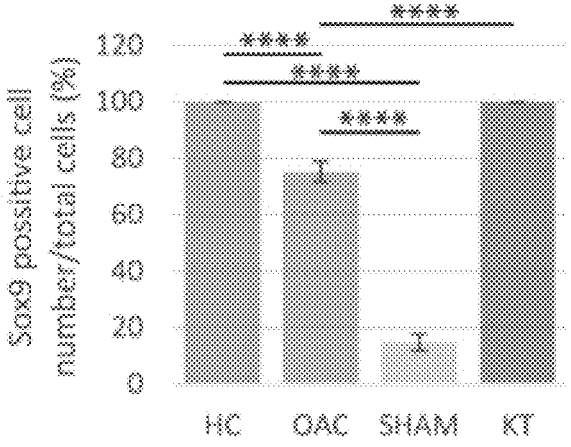
FIGS. 2A-2C depict results of in vivo sTGFβR2 and αKlotho treatment inhibiting chondrocytes hypertrophy and promoting chondrocytes marker upregulation.
Figure 2A:
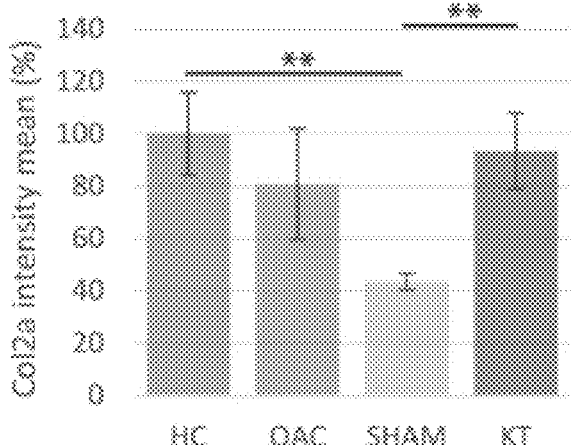
Figure 2A:
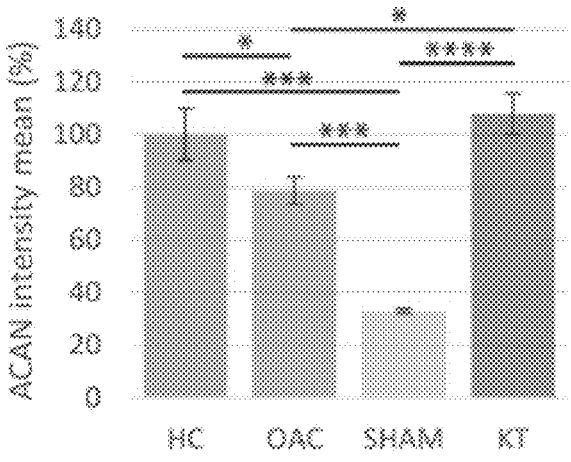

The rats (here on, Osteoarthritis Control group, OAC) showed a grade 2 osteoarthritis (see FIG. 1A) as defined by the parameters analyzed. The safranin-O staining showed diminished cartilage thickness with discontinued fibrillar surface and cellular clusters within the cartilage (see FIG. 1B). The osteoarthritis grade in these samples was further supported by tunel and immunostaining analysis that demonstrated not only the presence of cellular death (see FIG. 1C), but also of hypertrophic chondrocytes within the joint according to higher levels of Col10a and Runx2 (see FIG. 1D) together with the downregulation of the chondrocyte marker Sox9 (see FIG. 1F and FIG. 2A).

Col10a and Runx2 are well known bone markers, which when found in chondrocytes refer to the calcification of the extracellular matrix (ECM) (see Chen D, Shen J, Zhao W, Wang T, Han L, L Hamilton J, et al. Osteoarthritis: toward a comprehensive understanding of pathological mechanism. Bone Research. 2017 Jan. 17). Also, the presence of proteolytic enzymes such as MMP13 within the matrix indicates cartilage damage and loss of joint function (see Xie Y, Mustafa A, Yerzhan A, Merzhakupova D, Yerlan P, N Orakov A, et al. Nuclear matrix metalloproteinases: functions resemble the evolution from the intracellular to the extracellular compartment. Cell Death Discov. 2017 Aug. 14; 3:17036). As a result, aggrecan (ACAN) and collagen type II (Col2a) stainings (see FIG. 1F and FIG. 2A) showed a clear unbalance regarding the content of both matrix components within the cartilage when compared to non-papain treated healthy knees (here on, Healthy Control group, HC). These results demonstrate that osteoarthritis developed in rats four weeks after papain treatment.

Example II

Intra-Articular Injection Using AAV-DJ Virus Serotype

To test the combined effect of αKlotho and sTGFβR2 on osteoarthritis progression and repair, these soluble factors were injected directly into the knee joint in the form of an AAV vector mediated gene therapy. It is to be understood that each factor or active fragment thereof may be encoded by a separate nucleic acid and be provided in a separate vector or each factor may be encoded by a single nucleic acid and be provided in a single vector. The single nucleic acid may be expressed to produce separate soluble factors or may be expressed as a fusion protein of the soluble factors.

It is to be understood that aspects of the present disclosure contemplate directly injecting or otherwise delivering or administering the soluble factors αKlotho (or an active fragment thereof) and sTGFβR2 (or an active fragment thereof) to a patient in need of treatment. The αKlotho (or an active fragment thereof) and sTGFβR2 (or an active fragment thereof) can be administered separately in formulations, such as one after the other in series or can be administered together, such as co-administered in the same formulation. It is to be understood that aspects of the present disclosure contemplate directly injecting or otherwise delivering or administering nucleic acids encoding the soluble factors αKlotho (or an active fragment thereof) and sTGFβR2 (or an active fragment thereof), such as nucleic acids within a vector such as an AAV described herein as gene therapy, to a patient in need of treatment. The nucleic acid encoding αKlotho (or an active fragment thereof) and the nucleic acid encoding sTGFβR2 (or an active fragment thereof) can be administered separately in separately formulations, such as one after the other in series or can be administered together, such as co-administered in the same formulation.

According to certain aspects, the dosage of αKlotho (or an active fragment thereof) and sTGFβR2 (or an active fragment thereof) is in the range of $1 \times 10^{12}$ to $100 \times 10^{12}$ GC (AAV-DJ). An exemplary dose of $2.5 \times 10^{12}$ GC (AAV-DJ) can be injected at the desired site such as the knee in 50 μl of PBS, thereby providing a method of localized injection.

Figure 3A:
Figure 3B:
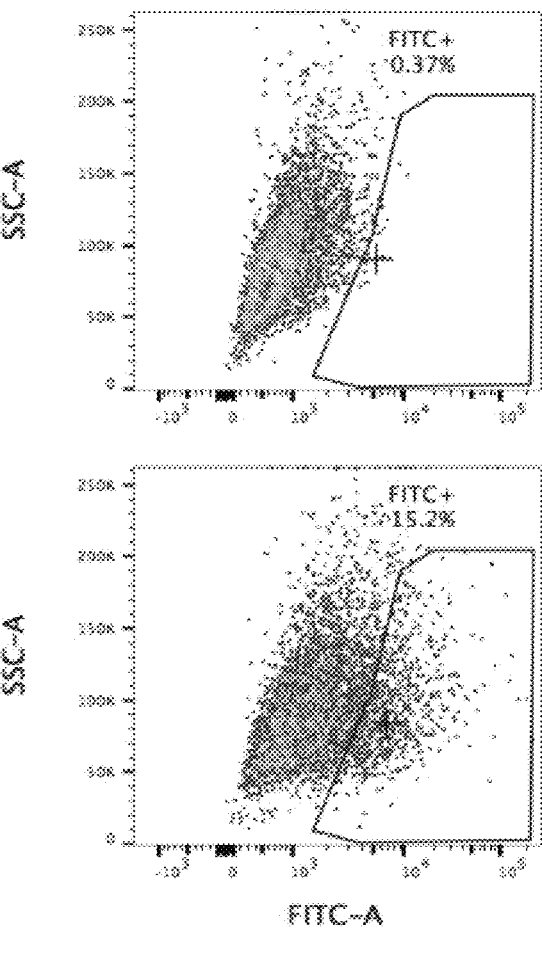
Figure 3C:
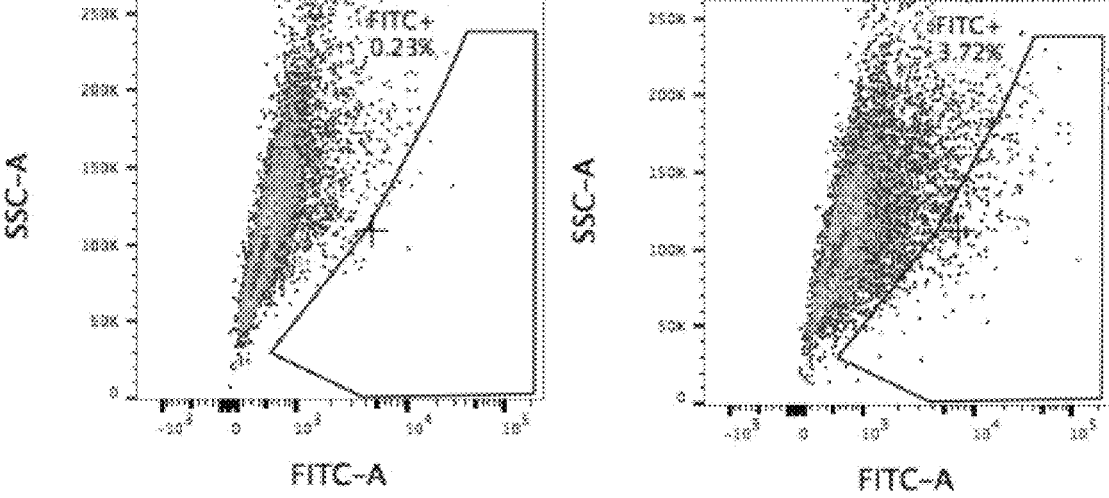
FIG. 3C depicts in situ cell death representative images (HC, n=3; OAC). Blue colored cells represent apoptotic cells. Scale bars, 20 μm. The images show higher number of blue colored cells in the OAC group.

An intra-articular injection of AAV-DJ-Luciferase was first performed to test the safety of the procedure. According to the luciferase readout, the intra-articular injection allowed the injection to restrict the AAV infection to the knee joint without entering the blood stream and avoiding the affection of other tissues (see FIG. 3A), which would help avoid causing side effects. To test the infection efficacy of the AAV-DJ serotype, an in vitro analysis using AAD-DJ-GFP in vitro was first performed. The results analyzed by flow cytometry showed significantly higher efficiency in synovial mesenchymal cells when compared to chondrocytes (see FIGS. 3B and 3C), although both populations were transduced. The higher efficacy of infection of mesenchymal stem cells would help in avoiding any detrimental cellular effects on the chondrocytes as a result of a direct AAV infection (see Hermanns J, SCHULZE A, RR PJ-D, KLEINSCHMIDT JA, SCHMIDT R, HAUSEN HZ. Infection of Primary Cells by Adeno-Associated Virus Type 2 Results in a Modulation of Cell Cycle-Regulating Proteins. J Virol. 1997; 71:8; Raj K, Ogston P, Beard P. Virus-mediated killing of cells that lack p53 activity. Nature. 2001 August; 412 (6850):914-7; Yang G S, Schmidt M, Yan Z, Lindbloom J D, Harding T C, Donahue B A, et al. Virus-Mediated Transduction of Murine Retina with Adeno-Associated Virus: Effects of Viral Capsid and Genome Size. J Virol. 2002 August; 76 (15): 7651-60). According to one aspect, both αKlotho and sTGFβR2 will be released by adjacent mesenchymal cells localized in the joint, exerting their effect in the whole joint.

Figure 2B:
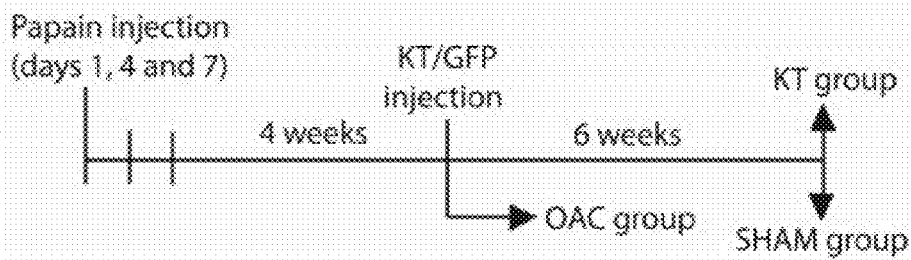

Example III

αKlotho and sTGFβR2 Ameliorates the Clinical Score in Osteoarthritic Rats by Preventing and Reversing the Osteoarthritic Phenotype In order to test the possible effectiveness of αKlotho and sTGFβR2 in cartilage repair, rats treated with papain were allowed to develop early-stage osteoarthritis during four weeks and then were treated by intra-articular injection with either AAV-DJ-GFP (SHAM group) or AAV-DJ-αKlotho and -sTGFβR2 (here on, KT group) (schematic representation can be found in FIG. 2B).

Figure 2C:
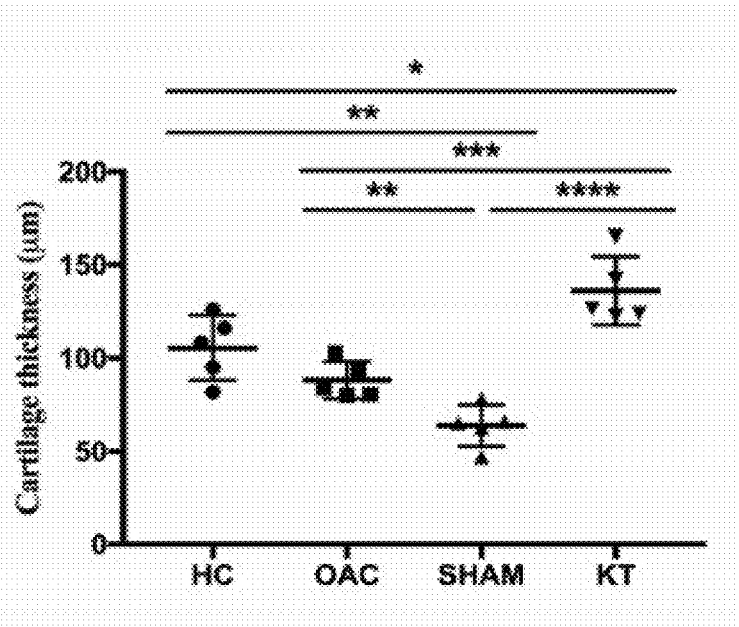
Figure 4A:
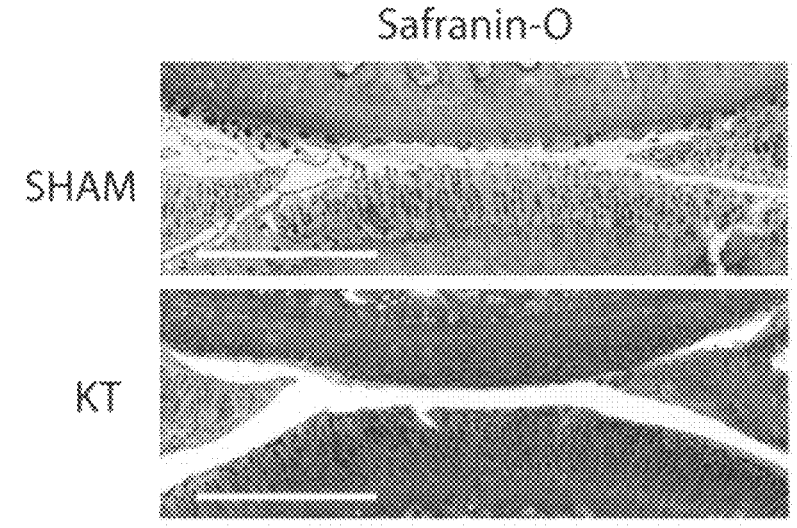
FIGS. 4A-4F depict images that show sTGFβR2 and αKlotho intra-articular injection promotes ECM repair and avoids apoptosis.
Figure 4B:
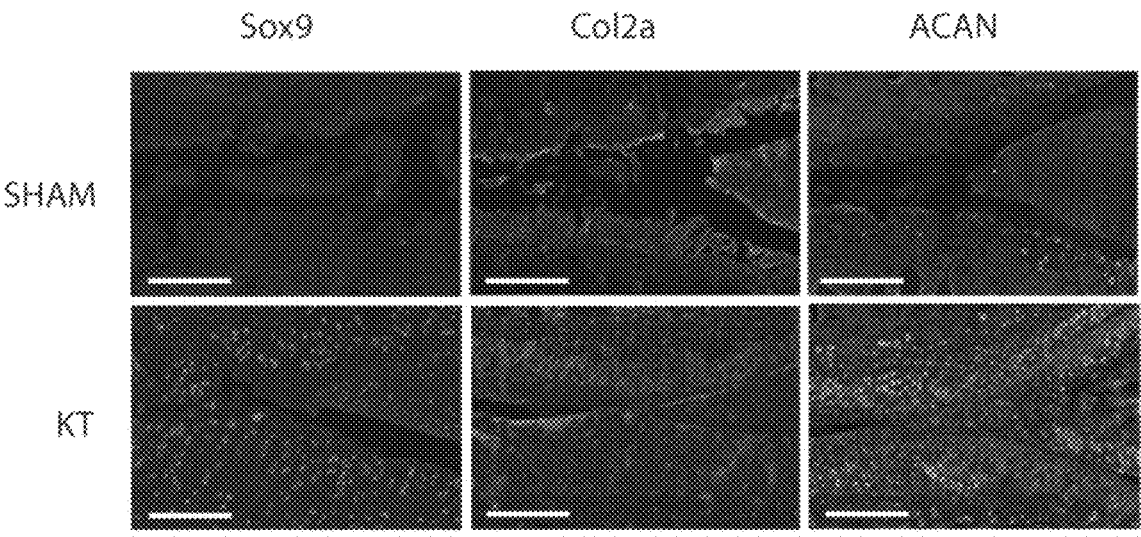
Figure 4C:
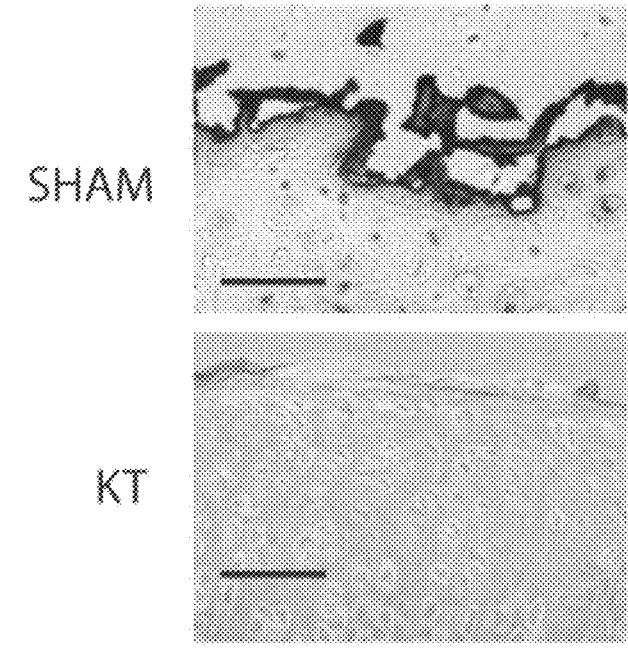
Figure 4D:
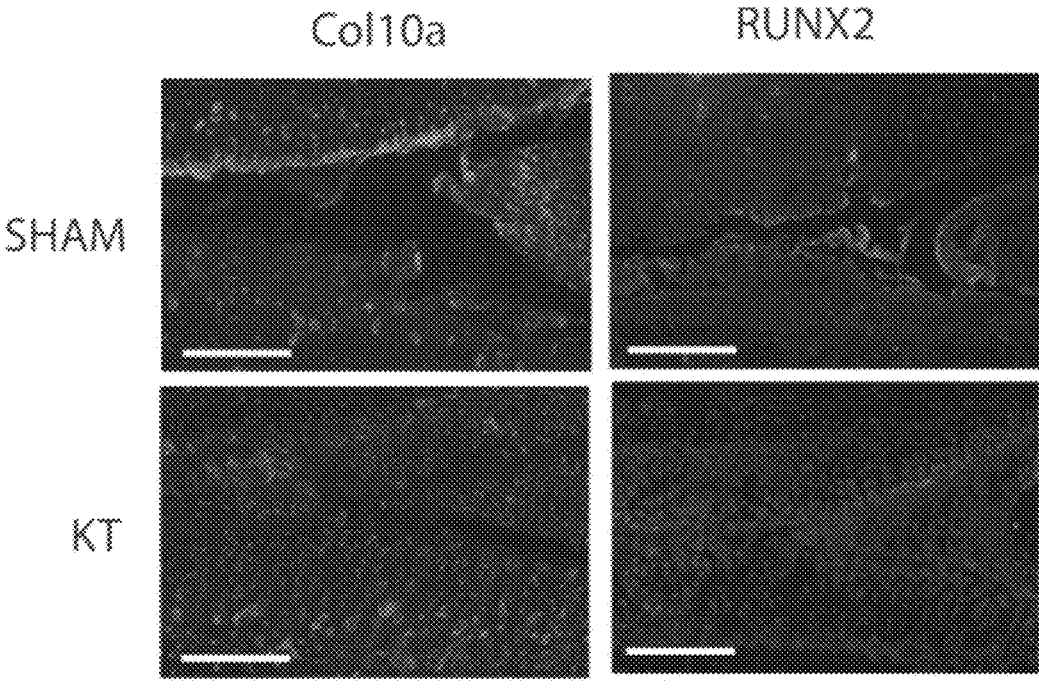
Figure 4E:
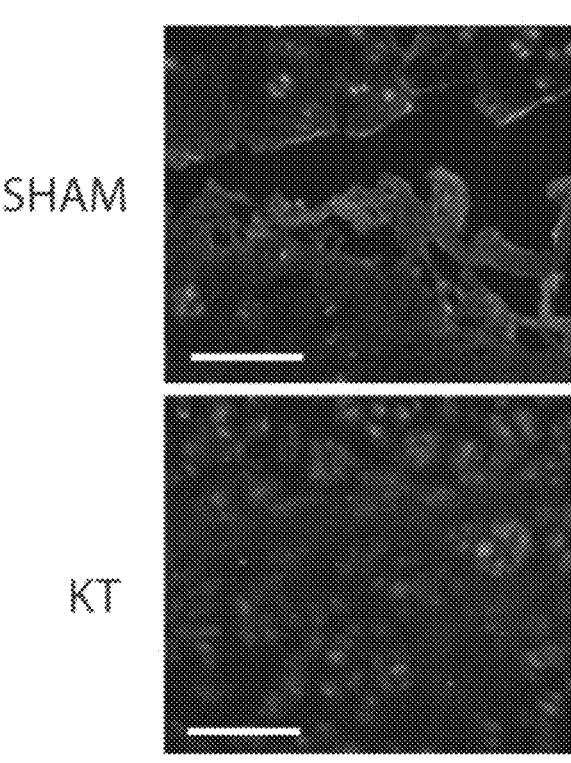
Figure 4F:
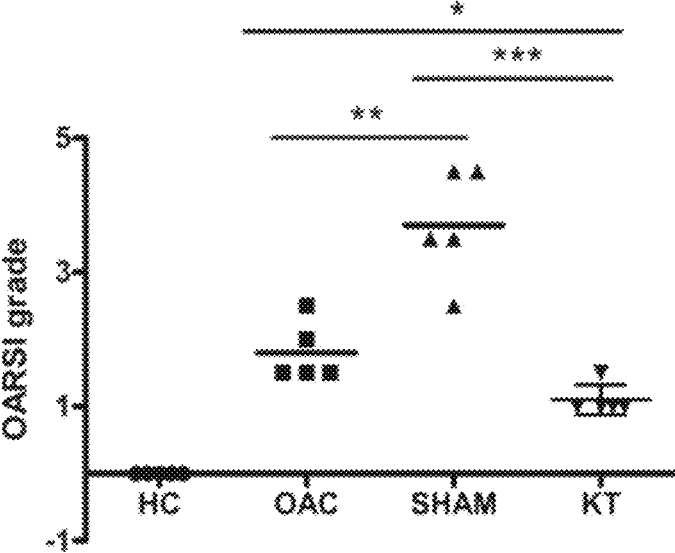

The rats injected with AAV-DJ-GFP showed an even greater deterioration of their cartilage six weeks later. The safranin-O, Col2a and ACAN staining showed not only a clear erosion and loss of the cartilage structure but also a calcification of the matrix, as demonstrated by the drastic down regulation of the ECM components in the remaining fragments (see FIGS. 4A and 4B, and FIG. 2A). The immunohistological analysis showed a drastic decrease in the number of Sox9+ cells (see FIG. 4B and FIG. 2A) while apoptotic cells (see FIG. 4C), hypertrophic markers (see FIG. 4D) and MMP13 (see FIG. 4E) were still found in the remaining cartilage segments. As a result, the thickness of the cartilage was dramatically reduced (see FIG. 2C) (i.e., cartilage thinning as a symptom of osteoarthritis) and the OARSI score analysis classified the injury as grade 4 (see FIG. 4F), indicating a clear progression into osteoarthritis pathology.

The rats treated with AAV-DJ-αKlotho and -sTGFβR2 showed a greatly improved phenotype after 6 weeks. Separate vectors were used to make separate AAV-DJ viruses. A total of $2.5 \times 10^{12}$ GC were injected in the joint, 50% sTGFβR2 and 50% αKlotho. The intra-articular injection of AAV expressing αKlotho and sTGFβR2 not only avoided the release of MMP13 to the ECM, but also promoted the maintenance of the cartilage thickness. When compared to the OAC group, the safranin-O staining (see FIG. 4A) showed recovery of the cartilage thickness (see FIG. 2C) and structure. First, the superficial zone, where the cells are arranged in horizontal clusters parallel to the articular surface, organized in strings, pairs and single cells. Second, the middle and deep zones containing double or multiple chondrocytes arranged in vertical columns. Col2a and ACAN positive staining supports chondrocytes functional recovery with regeneration of the ECM components within the joint (see FIG. 1B and FIG. 2A). The inhibition by αKlotho of ECM degradation supports the increase of Col2a, ACAN and Safranin-O staining after KT treatment. This was further assessed in tissue section analysis. The data not only shows a complete absence of apoptotic cells within the joint (see FIG. 4C), but also the restoration of the hypertrophic markers distribution. Contrary to OAC and SHAM groups, in the KT treated joints, Col10a and Runx2 positive cells are mostly located in the lower levels of the cartilage layer corresponding to the regular hypertrophic layer of the cartilage, similar to HC group (see FIG. 4D). Also, the absence of the proteolytic enzyme MMP13 was found within the ECM in HC and KT treated knees (see FIG. 4E). Based on the drastic articular joint improvement, the OARSI classification indicates that the rats treated with αKlotho and sTGFβR2 recovered from a grade 2 to grade 1 osteoarthritis, while those treated with AAV-DJ-GFP progressed further to grade 4 osteoarthritis (see FIG. 4F).

TGF-β/Smad signaling also contributes to osteoarthritis development and progression (see Shen J, Li S, Chen D. TGF-β signaling and the development of osteoarthritis. Bone Research. 2014 May 27; 2:14002). Chondrocyte hypertrophy is promoted by either an increase in ALK1/ALK5 receptors ratio during aging or a long exposure to TGF-01, indicating the importance of maintaining a balanced TGFβ pathway. Therefore, the high affinity of TGFβR2 receptor towards TGFβ1 and TGFβ3 inhibits chondrocyte hypertrophy and downregulates hypertrophic markers after KT treatment.

According to one aspect, the use of both αKlotho and sTGFβR2 contributes to ECM recovery, for example, by balancing anabolic and catabolic pathways. The TGFβ1 pathway is considered a reparative mediator by stimulating chondrocyte proliferation. According to one aspect, the use of sTGFβR2 to sequester TGFβ1 reduces the catabolic pathways while enhancing its anabolic effects.

Example IV

αKlotho and sTGFβR2 Ameliorates the Inflammatory Response Characteristic of the Osteoarthritic Phenotype In spite of being initially classified as a non-inflammatory arthritis, osteoarthritis is characterized by synovial inflammation (see Scanzello C R, Goldring S R. The role of synovitis in osteoarthritis pathogenesis. Bone. 2012 August;

51(2):249-57). Inflammation precedes significant cartilage loss and joint space narrowing of osteoarthritic joints (Sokolove J, Lepus CM. Role of inflammation in the pathogenesis of osteoarthritis: latest findings and interpretations. Ther Adv Musculoskelet Dis. 2013 April; 5(2):77-94).

Figure 5A:
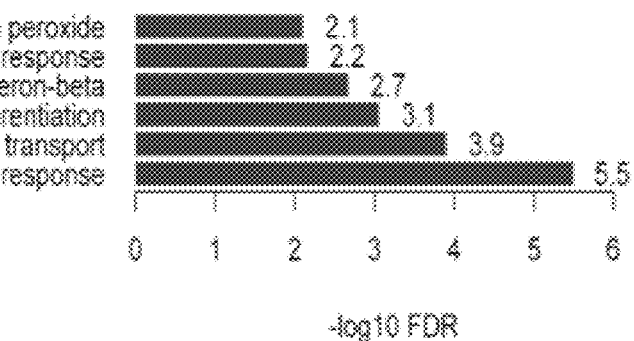
FIGS. 5A-5E depict results of sTGFβR2 and αKlotho inhibiting osteoarthritis-related immune response in vivo.
Figure 5B:
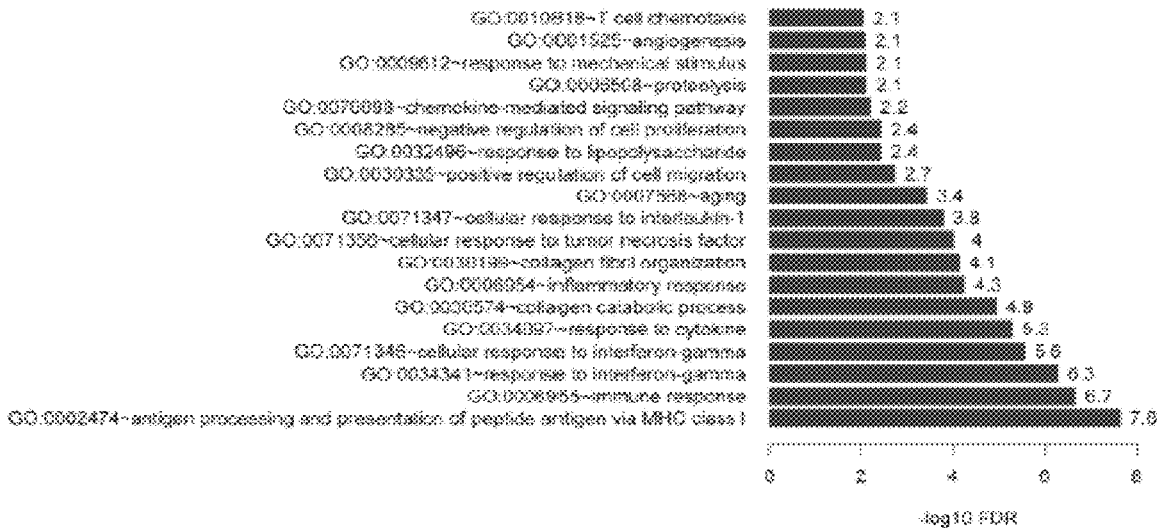

To investigate some of the mechanisms behind the effect of αKlotho and sTGFβR2 on osteoarthritis, the cartilage tissues were isolated from all the groups for RNA-seq analysis. The RNA-seq analysis revealed differentially expressed (DE) genes in the KT group when compared to OAC and SHAM group. Specifically, 489 genes were differentially expressed in KT vs SHAM, and 156 of them show a similar expression pattern between KT and HC. Gene Ontology (GO) analysis indicated that among these differentially expressed genes, those involved in inflammatory response and immune response exhibited the most dramatic effect upon KT treatment (see FIGS. 5A and 5B).

Figure 5C:
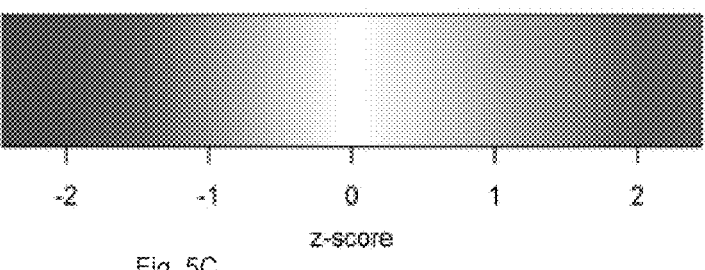
Figure 5D:
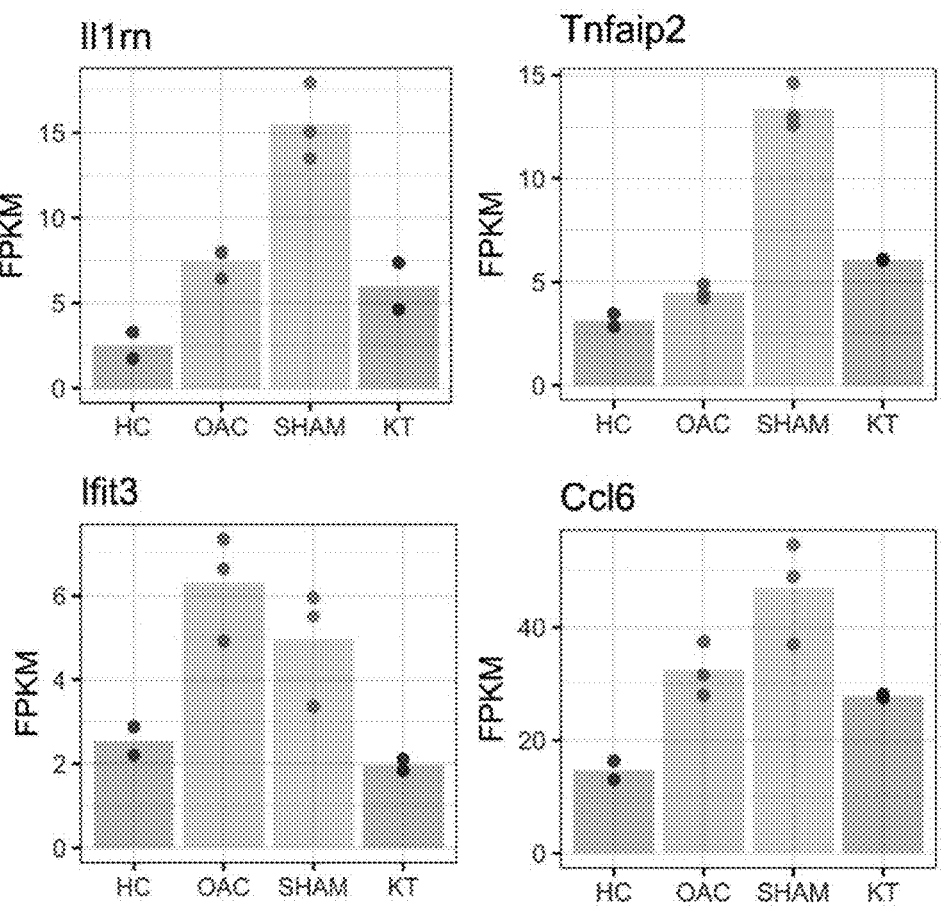
Figure 7:
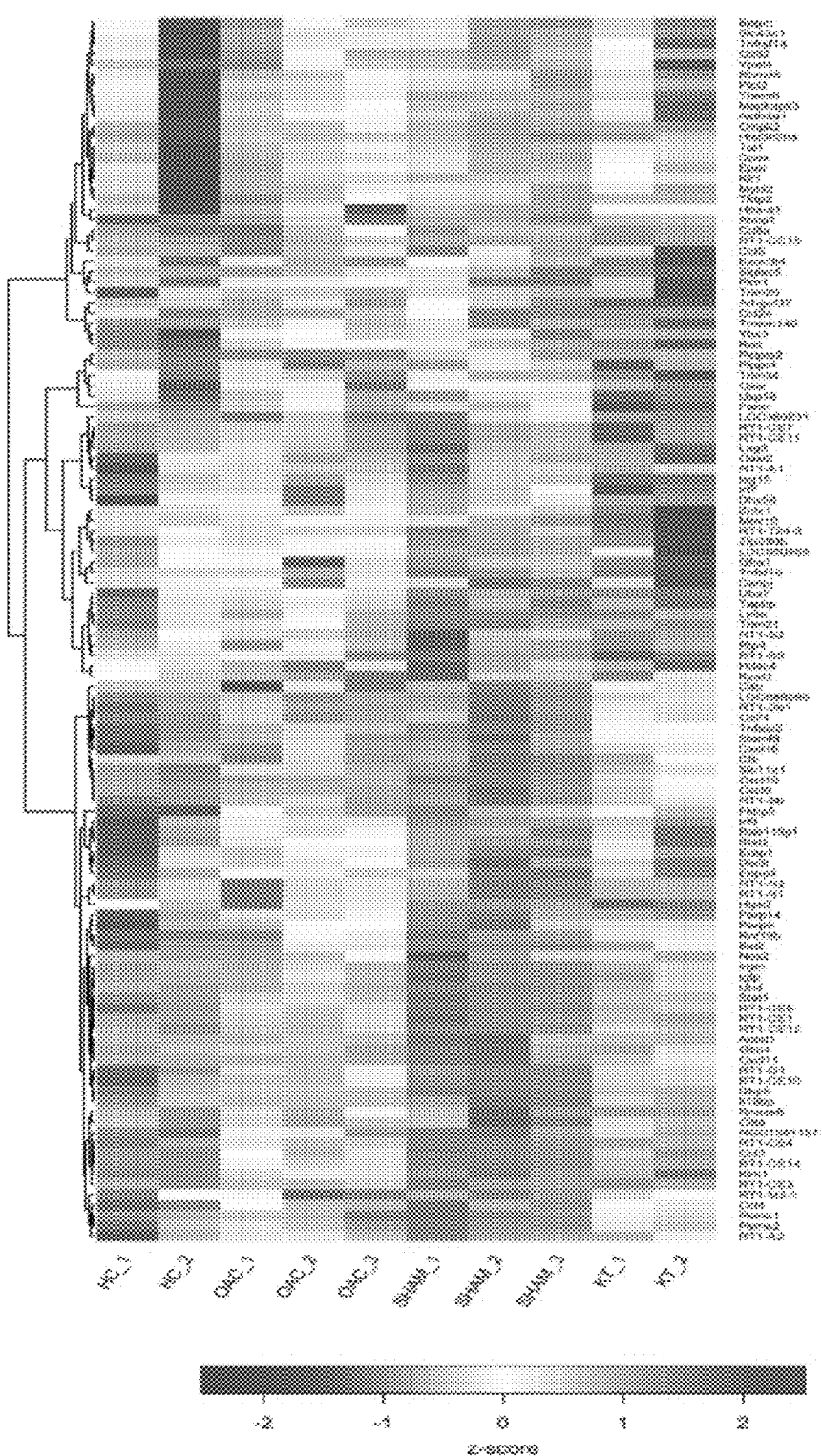
FIG. 7 depicts a heatmap that shows that sTGFβR2 and αKlotho prevent the activation of immune response mechanisms related to osteoarthritis. Heatmap of gene expression for DE genes differentially expressed between SHAM and KT (but were not differentially expressed between HC and OAC). Colors indicated the gene-wise relative expression values across conditions (low=blue, high=red). Row dendrogram showed the hierarchical clustering result based on the similarity of gene expression profile.

According to one aspect, it is known that chondrocytes secrete proinflammatory cytokines under pathological conditions such as osteoarthritis (see Akkiraju H, Nohe A. Role of Chondrocytes in Cartilage Formation, Progression of Osteoarthritis and Cartilage Regeneration. J Dev Biol. 2015 December; 3(4):177-92). Proinflammatory cytokines related to Nuclear factor (NF)-κB and Interleukin-1 (IL)-1β have been described to promote the action of MMPs contributing to the extracellular matrix degradation (see Raymond L, Eck S, Hays E, Tomek I, Kantor S, Vincenti. M. RelA is Required for IL-1β Stimulation of Matrix Metalloproteinase-1 Expression In Chondrocytes. Osteoarthritis Cartilage. 2007 April; 15(4):431-41; Liacini A, Sylvester J, Li W Q, Huang W, Dehnade F, Ahmad M, et al. Induction of matrix metalloproteinase-13 gene expression by TNF-alpha is mediated by MAP kinases, AP-1, and NF-kappaB transcription factors in articular chondrocytes. Exp Cell Res. 2003 Aug. 1; 288(1):208-17). Accordingly, when comparing OAC and SHAM groups to KT, the data showed downregulation of (1) Interleukin-related genes such as Il1rn (see FIG. 5D and FIG. 7); (2) Tnf-related/NF-κB-dependent genes such as Tnfaip2 (see FIG. 5D and FIG. 7); (3) interferon-related genes such as Ifit genes (see FIGS. 5C and 5D); and (4) cytokines or chemokines such as Cc16 (see FIGS. 5C and 5D) (see Appleton C T G, Pitelka V, Henry J, Beier F. Global analyses of gene expression in early experimental osteoarthritis. Arthritis Rheum. 2007 June; 56(6):1854-68; Jeyakumar V, Halbwirth F, Niculescu-Morzsa E, Bauer C, Zwickl H, Kern D, et al. Chondrogenic Gene Expression Differences between Chondrocytes from Osteoarthritic and Non-OA Trauma Joints in a 3D Collagen Type I Hydrogel. Cartilage. 2017 April; 8(2):191-8).

Accordingly, the data demonstrate that four weeks after the papain treatment the chondrocytes already show upregulation of pro-inflammatory cytokines and immune response related factors. αKlotho and sTGFβR2 treatment not only downregulated the expression of some of those already expressed genes, but also avoided the posterior upregulation of other immune response factors demonstrating the role of TGFβ in inflammation during osteoarthritis. TGFβ induces synovial lining cells to produce inflammatory factors which can further stimulate hyaline chondrocytes hypertrophy (see Scanzello C R, Goldring S R. The role of synovitis in osteoarthritis pathogenesis. Bone. 2012 August; 51(2):249-57). TGFβ signaling blockage significantly attenuated the synovial thickening implicated in the pathogenesis of osteoarthritis (see Scharstuhl A, Vitters E L, Kraan P M van der, Berg W B van den. Reduction of osteophyte formation and synovial thickening by adenoviral overexpression of transforming growth factor β/bone morphogenetic protein inhibitors during experimental osteoarthritis. Arthritis & Rheumatism. 2003 Dec. 1; 48(12):3442-51). Additionally, soluble Klotho modulates the PI3K/Akt and Wnt/β-catenin pathways, which are involved in cellular inflammatory responses. Different studies demonstrated how recombinant Klotho treatment was able to reduce cytokine levels implicated in kidney and cardiac disease (see Zhao Y, Banerjee S, Dey N, LeJeune W S, Sarkar P S, Brobey R, et al. Klotho Depletion Contributes to Increased Inflammation in Kidney of the db/db Mouse Model of Diabetes via RelA (Serine)536 Phosphorylation. Diabetes. 2011 July; 60(7):1907-16; Hui H, Zhai Y, Ao L, Cleveland J C, Liu H, Fullerton D A, et al. Klotho suppresses the inflammatory responses and ameliorates cardiac dysfunction in aging endotoxemic mice. Oncotarget. 2017 February 1; 8(9):15663-76). According to one aspect, the cooperative activity of both αKlotho and sTGFβR2 reduced the osteoarthritis-related inflammatory response.

During the inflammatory reaction that happens during osteoarthritis, the nitric oxide (NO) generated by Nos2 has destructive effects leading to chondrocyte death (see Vuolteenaho K, Moilanen T, Knowles R, Moilanen E. The role of nitric oxide in osteoarthritis. Scandinavian Journal of Rheumatology. 2009 Jul. 12; Vol 36(4):247-58). NO together with the reactive oxygen species (ROS) seem to be the primary inducers of chondrocyte death during osteoarthritis (see Del Carlo M, Loeser R F. Nitric oxide-mediated chondrocyte cell death requires the generation of additional reactive oxygen species. Arthritis Rheum. 2002 February; 46(2):394-403).

Figure 5E:
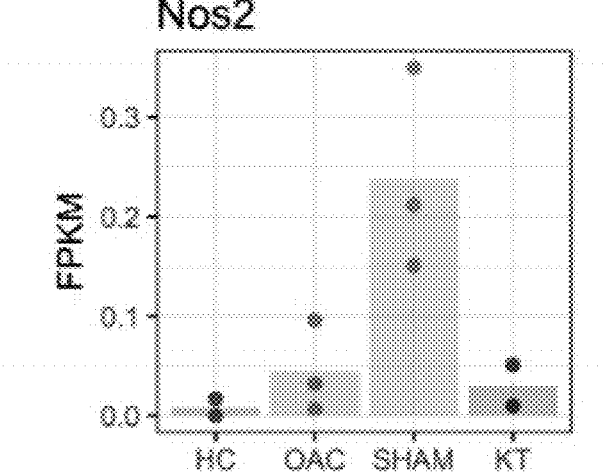

As a result, aspects of the present disclosure are directed to the use of αKlotho (or an active fragment thereof) and sTGFβR2 (or an active fragment thereof) as soluble factors directly or via gene therapy to avoid or lower the subsequent destructive processes induced by the proinflammatory response. According to one aspect, (see FIG. 5E and FIG. 7), the KT treatment prevented the upregulation of this enzyme which drastically increased in the SHAM animals any time after the AAV injection. AAV-mediated αKlotho and sTGFβR2 expression avoided cartilage degradation by diminishing IL-1β-induced NO production throughout the reduction of Il1rn and Nos2 mRNA levels in the chondrocytes. According to one aspect, αKlotho reduces oxidative stress and downregulates apoptosis upon KT treatment. (See Song S, Gao P, Xiao H, Xu Y, Si L Y. Klotho Suppresses Cardiomyocyte Apoptosis in Mice with Stress-Induced Cardiac Injury via Downregulation of Endoplasmic Reticulum Stress. PLOS ONE. 2013 dic; 8(12):e82968; Lin Y, Sun Z. Antiaging Gene Klotho Attenuates Pancreatic β-Cell Apoptosis in Type 1 Diabetes. Diabetes. 2015 Dec. 1; 64(12): 4298-311; Maekawa Y, Ohishi M, Ikushima M, Yamamoto K, Yasuda O, Oguro R, et al. Klotho protein diminishes endothelial apoptosis and senescence via a mitogen-activated kinase pathway. Geriatr Gerontol Int. 2011 October; 11(4):510-6).

Example V

αKlotho and sTGFβR2 Promote the Expression of Human Chondrocytes Markers In Vitro In order to assess the possible effectiveness of KT treatment on human cartilage, the effect of αKlotho and sTGFβR2 in vitro was tested using human primary articular chondrocytes. The articular chondrocytic phenotype is characterized by the expression of cartilage-specific extracellular matrix components, predominantly Col2a, and the cartilage-specific transcription factor Sox9. The expression of Sox9 is required for the commitment of mesenchymal cells toward the chondrogenic lineage (see Lefebvre V, Dvir-Ginzberg M. SOX9 and the many facets of its regulation in the chondrocyte lineage. Connect Tissue Res. 2016 Apr. 29; 58(1):2-14). The maintenance of this differentiated phenotype in vitro is highly dependent on the culture conditions. One of the major obstacles accompanying the monolayer culture of these cells is the loss of hyaline chondrocyte phenotype, leading to chondrocyte dedifferentiation or hypertrophy (see Ma B, Leijten J C H, Wu L, Kip M, van Blitterswijk C A, Post J N, et al. Gene expression profiling of dedifferentiated human articular chondrocytes in monolayer culture. Osteoarthr Cartil. 2013 April; 21(4):599-603).

Figure 6A:
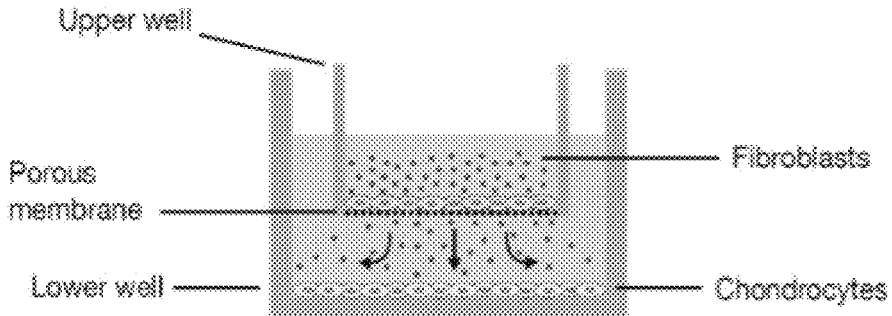
FIGS. 6A-6D depict results of in vitro recovery of chondrocyte markers by sTGFβR2 and αKlotho.
Figure 6B:
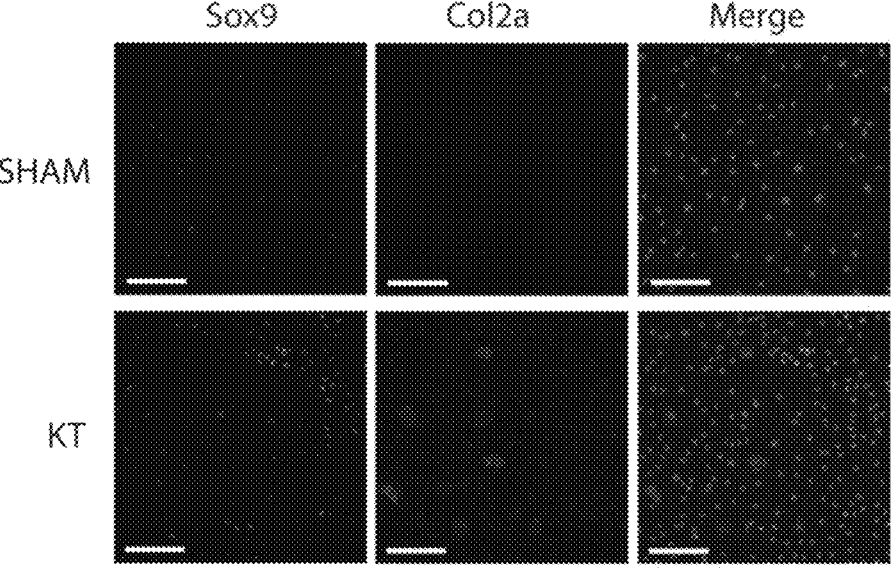
Figure 6C:
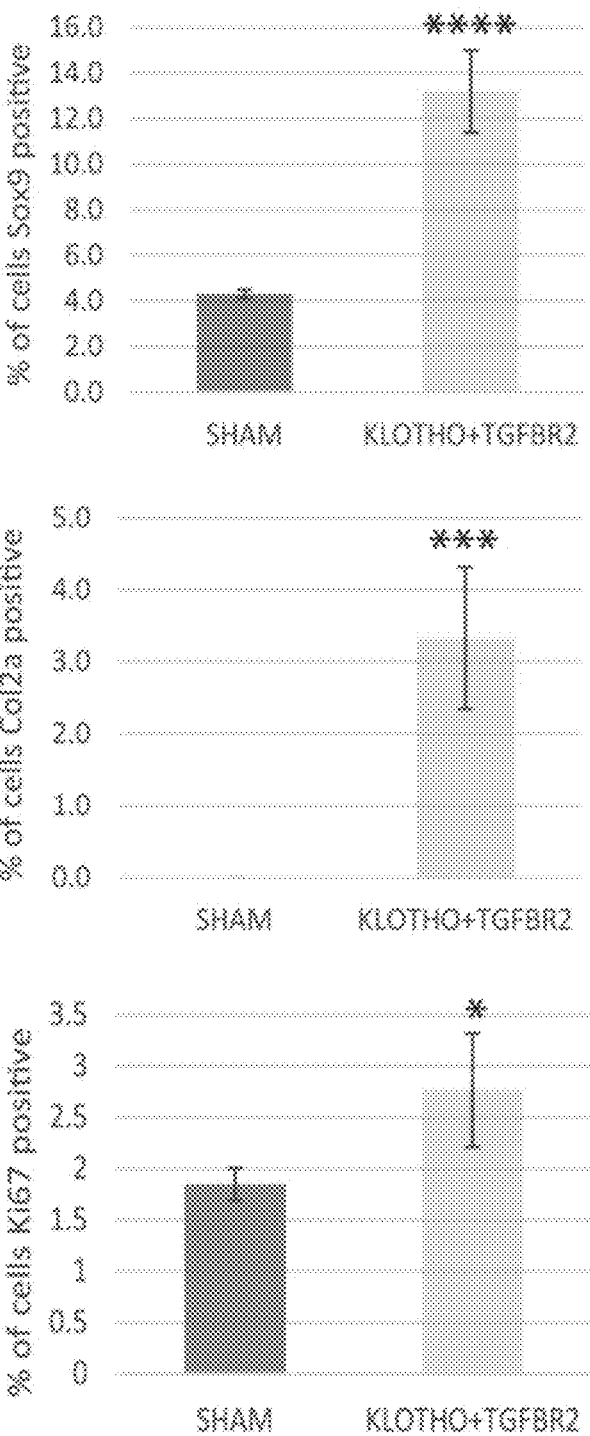

Therefore, the effect of both factors αKlotho and sTGFβR2 were tested on the phenotypic characteristics of the human hyaline chondrocytes in a monolayer culture condition using two separate vectors as described herein. First, to mimic the in vivo model, mesenchymal cells were infected by the virus and near the chondrocytes. For this purpose, a co-culture experiment was designed as described herein where human fibroblast were efficiently infected with AAV-DJ-αKlotho and AAV-DJ-sTGFβR2 (KT), or AAV-DJ-GFP as a control (see FIG. 6A). The results showed that mesenchymal cells transduced with KT displayed a higher percentage of chondrocytes expressing the chondrocyte-specific markers Sox9 and Col2a, essential in the cellular identity and ECM formation respectively (see FIG. 6B). An increase was also observed in the number of cycling cells within the culture (see FIGS. 6B and 6C), which supports the effect of αKlotho on cell proliferation. Accordingly a method is provided for the regrowth of cartilage by administering αKlotho or an active fragment thereof and sTGFβR2 or an active fragment thereof or administration of the genes in a vector for expression, such as AAV-DJ-αKlotho and AAV-DJ-sTGFβR2 treatment.

Figure 6D:
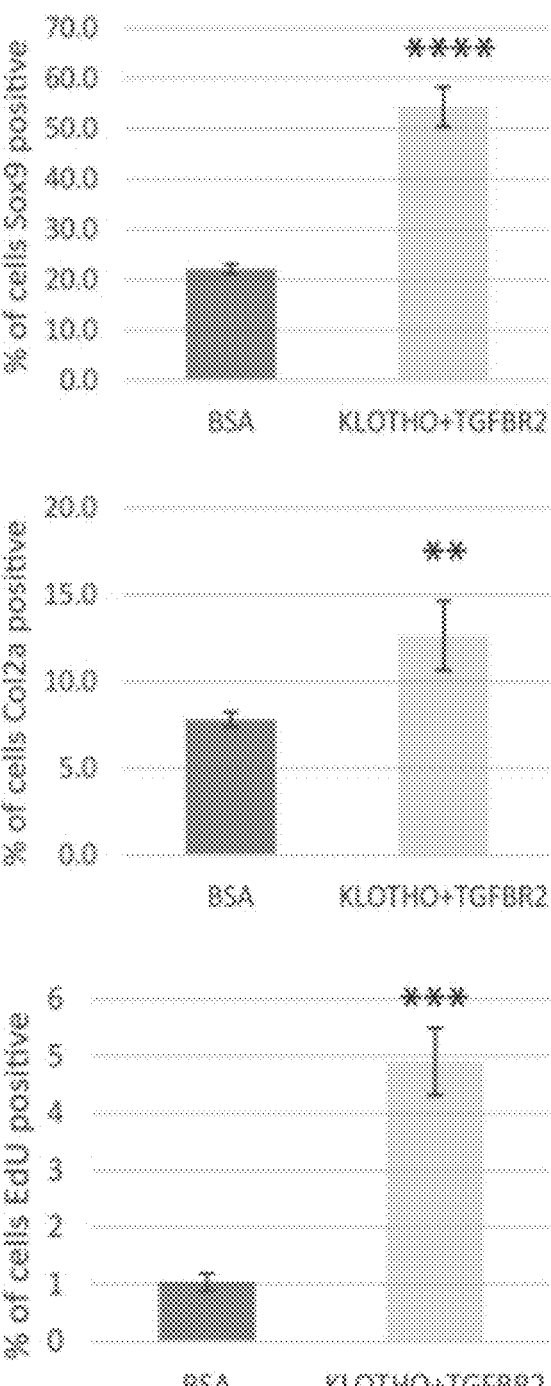

Additionally, the human articular chondrocytes were also treated in vitro using αKlotho and sTGFβR2 during 10 days. The results showed the same clear improvement demonstrated by the induction of Sox9 and Col2a protein expression, and the enhancement of cell proliferation (see FIG. 6D). Accordingly, a method is provided for treating human hyaline cartilage by administering αKlotho or an active fragment thereof and sTGFβR2 or an active fragment thereof or administration of the genes in a vector for expression, such as AAV-DJ-αKlotho and AAV-DJ-sTGFβR2 treatment. Accordingly, αKlotho and sTGFβR2 are administered to maintain chondrocytic phenotype in humans.

Example VI

Methods and Reagents

Cells Isolation and Culture

Human articular cartilage was obtained from healthy donors following informed consent for use in medical research, and rat articular cartilage was removed from the femoral and tibial condyles from a healthy rat under sterile conditions. Chondrocytes isolation and cultured was performed as described previously (see Gosset M, Berenbaum F, Thirion S, Jacques C. Primary culture and phenotyping of murine chondrocytes. Nat Protoc. 2008; 3(8):1253-60).

Human fibroblast (IMR90) were grown in basic culture medium at 37° C. and 5% CO2 conditions. Rat mesenchymal cells were isolated from joint capsule connective tissues. Briefly, connective tissues were enzymatically digested (as described (Yu G, Wu X, Kilroy G, Halvorsen Y-DC, Gimble J M, Floyd Z E. Isolation of murine adipose-derived stem cells. Methods Mol Biol. 2011; 702:29-36)) and subsequently the stromal vascular fraction was isolated by centrifugation and maintained in basic culture medium.

AAV Cloning and Production

The AAV plasmids were constructed following standard cloning techniques. (α-Klotho and sTGFβR2 were PCR amplified using primers as follows. α-Klotho-fwd-5'-cct-gaacacctgcaacgggcctgccaccATGCTAGCCCGCGCCC-CTCC (SEQ ID NO: 9) α-Klotho-rev-cctgaacgtctcct agctt-aTTACTTATAACTTCTCTGGCC (SEQ ID NO: 10) sTGFβR2-fwd-5'-cctgaacacctgcaacgggcctgccaccAT GGGT-CGGGGGTGCTCCGG-3' (SEQ ID NO: 11) the uppercase is the overlap to the secretion signal of TGFβR2 receptor, the bold is the AarI recognition site that creates a NotI overhang. sTGFβR2-Rev-5'-ggcttgattgtgggccctctggg-GTCGGGACTGCTGGTGGTGTATTC-3' (SEQ ID NO: 12) the bold is the overlap to the extracellular domain of TGFβR2 receptor and the lower case matches the igg2a, sequence used for overlap PCR. Igg2a-Fwd-5'-gaatacac-caccagcagtcccgacCCCAGAGGGCCCACAATCAAGCC-3' (SEQ ID NO: 13) the bold is the overlap to the mouse Igg2a FC region and the lower case matches the extracellular domain of TGFβR2 sequence used for overlap PCR. Igg2a-Rev 5'-cctgaacacctgccttactagcTCATTTACCCG-GAGTCCGGGAGAAG-3' (SEQ ID NO: 14) the bold is the AarI recognition site that creates a NheI overhang.

AAVs were prepared using 293AAV cells (Cell Biolabs, Inc.) as described with minor modifications (see Grieger J C, Choi V W, Samulski R J. Production and characterization of adeno-associated viral vectors. Nat Protoc. 2006; 1(3):1412-28). Briefly, cells were transfected using calcium phosphate and the virus purified by CsCl gradient. Virus titer was determined via qPCR using primers; ITR-F:5' GGAACCCCTAGTGATGGAGTT 3' (SEQ ID NO: 15) and ITR-R: 5' CGGCCTCAGTGAGCGA 3' (SEQ ID NO: 16).

Osteoarthritis Injury Model

Induction of experimental osteoarthritis was performed by intra-articular injection of 1001 of 4% Papain (Sigma-Aldrich, P4762) prepared in PBS followed by 501 of 0.03M L-Cysteine (Sigma) also in PBS. Both solutions were filtered before injection through a 0.22 μm filter. The injections were performed three times (day 1, 4 and 7). All animal procedures were performed according with protocols approved by the IACUC and Animal Resources Department of the Salk Institute for Biological Studies.

Animal Experimental Design

Twenty 250 g Sprague Dawley (SD) female rats were divided into 4 groups of 8 animals per group: healthy control group (HS), osteoarthritis group control (OAC), 4 weeks osteoarthritis treated with αKlotho and sTGFβR2 group (KT) and a 4 week osteoarthritis SHAM group (SHAM). OAC, KT and SHAM rats were treated with papain/cysteine.

OAC rats were sacrificed 4 weeks after the last papain/cysteine injection to determine the grade of osteoarthritis reached at that point. The other 2 groups were subjected to intra-articular AAV treatment: AAV-DJ-GFP was injected to the SHAM group, and AAV-DJ-αKlotho+AAV-DJ-sTGFβR2 to the KT group. A total number of $2.5 \times 10^{12}$ GC was injected per knee in 50 μl of PBS. These two last groups were sacrificed six weeks after the virus injection. Both knee joints were harvested from each rat: one knee for histological analysis and the other for RNA isolation. All animal procedures were performed according with protocols approved by the IACUC and Animal Resources Department of the Salk Institute for Biological Studies.

RNA Extraction

The cartilage surface was rinsed with saline and then dissected from the joint surfaces with a blade. Care was taken to avoid contamination by blood, bone or synovium. The tissue was cut into small pieces, immersed in TRIzol (Ambion) and immediately snap frozen and stored at −80° C. until further use. Total RNA was isolated from cartilage tissue by using TRIzol method. To determine the quality and integrity of total RNA samples (RIN), each RNA sample was run on a TapeStation automated electrophoresis analysis system (2200 TapeStation) according to the manufacturer's instructions. RNA concentrations were determined using Qubit Fluorometer 2.0.

Histology and Immunofluorescence

The whole knee joint was prepared for histology as described in Kawamoto and Shimizu, 2000 (see Kawamoto T, Shimizu M. A method for preparing 2- to 50-μm-thick fresh-frozen sections of large samples and undecalcified hard tissues. Histochem Cell Biol. 2000 May 1; 113(5):331-9).

Samples were sectioned at a thickness of 7 μm using the method described by Kawamoto and Kawamoto, 2014 (see Kawamoto T, Kawamoto K. Preparation of thin frozen sections from nonfixed and undecalcified hard tissues using Kawamot's film method (2012). Methods Mol Biol. 2014; 1130:149-64). Sections were then stained using different methods. Safranin-O/Fast Green staining was performed according to standard procedures. The pathological changes of articular cartilage were graded using the Osteoarthritis Research Society International (OARSI) scoring System following the advanced methodology (23): A grade of 0 was received for normal and healthy cartilage; grade 1 was applied when the cartilage surface was intact but contained abrasion areas, hypertrophy and cellular clusters; grade 1.5 refers to a grade 1 that includes cell death; grade 2 cartilage presented discontinued fibrillar surface; grade 2.5 consist on a grade 2 that include the loss of matrix shown by less than ⅓ of Safranin-O staining; grade 3 was considered when fissures appeared up to the mid zone and Safranin-O stained less than ⅔ of the cartilage; grade 3.5 presented deeper fissures into the mid zone; grade 4 refers to matrix loss by delamination of the superficial zone; grade 4.5 showed excavation into the mid zone; grade 5 cartilage showed completely eroded unmineralized cartilage; grade 5.5 showed growth of hypertrophy cartilage after the erosion; and 6, the higher grade, indicates the more severe cartilage damage when deformation of the condyle appears.

The thicknesses of the whole condylar cartilage were measured using the image analysis software Image J. The samples were evaluated by 2 blinded investigators and considering three different areas along the cartilage length.

For immunofluorescence analyses, sections were immunostained with antibodies and counterstained with 4,6-diamidino-2-phenylindole (DAPI). Imaging was performed using Slide Scanning Microscopy (Olympus VS-120 Virtual Slide Scanning Microscope).

The apoptosis detection was carried out on rat knee sections using In situ cell death detection AP kit (Roche) according to the manufacturer's protocol.

Antibodies

Collagen II (NeoMarkers) at a 1:100 (v/v) dilution, Runx2 (Santa Cruz Biotechnology) at a 1:100 (v/v) dilution, MMP13 (Abcam) at a 1:100 (v/v) dilution, MMP3 (Abcam) at a 1:100 (v/v) dilution, Sox9 (Abcam) at a 1:100 (v/v) dilution, Collagen X (Abcam) at a 1:50 (v/v), Ki67 (BioLegend) at a 1:100 (v/v) dilution. Antigen retrieval was performed by heat mediation 5% hyaluronidase in an acetate buffer for 1 hour at 37° C. Immunoreactivity was visualized with a biotinylated anti-mouse IgG secondary antibody using the Avidin/Biotin Blocking Kit (Vector Laboratories, Inc) according to the manufacturer's protocols.

In Vivo Luciferase Detection

Six 300 g Long Evans rats were used to test AAV-DJ intra-articular injection: AAV-DJ-Luc or AAV-DJ (empty vector, negative control). The luciferase was detected 2 weeks after injection using an IVIS Kinetic 2200 (Caliper Life Sciences). 50 mg/kg D-Luciferin (Biosynth) was injected intra-articular and intraperitoneal. Imaging was captured 10 min after the D-luciferin injection.

RNA Sequencing and Data Analysis

Reads were mapped to the rn6 reference (Illumina iGenomes) by STAR [v2.5.lb (Dobin A, Davis C A, Schlesinger F, Drenkow J, Zaleski C, Jha S, et al. STAR: ultrafast universal RNA-seq aligner. Bioinformatics. 2013 Jan. 1; 29(1):15-21)] with default parameters. Only the uniquely mapped reads were used in the downstream analysis. Gene expression levels were calculated by summing reads that were mapped across all exons of RefSeq genes by HOMER [v4.8 (Homer Software and Data Download [Internet]. Available from world wide website homer.ucsd.edu/ homer)]. The differentially expressed (DE) genes were identified using DESeq2 [v1.18.1 (Moderated estimation of fold change and dispersion for RNA-seq data with DESeq2 [Internet]. Available from world wide website ncbi.nlm.nih-.gov/pmc/articles/PMC4302049/) with the cutoff of log FC (log fold-change)>0.5 and FDR (false discovery rate)<0.05.

Enrichment test was carried out by DAVID (v6.8) (see Huang D W, Sherman B T, Lempicki R A. Bioinformatics enrichment tools: paths toward the comprehensive functional analysis of large gene lists. Nucleic Acids Res. 2009 January; 37(1):1-13), in which case the genes of interest were used as input signals and the whole genome of rn6 was used as background. Only Biological Process terms with Benjamini-Hochberg FDR<0.01 were used. Data can be accessed through the GEO accession number GSE118559.

All the statistical analyses of RNA-Seq were performed in the R environment unless specifically mentioned [v3.4.3, (R: a language and environment for statistical computing [Internet]. Available from world wide website gbif.org/tool/ 81287/r-a-language-and-environment-for-statistical-computing)]. R packages ggplot2 (ggplot2—Elegant Graphics for Data Analysis I Hadley Wickham I Springer [Internet]. Available from world wide website springer.com/us/book/ 9780387981413) and gplots (see Wickham H, Chang W, Henry L, Pedersen T L, Takahashi K, Wilke C, et al. ggplot2: Create Elegant Data Visualisations Using the Grammar of Graphics [Internet]. Available from world wide website CRAN.R-project.org/package=ggplot2) were used to plot the figures.

In Vitro Experiments

Co-culture experiments: Corning® Transwell® polyester membrane cell culture inserts (Sigma) of 4 μm pore size were used to evaluate the trans-in vitro effect of sTGFβR2 and αKlotho on human chondrocytes. Briefly, a p100 plate of human fibroblasts were transduced with $3 \times 10^{12}$ of AAV-DJ-αKlotho and AAV-DJ-TGFβR2. Two days after transduction, cells were reseeded in the upper well of the co-culture chamber, and the same day, chondrocytes were seeded in the lower well of the chamber. Chambers of cells were incubated in 37° C. and 5% CO2 conditions for 10 days.

Soluble factors experiments: Chondrocytes were plated at 60% confluence and treated with either BSA or 5 ng/ml and 10 ng/ml of αKlotho (Abcam ab84072) and sTGFβR2 (R&D Systems 241R2025) for 10 days. Cells were incubated in 37° C. and 5% CO2 conditions and media with the factors or BSA were changed every 3 days.

Immunofluorescence of Cell Cultures.

Previous to fixation, cells were incubated with EdU for 2 hours, according to standard protocols. Cells were then fixed using 4% PFA. Cells were permeabilized with 0.1% Triton X-100 in PBS for 20 min at room temperature (RT). After washing with PBS, cells were blocked using 1% BSA in PBS for 1 h and incubated with primary antibody at 4° C. overnight (Collagen II diluted 1:150 and Sox9 1:300). The secondary antibody was incubated 1 hour at room temperature. EdU staining was performed using Click-iT™ EdU Alexa Fluor™ 488 Imaging Kit (Invitrogen). Counterstaining was performed using DAPI. Images were obtained using a Zeiss LSM 880 Rear Port Laser Scanning Confocal.

Flow Cytometry Analysis

GFP positive cells were detected using a FACS Canto II (BD Biosciences) after filtering (70 μm) and washing with 2% FBS/PBS.

Statistics

Quantification data is expressed as averages±s.e. Statistical significance (*P values) was determined by an unpaired, two-tailed Student's t-test with Welch's correction (there is no assumption of an equal s.d. in each group). All analyses were performed with Prism 7 software from Graph-Pad (San Diego, CA, USA). Statistical significance was determined to be P<0.05, P<0.01, *P<0.001, ****P<0.0001.

Example VII

Gene Therapy Treatment of Osteoarthritis Using Systemic Injection of sTGFbR2+αKlotho Osteoarthritic (OA) lesions were created by intra-articular injection of papain as described herein and primarily consisted of an intact cartilage surface with superficial fibrillation, chondrocyte death/loss and proliferation, edema, and/ or loss of proteoglycan matrix in the superficial zone. Occasionally, deeper fibrillations, abrasions, and fissures were observed extending into the mid zone. Additionally, superficial fibrillations were observed along the surface of the menisci. Fibrillations were characterized by small cracks and discontinuities of the cartilage matrix in the superficial zone or the meniscal surface. Chondrocyte death/loss was characterized by the absence of chondrocytes or "ghost" chondrocytes present in the superficial and mid zones of cartilage. Chondrocyte proliferation was characterized by increased numbers of chondrocytes, often disorganized, within the superficial and mid zones of cartilage. Edema was characterized by increased clear fluid surrounding chondrocytes of the superficial and mid zones of the cartilage.

Loss of proteoglycan matrix was characterized by decreased or absent cationic staining (red; Safranin O); loss of matrix could be present directly adjacent to viable chondrocytes or in areas of chondrocyte loss and was typically accompanied by other lesions as described above. Abrasions were characterized by focal loss of the superficial zone leaving a roughened surface. Fissures were characterized by vertical matrix separation extending into the mid zone cartilage. Viral vectors comprising nucleic acids encoding sTGFbR2 and FGF21 were systemically injected into rats to determine gene therapy treatment of osteoarthritis in rat knees.

Figure 8:
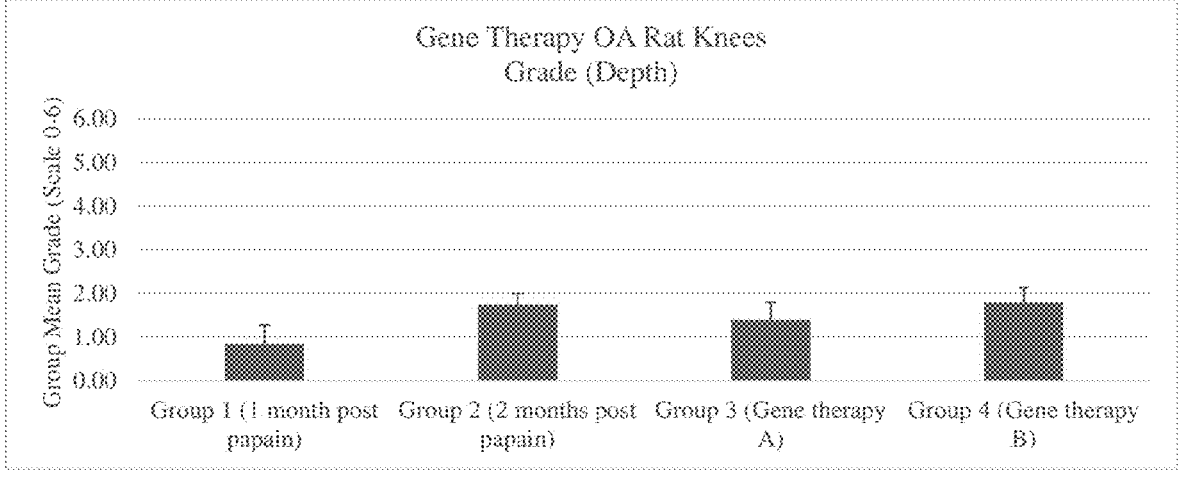
FIG. 8 depicts data related to Grade (depth) of osteoarthritis in a mouse knee treated with the gene therapy by systemic injection as described herein. Group mean+/− standard error of the mean (SEM). The 2-month post papain control (Group 2) and STGFbR2+FGF21 (Group 4) exhibited the highest grades and the 1-month post papain control (Group 1) exhibited the lowest grade. A slight reduction in grade was observed in the STGFbR2+αKlotho (Group 3) when compared to the 2-month post papain control (Group 2).

As shown in FIG. 8, OA grade was determined based on the depth (superficial, mid, deep, or with bone involvement) of the most severe lesions observed in the sample. The 2-month post papain control group (Group 2) and the sTGFbR2+FGF21 treated group (Group 4) exhibited the highest grade and the 1-month post papain control group (Group 1) exhibited the lowest grade. A slight reduction in grade was observed in the sTGFbR2+αKlotho treated group (Group 3) when compared to the 2-month post papain control group (Group 2).

Figure 9:
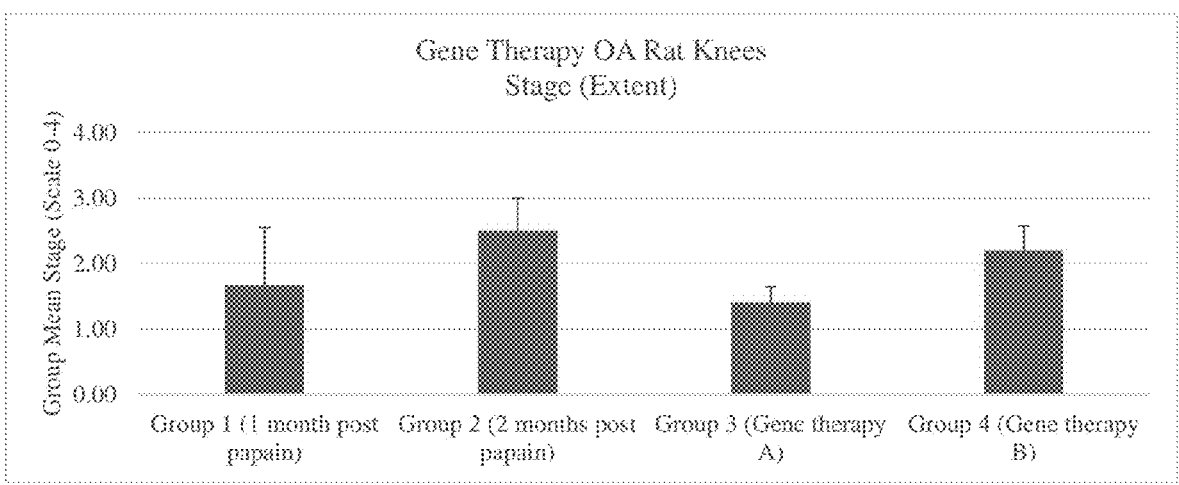
FIG. 9 depicts data related to Stage (extent) of osteoarthritis in a mouse knee treated with the gene therapy by systemic injection as described herein. Group mean+/− SEM. The 2-month post papain control (Group 2) exhibited the highest mean OA stage; a similar mean stage was observed in the STGFbR2+FGF21 (Group 4). A lower mean OA stage was observed in the 1-month post papain control (Group 1) compared to the 2 month control (Group 2). The lowest mean OA stage was observed in the STGFbR2+ αKlotho (Group 3), exhibiting a reduction in lesion severity when compared to the two control groups (Groups 1 and 2).

As shown in FIG. 9, OA stage was determined based on the total extent of the cartilage affected by the OA lesions. Amongst group trends were similar to those observed for OA grade, however the lowest mean score for OA stage was observed in the sTGFbR2+αKlotho treated (Group 3).

Figure 10:
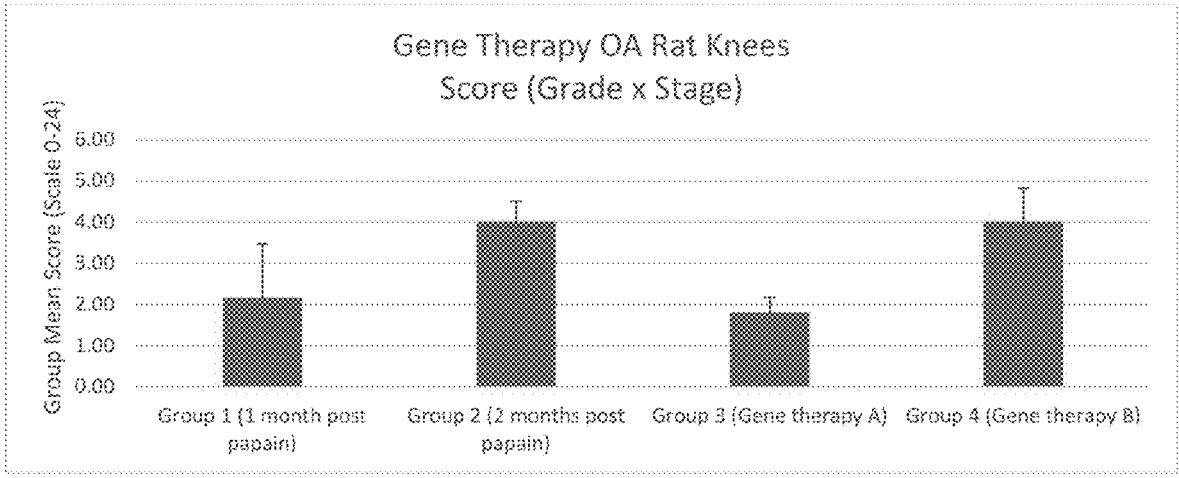
FIG. 10 depicts data related to Score (grade×stage) of osteoarthritis in a mouse knee treated with the gene therapy by systemic injection as described herein. Group mean+/− SEM. The 2-month post papain group (Group 2) and the STGFbR2+FGF21 (Group 4) exhibited the highest scores; no difference was observed between these groups. The 1-month post papain group (Group 1) had lower scores compared to the 2-month post papain group (Group 2). The STGFbR2+αKlotho (Group 3) exhibited the lowest scores, indicating a reduction in lesion severity compared to the two control groups (Groups 1 and 2).

As shown in FIG. 10, OA score was determined by multiplying the grade and stage for a total OA value. Amongst group trends were similar to those observed for OA stage. The 2-month post papain group (Group 2) and the sTGFbR2+FGF21 treated group (Group 4) exhibited identical as well as the highest scores. The 1-month post papain group (Group 1) had lower scores compared to the 2-month post papain group (Group 2). The sTGFbR2+αKlotho treated group (Group 3) exhibited the lowest scores, indicating a reduction in lesion severity compared to the two control groups (Groups 1 and 2).

Figure 11:
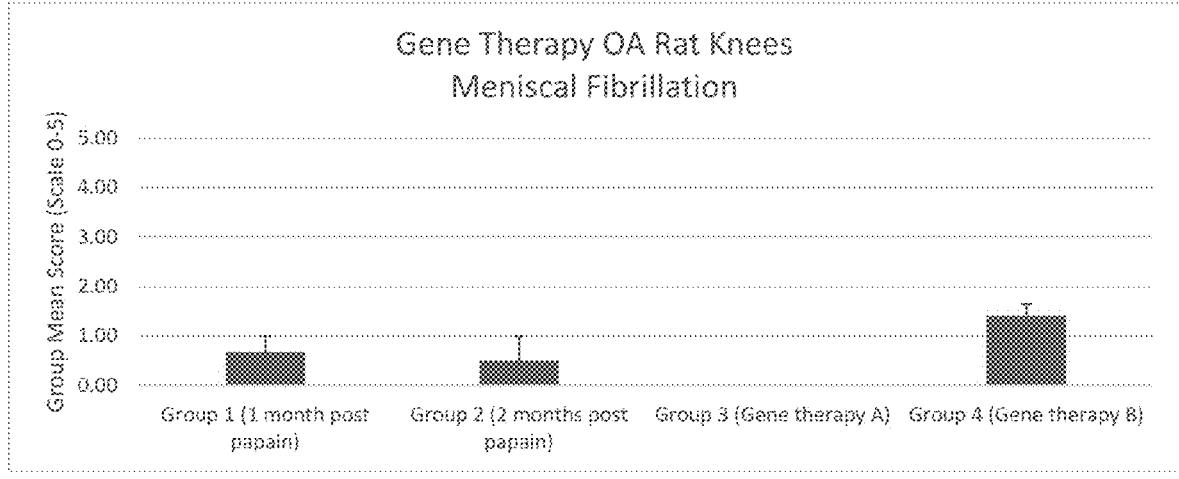
FIG. 11 depicts data related to meniscal fibrillation of osteoarthritis in a mouse knee treated with the gene therapy by systemic injection as described herein. Group mean+/− SEM. Meniscal fibrillation was observed in the two control groups (Groups 1 and 2) and the STGFbR2+FGF21 (Group 4); Group 4 exhibited the highest severity of meniscal fibrillation scores. Meniscal fibrillation was absent in the STGFbR2+αKlotho(Group 3).

As shown in FIG. 11, minimal to mild meniscal fibrillation was observed in the two control groups (Groups 1 and 2) and the sTGFbR2+FGF21 treated group (Group 4); Group 4 exhibited the highest meniscal fibrillation scores. Meniscal fibrillation was absent in the sTGFbR2+αKlotho treated group (Group 3).

Example VIII

Comparison of Treatment Using a Combination of αKlotho and sTGFbR2 Versus Each Individually The analysis of the combined effect of αKlotho ("K") and sTGFbR2 ("T") identified as ("KT") was first analyzed by using an osteoarthritis in vitro model using high TGFb1 concentration. The results analyzed by qPCR showed how the combination of both soluble factors synergistically favors the inhibition of hypertrophic markers and ECM proteolytic enzymes when compared to the single factor treatments (FIG. 12A, KT versus K versus T). Accordingly, also the chondrocytes treated with both factors showed higher protein expression of ACAN than αKLOTHO or sTGFbR2 (FIG. 12B). FIG. 12C describes the time line of injection.

Example IX

Embodiments

Embodiments of the present disclosure are directed to a method of treating osteoarthritis in a subject in need thereof, the method including the step of administering to the subject a first viral vector including a first nucleic acid sequence encoding an sTGFβ-R2 protein or an active fragment thereof; and a second nucleic acid sequence encoding an αKlotho protein or an active fragment thereof, thereby treating osteoarthritis in the subject. According to one aspect, the first nucleic acid sequence and the second nucleic acid sequence are separated by a polycistronic element. According to one aspect, the polycistronic element is an IRES or 2A sequence.

Embodiments of the present disclosure are directed to a method of treating osteoarthritis in a subject in need thereof, the method including the step of administering to the subject a first viral vector including a first nucleic acid sequence encoding an sTGFβ-R2 protein or an active fragment thereof; and a second viral vector including a second nucleic acid sequence encoding an αKlotho protein or an active fragment thereof, thereby treating osteoarthritis in the subject. According to one aspect, the first nucleic acid sequence is operably linked to a first regulatory sequence and/or the second nucleic acid sequence is operably linked to a second regulatory sequence. According to one aspect, the first regulatory sequence drives expression of the sTGFβ-R2 protein or active fragment thereof, and/or the second regulatory sequence drives expression of the αKlotho protein or active fragment thereof. According to one aspect, the first regulatory sequence and the second regulatory sequence each comprise a promoter. According to one aspect, the promoter is a constitutive promoter or an inducible promoter. According to one aspect, the first regulatory sequence and the second regulatory sequence each comprise a cell-specific promoter or a tissue-specific promoter. According to one aspect, the first regulatory sequence and the second regulatory sequence each comprise a liver-specific promoter. According to one aspect, the regulatory sequence comprises a promoter selected from the group consisting of an hEf1α promoter, an shEf1α promoter (or truncated hEf1α promoter), a CAG promoter (such as cytomegalovirus, chicken beta-actin intron, splice acceptor of the rabbit beta-globin gene), a CMV promoter, an hAAT promoter, a thyroid hormone-binding globulin promoter, an albumin promoter, a thyroxin-binding globulin (TBG) promoter, a hepatic control region (HCR)-ApoCII hybrid promoter, a CASI promoter, an HCR-hAAT hybrid promoter, an hAAT promoter combined with mouse albumin gene enhancer (Ealb) element, and an apolipoprotein E promoter. According to one aspect, the first nucleic acid sequence is operably linked to a 3' untranslated region for RNA stability and expression in mammalian cells. According to one aspect, the 3' untranslated region comprises a sequence selected from the group consisting of a WPRE sequence, a WPRE3 sequence, an SV40 late polyadenylation signal (e.g., truncated), an HBG polyadenylation signal, a rabbit beta-globin polyadenylation signal, a bovine bgpA, an ETC polyadenylation signal, and any combination thereof. According to one aspect, the first viral vector and/or the second viral vector is an adeno-associated virus (AAV) vector. According to one aspect, the AAV vector is AAV-DJ. According to one aspect, the AAV vector is derived from an AAV serotype selected from AAV1, AAV2, AAV3, AAV4, AAV5, AAV6, AAV7, AAV8, AAV9, AAV10, AAV, 11, AAV12, AAV2.5, and AAVrh10.XX viral vectors. According to one aspect, the sTGFβ-R2 protein is selected from the group consisting of a human, a canine, a feline, a bovine, an ovine, a caprine, an equine, a murine, and a porcine sTGFβ-R2 protein. According to one aspect, the sTGFβ-R2 protein is a human sTGFβ-R2 protein. According to one aspect, the sTGFβ-R2 protein is a canine sTGFβ-R2 protein. According to one aspect, the sTGFβ-R2 protein comprises an amino acid sequence having at least 90% sequence identity to the amino acid sequence set forth in SEQ ID NO:3. According to one aspect, the αKlotho protein is selected from the group consisting of a human, a canine, a feline, a bovine, an ovine, a caprine, an equine, a murine, and a porcine αKlotho protein. According to one aspect, the αKlotho protein is a human αKlotho protein. According to one aspect, the αKlotho protein is a canine αKlotho protein. According to one aspect, the αKlotho protein comprises an amino acid sequence having at least 90% sequence identity to the amino acid sequence set forth in SEQ ID NO:1. According to one aspect, the sTGFβ-R2 protein and/or the αKlotho protein is an Fc fusion protein comprising an Ig Fc domain. According to one aspect, the Ig Fc domain is selected from the group consisting of a human, a canine, a feline, a bovine, an ovine, a caprine, an equine, a murine, and a porcine Fc or a subtype thereof, including IgG1, IgG2a, IgG2b, IgG3, and IgG4. According to one aspect, the Ig Fc domain comprises an amino acid sequence having at least 90% sequence identity to the amino acid sequence set forth in SEQ ID NO:5, SEQ ID NO:6 or SEQ ID NO:7. According to one aspect, the sTGFβ-R2 protein and/or the αKlotho protein is expressed and distributed systemically. According to one aspect, the first viral vector and/or the second viral vector is administered by intravenous injection. According to one aspect, the first viral vector and/or the second viral vector is administered by intra-articular injection into cartilage at osteoarthritic site. According to one aspect, the first viral vector and/or the second viral vector infects mesenchymal cells at an osteoarthritic site. According to one aspect, treating osteoarthritis in the subject includes reducing the progression of osteoarthritis in the subject, compared to a control subject. According to one aspect, osteoarthritis in the subject includes increased, regenerated, or regrown cartilage at an osteoarthritic site in the subject, compared to a control subject. According to one aspect, treating osteoarthritis in the subject includes reducing inflammation at an osteoarthritic site in the subject, compared to a control subject. According to one aspect, the subject is a mammal. According to one aspect, the mammal is a human. According to one aspect, the mammal is a canine.

Embodiments of the present disclosure are directed to a method of treating osteoarthritis in a subject in need thereof, the method including the step of administering to the subject a therapeutically effective amount of a combination of an αKlotho protein or an active fragment thereof; and an sTGFβ-R2 protein or an active fragment thereof, thereby treating osteoarthritis in the subject. According to one aspect, the αKlotho protein or an active fragment thereof is administered as a soluble protein and the sTGFβ-R2 protein or an active fragment thereof is administered as a soluble protein. According to one aspect, the αKlotho protein and/or the sTGFβ-R2 protein is administered by intravenous injection. According to one aspect, the αKlotho protein and/or the sTGFβ-R2 protein is administered by intra-articular injection into cartilage at an osteoarthritic site. According to one aspect, treating osteoarthritis in the subject includes reducing the progression of osteoarthritis in the subject, compared to a control subject. According to one aspect, treating osteoarthritis in the subject includes increased, regenerated, or regrown cartilage at the osteoarthritic site in the subject, compared to a control subject. According to one aspect, treating osteoarthritis in the subject includes reducing inflammation at an osteoarthritic site in the subject, compared to a control subject.

Embodiments of the present disclosure are directed to a method of treating osteoarthritis in a subject in need thereof, the method including the step of administering to the subject a nucleic acid molecule including a first nucleic acid sequence encoding for an αKlotho protein or an active fragment thereof; and a second nucleic acid sequence encoding for an sTGFβ-R2 protein or an active fragment thereof, thereby treating osteoarthritis in the subject. According to one aspect, the first nucleic acid sequence and the second nucleic acid sequence are separated by a polycistronic element. According to one aspect, the polycistronic element is an IRES or 2A sequence. According to one aspect, the nucleic acid molecule is administered by intravenous injection. According to one aspect, the nucleic acid molecule is administered by intra-articular injection into cartilage at an osteoarthritic site. According to one aspect, treating osteoarthritis in the subject includes reducing the progression of osteoarthritis in the subject, compared to a control subject. According to one aspect, treating osteoarthritis in the subject includes increased, regenerated, or regrown cartilage at an osteoarthritic site in the subject, compared to a control subject. According to one aspect, treating osteoarthritis in the subject includes reducing inflammation at an osteoarthritic site in the subject, compared to a control subject. According to one aspect, the nucleic acid molecule includes DNA, RNA, or a combination thereof. According to one aspect, the subject is a mammal. According to one aspect, the mammal is a human. According to one aspect, the mammal is a canine.

Embodiments of the present disclosure are directed to a vector including a first nucleic acid sequence encoding an αKlotho protein or an active fragment thereof; and a second nucleic acid sequence encoding a soluble Transforming Growth Factor Beta Receptor II (sTGFβ-R2) protein or an active fragment thereof. According to one aspect, the first nucleic acid sequence and the second nucleic acid sequence are separated by a polycistronic element. According to one aspect, the polycistronic element is an IRES or 2A sequence. According to one aspect, a first promoter is operably linked to the first nucleic acid sequence for expression of the αKlotho protein or an active fragment thereof in a mammalian cell; and a second promoter is operably linked to the second nucleic acid sequence for expression of the sTGFβ-R2 protein or an active fragment thereof in a mammalian cell. According to one aspect, the first promoter and the second promoter are cell or tissue specific. According to one aspect, the first promoter and the second promoter are constitutive or inducible. According to one aspect, the αKlotho protein and the sTGFβ-R2 protein are selected from the group consisting of human, canine, feline, bovine, ovine, caprine, equine, murine and porcine proteins. According to one aspect, the αKlotho protein or active fragment thereof and the sTGFβ-R2 protein or active fragment thereof are canine proteins. According to one aspect, the αKlotho protein or active fragment thereof and the sTGFβ-R2 protein or active fragment thereof are human proteins. According to one aspect, the αKlotho protein comprises an amino acid sequence having at least 90% sequence identity to the amino acid sequence set forth in SEQ ID NO:1. According to one aspect, the sTGFβ-R2 protein comprises an amino acid sequence having at least 90% sequence identity to the amino acid sequence set forth in SEQ ID NO:3.

Embodiments of the present disclosure are directed to a pharmaceutical formulation comprising the vector as described above and a pharmaceutically acceptable excipient.

Embodiments of the present disclosure are directed to a method of treating osteoarthritis in a mammal in need thereof including the step of administering a therapeutically effective amount of a combination of αKlotho protein or an active fragment thereof and sTGFβ-R2 protein or an active fragment thereof to the mammal at a site within the mammal exhibiting osteoarthritis, wherein progression of the osteoarthritis is reduced compared to the untreated condition, or wherein cartilage at the site of the osteoarthritis is increased or regenerated or regrown compared to the untreated condition, or wherein inflammation is reduced compared to the untreated condition. According to one aspect, the mammal is a dog or a human. According to one aspect, the αKlotho protein or an active fragment thereof is administered as a soluble protein and the sTGFβ-R2 protein or an active fragment thereof is administered as a soluble protein. According to one aspect, the αKlotho protein or an active fragment thereof is administered as a soluble protein by intra-articular cartilage injection and the sTGFβ-R2 protein or an active fragment thereof is administered as a soluble protein by intra-articular cartilage injection. According to one aspect, a vector comprising a first nucleic acid sequence encoding the αKlotho protein or an active fragment thereof and a second nucleic acid sequence encoding the sTGFβ-R2 protein or an active fragment thereof is administered and the first nucleic acid sequence is expressed to produce the αKlotho protein or an active fragment thereof and the second nucleic acid sequence is expressed to produce the sTGFβ-R2 protein or an active fragment thereof. According to one aspect, a vector comprising a first nucleic acid sequence encoding the αKlotho protein or an active fragment thereof and a second nucleic acid sequence encoding the sTGFβ-R2 protein or an active fragment thereof is administered by intra-articular cartilage injection and the first nucleic acid sequence is expressed to produce the αKlotho protein or an active fragment thereof and the second nucleic acid sequence is expressed to produce the sTGFβ-R2 protein or an active fragment thereof. According to one aspect, a first vector comprising a first nucleic acid sequence encoding the αKlotho protein or an active fragment thereof and a second vector comprising a second nucleic acid sequence encoding the sTGFβ-R2 protein or an active fragment thereof is administered and the first nucleic acid sequence is expressed to produce the αKlotho protein or an active fragment thereof and the second nucleic acid sequence is expressed to produce the sTGFβ-R2 protein or an active fragment thereof. According to one aspect, a first vector comprising a first nucleic acid sequence encoding the αKlotho protein or an active fragment thereof and a second vector comprising a second nucleic acid sequence encoding the sTGFβ-R2 protein or an active fragment thereof is administered by intra-articular cartilage injection and the first nucleic acid sequence is expressed to produce the αKlotho protein or an active fragment thereof and the second nucleic acid sequence is expressed to produce the sTGFβ-R2 protein or an active fragment thereof. According to one aspect, the vector is a recombinant virus. According to one aspect, the vector is a parvovirus. According to one aspect, the vector is an AAV vector. According to one aspect, the AAV vector is AAV-DJ. According to one aspect, the vector is an AAV vector serotyped for AAV1, AAV2, AAV3, AAV4, AAV5, AAV6, AAV7, AAV8, AAV9, AAV10, AAV11, AAV12, AAV2.5, or AAVrh10.XX or combinations thereof. According to one aspect, the vector infects mesenchymal cells at the site of the osteoarthritis. According to one aspect, the first vector and the second vector are a recombinant virus. According to one aspect, the first vector and the second vector are a parvovirus. According to one aspect, the first vector and the second vector are an AAV vector. According to one aspect, the first vector and the second vector are an AAV-DJ vector. According to one aspect, the first vector and the second vector are an AAV vector serotyped for AAV1, AAV2, AAV3, AAV4, AAV5, AAV6, AAV7, AAV8, AAV9, AAV10, AAV11, AAV12, AAV2.5, or AAVrh10.XX or combinations thereof. According to one aspect, the first vector and the second vector infect mesenchymal cells at the site of the osteoarthritis. According to one aspect, the αKlotho protein or active fragment thereof and the sTGFβ-R2 protein or active fragment thereof are human proteins. According to one aspect, the αKlotho protein or active fragment thereof and the sTGFβ-R2 protein or active fragment thereof are canine proteins. According to one aspect, the αKlotho protein and the sTGFβ-R2 protein are selected from the group consisting of human, canine, feline, bovine, ovine, caprine, equine, murine and porcine proteins. According to one aspect, the αKlotho protein has at least 90% sequence identity to the amino acid sequence of an αKlotho protein corresponding to SEQ ID NO:1. According to one aspect, the sTGFβ-R2 protein has at least 90% sequence identity to the amino acid sequence of a sTGFβ-R2 protein corresponding to SEQ ID NO:3.

Embodiments of the present disclosure are directed to a vector including a first nucleic acid sequence encoding an αKlotho protein or an active fragment thereof and a second nucleic acid sequence encoding a soluble Transforming Growth Factor Beta Receptor II (sTGFβ-R2) protein or an active fragment thereof. According to one aspect, a first promoter is operably linked to the first nucleic acid sequence for expression of the αKlotho protein or an active fragment thereof in a mammalian cell, and a second promoter is operably linked to the second nucleic acid sequence for expression of the sTGFβ-R2 protein or an active fragment thereof in a mammalian cell. According to one aspect, the first promoter and the second promoter are cell or tissue specific. According to one aspect, the first promoter and the second promoter are constitutive or inducible. According to one aspect, the αKlotho protein or active fragment thereof and the sTGFβ-R2 protein or active fragment thereof are human proteins. According to one aspect, the αKlotho protein or active fragment thereof and the sTGFβ-R2 protein or active fragment thereof are canine proteins. According to one aspect, the αKlotho protein and the sTGFβ-R2 protein are selected from the group consisting of human, canine, feline, bovine, ovine, caprine, equine, murine and porcine proteins. According to one aspect, the αKlotho protein has at least 90% sequence identity to the amino acid sequence of an αKlotho protein corresponding to SEQ ID NO:1. According to one aspect, the sTGFβ-R2 protein has at least 90% sequence identity to the amino acid sequence of a sTGFβ-R2 protein corresponding to SEQ ID NO:3.

Embodiments of the present disclosure are directed to a pharmaceutical formulation comprising the vector described thereof in a pharmaceutically acceptable excipient.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating osteoarthritis in a subject in need thereof, the method comprising administering to the subject:

(i) a first viral vector comprising a first nucleic acid sequence encoding a soluble Transforming Growth Factor Beta Receptor II (sTGFβ-R2) protein and a second nucleic acid sequence encoding an αKlotho protein, optionally wherein the first nucleic acid sequence and second nucleic acid sequence are operably linked via a polycistronic element; or (ii) a first viral vector comprising a first nucleic acid sequence encoding a soluble Transforming Growth Factor Beta Receptor II (sTGFβ-R2) protein and a second viral vector comprising a second nucleic acid sequence encoding an αKlotho protein.

2. The method of claim 1, wherein the polycistronic element is an internal ribosome entry site (IRES) or 2A sequence.

3. The method of claim 1, wherein the first nucleic acid sequence is operably linked to a first regulatory sequence that drives expression of the sTGFβ-R2 protein, and/or the second nucleic acid sequence is operably linked to a second regulatory sequence that drives expression of the αKlotho protein.

4. The method of claim 3, wherein the first regulatory sequence and the second regulatory sequence each comprise a promoter.

5. The method of claim 1, wherein the first nucleic acid sequence is operably linked to a 3' untranslated region.

6. The method of claim 1, wherein the first viral vector and/or the second viral vector is:

(i) a recombinant viral vector;

(ii) a parvoviral vector; and/or (iii) an adeno-associated virus (AAV) vector.

7. The method of claim 1, wherein the sTGFβ-R2 protein comprises a human sTGFβ-R2 protein, a canine sTGFβ-R2 protein, a feline sTGFβ-R2 protein, a bovine sTGFβ-R2 protein, an ovine sTGFβ-R2 protein, a caprine sTGFβ-R2 protein, an equine STGFβ-R2 protein, a murine sTGFβ-R2 protein, or a porcine sTGFβ-R2 protein.

8. The method of claim 1, wherein the αKlotho protein comprises a human αKlotho protein, a canine αKlotho protein, a feline αKlotho protein, a bovine αKlotho protein, an ovine αKlotho protein, a caprine αKlotho protein, an equine αKlotho protein, a murine αKlotho protein, or a porcine αKlotho protein.

9. The method of claim 1, wherein the sTGFβ-R2 protein and/or the αKlotho protein is an Fc fusion protein comprising an Ig Fc domain.

10. The method of claim 1, wherein the first viral vector and/or the second viral vector is administered by:

(i) intravenous injection; or (ii) intra-articular injection into cartilage at an osteoarthritic site.

11. The method of claim 1, comprising:

(i) reducing a progression of osteoarthritis in the subject, as compared to a control subject;

(ii) increasing, regenerating, or regrowing cartilage at an osteoarthritic site in the subject, as compared to a control subject; and/or (iii) reducing inflammation at an osteoarthritic site in the subject, as compared to a control subject.

12. The method of claim 1, wherein the subject is a mammal.

13. The method of claim 4, wherein the promoter comprises a constitutive promoter or an inducible promoter.

14. The method of claim 4, wherein the promoter comprises a cell-specific promoter or a tissue-specific promoter.

15. The method of claim 14, wherein the tissue-specific promoter comprises a liver-specific promoter.

16. The method of claim 4, wherein the promoter comprises an hEf1α promoter, an shEf1α promoter, a truncated hEf1α promoter, a CAG promoter, a cytomegalovirus (CMV) promoter, a human al-anti-trypsin (hAAT) promoter, a thyroid hormone-binding globulin promoter, an albumin promoter, a thyroxin-binding globulin (TBG) promoter, a hepatic control region (HCR)-ApoCII hybrid promoter, a CASI promoter, an HCR-hAAT hybrid promoter, an hAAT promoter combined with mouse albumin gene enhancer (Ealb) element, or an apolipoprotein E promoter.

17. The method of claim 5, wherein the 3' untranslated region comprises a WPRE sequence, a WPRE3 sequence, an SV40 late polyadenylation signal sequence, an SV40 late polyadenylation signal truncated sequence, an HBG polyadenylation signal sequence, a rabbit beta-globin polyadenylation signal sequence, a bovine bgpA sequence, an ETC polyadenylation signal sequence, or any combination thereof.

18. The method of claim 6, wherein the AAV vector is or is derived from an AAV1 viral vector, an AAV2 viral vector, an AAV3 viral vector, an AAV4 viral vector, an AAV5 viral vector, an AAV6 viral vector, an AAV7 viral vector, an AAV8 viral vector, an AAV9 viral vector, an AAV10 viral vector, an AAV11 viral vector, an AAV12 viral vector, an AAV2.5 viral vector, an AAV-DJ viral vector, or an AAVrh10.XX viral vector.

19. The method of claim 6, wherein the AAV vector is an AAV-DJ viral vector.

20. The method of claim 7, wherein the sTGFβ-R2 protein comprises an amino acid sequence having at least 90% sequence identity to the amino acid sequence set forth in SEQ ID NO: 3.

21. The method of claim 8, wherein the αKlotho protein comprises an amino acid sequence having at least 90% sequence identity to the amino acid sequence set forth in SEQ ID NO: 1.

22. The method of claim 9, wherein the Ig Fc domain comprises a human Fc, a canine Fc, a feline Fc, a bovine Fc, an ovine Fc, a caprine Fc, an equine Fc, a murine Fc, a porcine Fc, or an Fc subtype thereof including IgG1, IgG2a, IgG2b, IgG3, or IgG4.

23. The method of claim 9, wherein the Ig Fc domain comprises an amino acid sequence having at least 90% sequence identity to the amino acid sequence set forth in SEQ ID NO: 5, SEQ ID NO: 6, or SEQ ID NO: 7.

24. The method of claim 12, wherein the mammal is a human or a canine.

\* \* \* \* \*

5